US012788248B2

(12) United States Patent
Alambeigi et al.

(10) Patent No.: US 12,788,248 B2
(45) Date of Patent: Nov. 10, 2026

(54) FOUR-DIMENSIONAL TACTILE SENSING SYSTEM, DEVICE, AND METHOD

(71) Applicant: Board of Regents, The University of Texas System, Austin, TX (US)

(72) Inventors: Farshid Alambeigi, Austin, TX (US); Uksang Yoo, Cortland, NY (US); Naruhiko Ikoma, Houston, TX (US); Ozdemir Can Kara, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 18/706,866

(22) PCT Filed: Nov. 4, 2022

(86) PCT No.: PCT/US2022/048940
§ 371 (c)(1),
(2) Date: May 2, 2024

(87) PCT Pub. No.: WO2023/081342
PCT Pub. Date: May 11, 2023

(65) Prior Publication Data

US 2025/0031968 A1 Jan. 30, 2025

Related U.S. Application Data

(60) Provisional application No. 63/276,259, filed on Nov. 5, 2021.

(51) Int. Cl.
*A61B 5/00* (2006.01)
*A61B 1/00* (2006.01)
(Continued)

(52) U.S. Cl.
CPC ...... *A61B 5/0053* (2013.01); *A61B 1/000096* (2022.02); *A61B 1/00097* (2022.02);
(Continued)

(58) Field of Classification Search
CPC ............ A61B 5/0053; A61B 1/000096; A61B 1/00097; A61B 1/0057; A61B 1/05;
(Continued)

(56) References Cited

U.S. PATENT DOCUMENTS 4,428,670 A * 1/1984 Ruell .................... G06V 40/13
356/71
5,471,988 A * 12/1995 Fujio ..................... A61B 8/445
601/3
(Continued)

OTHER PUBLICATIONS

Lin [PCA/SVM-Based Method for Pattern Detection in a Multisensor System, Mathematical Problems in Engineering vol. 2018, Article ID 6486345], (Year: 2018).*
(Continued)

*Primary Examiner* — Oommen Jacob
(74) *Attorney, Agent, or Firm* — Riverside Law LLP

(57) ABSTRACT

A four-dimensional tactile sensing system comprises a housing including a front-facing camera and at least one tactile sensor device positioned on the exterior surface of the housing, comprising an elastomer attached to a support plate a camera positioned proximate to the support plate, and opposite the elastomer, and at least one light source positioned proximate to the support plate and the camera, and opposite the elastomer. A four-dimensional tactile sensing device and tactile morphology method and algorithms are also disclosed.

8 Claims, 35 Drawing Sheets

(51) Int. Cl.

| | |
|---|---|
| ***A61B 1/005*** | (2006.01) |
| ***A61B 1/05*** | (2006.01) |
| ***A61B 1/06*** | (2006.01) |
| ***A61B 1/31*** | (2006.01) |
| ***A61B 34/30*** | (2016.01) |
| ***A61B 90/00*** | (2016.01) |
| ***A61M 25/01*** | (2006.01) |

(52) U.S. Cl.

CPC .............. *A61B 1/0057* (2013.01); *A61B 1/05* (2013.01); *A61B 1/0638* (2013.01); *A61B 1/0676* (2013.01); *A61B 1/31* (2013.01); *A61B 34/30* (2016.02); *A61B 1/0051* (2013.01); *A61B 2034/301* (2016.02); *A61B 2090/3937* (2016.02); *A61B 2562/12* (2013.01); *A61B 2562/164* (2013.01); *A61M 25/0113* (2013.01); *A61M 25/0147* (2013.01); *A61M 25/0155* (2013.01)

(58) Field of Classification Search

CPC ....... A61B 1/0638; A61B 1/0676; A61B 1/31; A61B 34/30; A61B 1/0051; A61B 2034/301; A61B 2090/3937; A61B 2562/12; A61B 2562/164; A61B 1/00006; A61B 1/00009; A61B 1/2736; A61M 25/0113; A61M 25/0147; A61M 25/0155; G01L 5/166; G01L 5/228; G01L 1/24; G06N 3/0464; G06N 20/10; G06N 3/09

See application file for complete search history.

(56) References Cited

U.S. PATENT DOCUMENTS

| | | | | |
|---|---|---|---|---|
| 5,662,587 | A * | 9/1997 | Grundfest | A61B 1/0051 600/116 |
| 6,648,814 | B2 * | 11/2003 | Kim | A61B 1/00156 356/241.6 |
| 7,420,155 | B2 * | 9/2008 | Mizota | G01L 5/228 250/221 |
| 8,069,735 | B1 * | 12/2011 | Egorov | G01L 1/146 73/862.041 |
| 11,547,486 | B1 * | 1/2023 | Roh | G16H 50/50 |
| 2002/0087048 | A1 * | 7/2002 | Brock | B25J 3/04 600/114 |
| 2006/0293562 | A1 * | 12/2006 | Uchimura | A61B 1/00096 600/110 |
| 2007/0276291 | A1 * | 11/2007 | Hewit | A61B 5/1076 600/587 |
| 2009/0315989 | A1 * | 12/2009 | Adelson | G06F 3/042 348/135 |
| 2010/0149183 | A1 * | 6/2010 | Loewke | G06V 20/693 345/424 |
| 2011/0136985 | A1 | 6/2011 | Moon | |
| 2012/0041345 | A1 * | 2/2012 | Rajamani | A61B 5/103 600/587 |
| 2013/0144191 | A1 * | 6/2013 | Egorov | A61B 5/227 600/591 |
| 2014/0104395 | A1 * | 4/2014 | Rohaly | G01B 11/245 348/47 |
| 2015/0011830 | A1 * | 1/2015 | Hunter | A61B 1/0016 600/118 |
| 2016/0354159 | A1 | 12/2016 | Hunter | |
| 2017/0164869 | A1 * | 6/2017 | Lee | A61B 34/20 |
| 2017/0239821 | A1 | 8/2017 | Lessing | |
| 2017/0312981 | A1 | 11/2017 | Selbertinger | |
| 2019/0053848 | A1 * | 2/2019 | Cao | A61B 5/6852 |
| 2020/0050271 | A1 | 2/2020 | Xu | |
| 2020/0205665 | A1 * | 7/2020 | Won | G02B 6/10 |
| 2021/0318116 | A1 * | 10/2021 | Adelson | G01L 1/24 |
| 2021/0381823 | A1 * | 12/2021 | Kennedy | A61B 34/30 |
| 2022/0066456 | A1 * | 3/2022 | Ebrahimi Afrouzi | G06F 3/04883 |
| 2022/0354380 | A1 * | 11/2022 | Tata | A61B 34/10 |
| 2022/0409305 | A1 * | 12/2022 | Li | A61B 1/2736 |
| 2025/0031968 | A1 * | 1/2025 | Alambeigi | A61B 1/00006 |

OTHER PUBLICATIONS

Winstone [Toward Bio-Inspired Tactile Sensing Capsule Endoscopy for Detection of Submucosal Tumors, IEEE Sensors Journal, vol. 17, No. 3, Feb. 1, 2017] (Year: 2017).*

M. K. Johnson, F. Cole, A. Raj, and E. H. Adelson, "Microgeometry capture using an elastomeric sensor," ACM Transactions on Graphics (TOG), vol. 30, No. 4, pp. 1-8, 2011.

M. Kalaitzakis, B. Cain, S. Carroll, A. Ambrosi, C. Whitehead, and N. Vitzilaios, "Fiducial markers for pose estimation," Journal of Intelligent & Robotic Systems, vol. 101, No. 4, pp. 1-26, 2021.

M. Park, B.-G. Bok, J.-H. Ahn, and M.-S. Kim, "Recent advances in tactile sensing technology," Micromachines, vol. 9, No. 7, p. 321, 2018.

M. S. Arian, C. A. Blaine, G. E. Loeb, and J. A. Fishel, "Using the biotac as a tumor localization tool," in 2014 IEEE Haptics Symposium (HAPTICS). IEEE, 2014, pp. 443-448.

Medtronic, "GI Genius™ Intelligent Endoscopy Module | Medtronic," 2020. https://www.medtronic.com/covidien/en-gb/products/gastrointestinal-artificial-intelligence/gi-genius-intelligent-endoscopy.html (accessed May 2, 2021) (pp. 1-5).

N. Hoerter, S. A. Gross, and P. S. Liang, "Artificial Intelligence and Polyp Detection," Curr. Treat. Options Gastroenterol., vol. 18, No. 1, pp. 120-136, Mar. 2020, doi: 10.1007/s11938-020-00274-2.

N. Kattavenos, B. Lawrenson, T. Frank, M. Pridham, R. Keatch, and A. Cuschieri, "Force-sensitive tactile sensor for minimal access surgery," Minimally Invasive Therapy & Allied Technologies, vol. 13, No. 1, pp. 42-46, 2004.

N. R. Sinatra, C. B. Teeple, D. M. Vogt, K. K. Parker, D. F. Gruber, and R. J. Wood, "Ultragentle manipulation of delicate structures using a soft robotic gripper," Science Robotics, vol. 4, No. 33, p. eaax5425, 2019.

N. Venkatayogi, O. C. Kara, J. Bonyun, N. Ikoma and F. Alambeigi, "Classification of Colorectal Cancer Polyps via Transfer Learning and Vision-Based Tactile Sensing," 2022 IEEE Sensors, Dallas, TX, USA, 2022, pp. 1-4, doi: 10.1109/SENSORS52175.2022.9967308.

N. Wettels, V. J. Santos, R. S. Johansson, and G. E. Loeb, "Biomimetic tactile sensor array," Advanced Robotics, vol. 22, No. 8, pp. 829-849, 2008.

Noble, William S. "What is a support vector machine ?. " Nature biotechnology vol. 24, 12 (2006): pp. 1565-1567. doi:10.1038/nbt1206-1565.

P. Greenwald, "Colon cancer overview," 1992. vol. 70, pp. 1206-1215. Publisher: John Wiley & Sons, Ltd.

P. S. Wellman, E. P. Dalton, D. Krag, K. A. Kern, and R. D. Howe, "Tactile imaging of breast masses: first clinical report," Archives of surgery, vol. 136, No. 2, pp. 204-208, 2001.

Péter Baki, Gábor Székely, Gábor Kósa, Design and characterization of a novel, robust, tri-axial force sensor, Sensors and Actuators A: Physical, vol. 192, 2013, pp. 101-110, ISSN 0924-4247, https://doi.org/10.1016/j.sna.2012.11.035.

R. Ahmadi, S. Arbatani, M. Packirisamy, and J. Dargahi, "Microoptical force distribution sensing suitable for lump/artery detection," Biomedical microdevices, vol. 17, No. 1, pp. 1-12, 2015.

R. Li and E. H. Adelson, "Sensing and recognizing surface textures using a gelsight sensor," in Proceedings of the IEEE Conference on Computer Vision and Pattern Recognition, 2013, pp. 1241-1247.

R. Li, R. Platt, W. Yuan, A. ten Pas, N. Roscup, M. A. Srinivasan, and E. Adelson, "Localization and manipulation of small parts using gelsight tactile sensing," in 2014 IEEE/RSJ International Conference on Intelligent Robots and Systems. IEEE, 2014, pp. 3988-3993.

R. S. Dahiya, M. Valle, et al., "Tactile sensing for robotic applications," Sensors, Focus on Tactile, Force and Stress Sensors, pp. 298-304, 2008.

S. Dong, W. Yuan and E. H. Adelson, "Improved GelSight tactile sensor for measuring geometry and slip," 2017 IEEE/RSJ Interna-

(56) References Cited

OTHER PUBLICATIONS tional Conference on Intelligent Robots and Systems (IROS), Vancouver, BC, Canada, 2017, pp. 137-144, doi: 10.1109/IROS.2017.8202149.

S. Garrido-Jurado, R. Munoz-Salinas, F. J. Madrid-Cuevas, and M. J.˜ Marin-Jimenez, "Automatic generation and detection of highly reliable fiducial markers under occlusion," Pattern Recognition, vol. 47, No. 6, pp. 2280-2292, 2014.

S. J. Thakkar and G. S. Kochhar, "Artificial intelligence for real-time detection of early esophageal cancer: another set of eyes to better visualize," Gastrointestinal Endoscopy, vol. 91, No. 1. Mosby Inc., pp. 52-54, Jan. 1, 2020, doi: 10.1016/j.gie.2019.09.036.

S. Patino-Barrientos, D. Sierra-Sosa, B. Garcia-Zapirain, C. Castillo-Olea, and A. Elmaghraby, "Kudo's classification for colon polyps assessment using a deep learning approach," Appl. Sci., vol. 10, No. 2, p. 501, Jan. 2020, doi: 10.3390/app10020501.

Shia, J., Schultz, N., Kuk, D., Vakiani, E., Middha, S., Segal, N.H., Hechtman, J.F., Berger, M.F., Stadler, Z.K., Weiser, M.R. and Wolchok, J.D., 2017. Morphological characterization of colorectal cancers in The Cancer Genome Atlas reveals distinct morphology-molecular associations: clinical and biological implications. Modern pathology, 30(4), pp. 599-609.

T. Kaltenbach, J. C. Anderson, C. A. Burke, J. A. Dominitz, S. Gupta, D. Lieberman, D. J. Robertson, A. Shaukat, S. Syngal, and D. K. Rex., 2020. "Endoscopic removal of colorectal lesions: Recommendations by the US multi-society task force on colorectal cancer," vol. 115, No. 3 (pp. 1-30).

U. H. Shah, R. Muthusamy, D. Gan, Y. Zweiri, and L. Seneviratne, "On the design and development of vision-based tactile sensors," Journal of Intelligent & Robotic Systems, vol. 102, No. 4, pp. 1-27, 2021.

W. K. Do and M. Kennedy, "Densetact: Optical tactile sensor for dense shape reconstruction," in 2022 International Conference on Robotics and Automation (ICRA). IEEE, 2022, pp. 6188-6194.

W. Kim, W. D. Kim, J.-J. Kim, C.-H. Kim, and J. Kim, "Uvtac: Switchable uv marker-based tactile sensing finger for effective force estimation and object localization," IEEE Robotics and Automation Letters, vol. 7, No. 3, pp. 6036-6043, 2022.

W. Othman and M. A. Qasaimeh, "Tactile sensing for minimally invasive surgery: Conventional methods and potential emerging tactile technologies," Frontiers in Robotics and AI, p. 376, 2021.

W. Yuan et al., "Tactile measurement with a gelsight sensor," Ph.D. dissertation, Massachusetts Institute of Technology, 2014 (pp. 1-121).

W. Yuan, C. Zhu, A. Owens, M. A. Srinivasan, and E. H. Adelson, "Shape-independent hardness estimation using deep learning and a gelsight tactile sensor," in 2017 IEEE International Conference on Robotics and Automation (ICRA). IEEE, 2017, pp. 951-958.

Wang, Thomas D, and Jacques Van Dam. "Optical biopsy: a new frontier in endoscopic detection and diagnosis." Clinical gastroenterology and hepatology : the official clinical practice journal of the American Gastroenterological Association vol. 2,9 (2004): 744-53. doi:10.1053/S1542-3565(04)00345-3.

Ward-Cherrier B, Pestell N, Cramphorn L, Winstone B, Giannaccini ME, Rossiter J, Lepora NF. The TacTip Family: Soft Optical Tactile Sensors with 3D-Printed Biomimetic Morphologies. Soft Robot. Apr. 2018;5(2):216-227. doi: 10.1089/soro.2017.0052.

X. Lin and M. Wiertlewski, "Sensing the frictional state of a robotic skin via subtractive color mixing," IEEE Robotics and Automation Letters, vol. 4, No. 3, pp. 2386-2392, 2019.

X. Lin, L. Willemet, A. Bailleul, and M. Wiertlewski, "Curvature sensing with a spherical tactile sensor using the color-interference of a marker array," in 2020 IEEE International Conference on Robotics and Automation (ICRA). IEEE, 2020, pp. 603-609.

Y. Liu and F. Alambeigi, "Effect of External and Internal Loads on Tension Loss of Tendon-Driven Continuum Manipulators," in IEEE Robotics and Automation Letters, vol. 6, No. 2, pp. 1606-1613, Apr. 2021, doi: 10.1109/LRA.2021.3058913.

Y. Liu, R. Bao, J. Tao, J. Li, M. Dong, and C. Pan, "Recent progress in tactile sensors and their applications in intelligent systems," Science Bulletin, vol. 65, No. 1, pp. 70-88, 2020.

Y. Liu, S. H. Ahn, U. Yoo, A. R. Cohen, and F. Alambeigi, "Toward analytical modeling and evaluation of curvature-dependent distributed friction force in tendon-driven continuum manipulators," in 2020 IEEE/RSJ International Conference on Intelligent Robots and Systems (IROS), Oct. 25-29, 2020, pp. 8823-8828.

Y. Liu, T. G. Mohanraj, M. R. Rajebi, L. Zhou, and F. Alambeigi, "Multiphysical analytical modeling and design of a magnetically steerable robotic catheter for treatment of peripheral artery disease," IEEE/ASME Transactions on Mechatronics, 2022 (pp. 1-9).

Yuan, Wenzhen, Siyuan Dong, and Edward H. Adelson. 2017. "GelSight: High-Resolution Robot Tactile Sensors for Estimating Geometry and Force" Sensors 17, No. 12: 2762. https://doi.org/10.3390/s17122762 (pp. 1-21).

"Flat polyps: Why finding them requires skill," UCI Health, 2017. https://www.ucihealth.org/blog/2017/03/flat-polyps-colonoscopy (accessed May 2, 2021) (pp. 1-4).

A. C. Abad and A. Ranasinghe, "Visuotactile sensors with emphasis on gelsight sensor: A review," IEEE Sensors Journal, vol. 20, No. 14, pp. 7628-7638, 2020.

A. C. Bateman and P. Patel, "Lower gastrointestinal endoscopy: guidance on indications for biopsy," Frontline Gastroenterol., vol. 5, No. 2, pp. 96-102, Apr. 2014, doi: 10.1136/flgastro-2013-100412.

A. de Oliveira Junior, L. Piardi, E. G. Bertogna, and P. Leitao,˜ "Improving the mobile robots indoor localization system by combining slam with fiducial markers," in 2021 Latin American Robotics Symposium (LARS), 2021 Brazilian Symposium on Robotics (SBR), and 2021 Workshop on Robotics in Education (WRE). IEEE, 2021, pp. 234-239.

A. Mittal, A. K. Moorthy, and A. C. Bovik, "No-reference image quality assessment in the spatial domain," IEEE Transactions on image processing, vol. 21, No. 12, pp. 4695-4708, 2012.

A. Yamaguchi and C. G. Atkeson, "Recent progress in tactile sensing and sensors for robotic manipulation: can we turn tactile sensing into vision?" Advanced Robotics, vol. 33, No. 14, pp. 661-673, 2019.

A. Yamaguchi and C. G. Atkeson, "Tactile behaviors with the visionbased tactile sensor fingervision," International Journal of Humanoid Robotics, vol. 16, No. 03, p. 1940002, 2019.

A. Z. Gimeno-García et al., "Displasia de alto grado como factor de riesgo de neoplasia colorrectal avanzada metacrónica, en pacientes con adenomas avanzados," Gastroenterol. Hepatol., vol. 30, No. 4, pp. 207-211, Apr. 2007, doi: 10.1157/13100586.

Abiri, Ahmad et al. "Artificial palpation in robotic surgery using haptic feedback." Surgical endoscopy vol. 33,4 (2019): 1252-1259. doi:10.1007/s00464-018-6405-8.

An, J.Y., Kang, T.H., Choi, M.G., Noh, J.H., Sohn, T.S. and Kim, S., 2008. Borrmann type IV: an independent prognostic factor for survival in gastric cancer. Journal of Gastrointestinal Surgery, 12(8), pp. 1364-1369.

B. Winstone, C. Melhuish, T. Pipe, M. Callaway, and S. Dogramadzi, "Toward bio-inspired tactile sensing capsule endoscopy for detection of submucosal tumors," in IEEE Sensors Journal, vol. 17, No. 3, pp. 848-857, Feb. 1, 2017.

Bhandari, Abhishek et al. "Colorectal cancer is a leading cause of cancer incidence and mortality among adults younger than 50 years in the USA: a SEER-based analysis with comparison to other young-onset cancers." Journal of investigative medicine : the official publication of the American Federation for Clinical Research vol. 65,2 (2017): 311-315. doi:10.1136/jim-2016-000229.

C. Mela, F. Papay, and Y. Liu, "Novel multimodal, multiscale imaging system with augmented reality," Diagnostics, vol. 11, No. 3, p. 441, 2021.

C.-H. Chuang, T.-H. Li, I.-C. Chou, and Y.-J. Teng, "Piezoelectric tactile sensor for submucosal tumor detection in endoscopy," Sensors and Actuators A: Physical, vol. 244, pp. 299-309, 2016.

C.-H. Won, J.-H. Lee, and F. Saleheen, "Tactile sensing systems for tumor characterization: A review," IEEE Sensors Journal, vol. 21, No. 11, pp. 12578-12588, 2021.

Chi C, Sun X, Xue N, Li T, Liu C. Recent Progress in Technologies for Tactile Sensors. Sensors. 2018; 18(4):948. https://doi.org/10.3390/s18040948.

(56) References Cited

OTHER PUBLICATIONS

Ciuti, G., Caliò, R., Camboni, D. et al. Frontiers of robotic endoscopic capsules: a review. J Micro-Bio Robot 11, 1-18 (2016). https://doi.org/10.1007/s12213-016-0087-x.
D. Camboni et al., "Endoscopic Tactile Capsule for Non-Polypoid Colorectal Tumour Detection," in IEEE Transactions on Medical Robotics and Bionics, vol. 3, No. 1, pp. 64-73, Feb. 2021, doi: 10.1109/TMRB.2020.3037255.
Dik, Vincent K et al. "Endoscopic innovations to increase the adenoma detection rate during colonoscopy." World journal of gastroenterology vol. 20,9 (2014): 2200-11. doi:10.3748/wjg.v20.i9.2200.
E. Olson, "Apriltag: A robust and flexible visual fiducial system," in 2011 IEEE international conference on robotics and automation. IEEE, 2011, pp. 3400-3407.
Endoscopic Classification Review Group. "Update on the paris classification of superficial neoplastic lesions in the digestive tract." Endoscopy vol. 37,6 (2005): 570-8. doi:10.1055/s-2005-861352.
F. Bianchi, E. Trallori, D. Camboni, C. M. Oddo, A. Menciassi, G. Ciuti, and P. Dario, "Endoscopic tactile instrument for remote tissue palpation in colonoscopic procedures," in 2017 IEEE International Conference on Cyborg and Bionic Systems (CBS), pp. 248-252.
F. Ju, Y. Wang, Z. Zhang, Y. Wang, Y. Yun, H. Guo, and B. Chen, "A miniature piezoelectric spiral tactile sensor for tissue hardness palpation with catheter robot in minimally invasive surgery," Smart Materials and Structures, vol. 28, No. 2, p. 025033, 2019.
F. P. Villani, M. D. Cosmo, A. B. Simonetti, E. Frontoni, and' S. Moccia, "Development of an augmented reality system based on marker tracking for robotic assisted minimally invasive spine surgery," in International Conference on Pattern Recognition. Springer, 2021, pp. 461-475.
G. Li, S. Liu, L. Wang, and R. Zhu, "Skin-inspired quadruple tactile sensors integrated on a robot hand enable object recognition," Science Robotics, vol. 5, No. 49, p. eabc8134, 2020.
Gilani N, Stipho S, Panetta JD, Petre S, Young MA, Ramirez FC. Polyp detection rates using magnification with narrow band imaging and white light. World J Gastrointest Endosc. May 16, 2015;7(5):555-62. doi: 10.4253/wjge.v7.i5.555.
H. Awadie and M. J. Bourke, "When colonoscopy fails . . . Refer, Repeat, and Succeed," GE Portuguese Journal of Gastroenterology, vol. 25, No. 6. pp. 279-281, 2018, doi: 10.1159/000486804.
H. Heo, Y. Jin, D. Yang, C. Wier, A. Minard, N. B. Dahotre, and A. Neogi, "Manufacturing and characterization of hybrid bulk voxelated biomaterials printed by digital anatomy 3d printing," Polymers, vol. 13, No. 1, p. 123, 2020.
H. Park, H. Lee, K. Park, S. Mo and J. Kim, "Deep Neural Network Approach in Electrical Impedance Tomography-based Real-time Soft Tactile Sensor," 2019 IEEE/RSJ International Conference on Intelligent Robots and Systems (IROS), Macau, China, 2019, pp. 7447-7452, doi: 10.1109/IROS40897.2019.8968532.
H. Park, K. Park, S. Mo, and J. Kim, "Deep neural network based electrical impedance tomographic sensing methodology for large-area robotic tactile sensing," in IEEE Transactions on Robotics, vol. 37, No. 5, Oct. 2021, pp. 1-14.
Heijnsdijk, E A M et al. "Inter- and intraindividual variabilities of perforation forces of human and pig bowel tissue." Surgical endoscopy vol. 17,12 (2003): 1923-6. doi:10.1007/s00464-003-9002-3.
I. Bandyopadhyaya, D. Babu, A. Kumar and J. Roychowdhury, "Tactile sensing based softness classification using machine learning," 2014 IEEE International Advance Computing Conference (IACC), Gurgaon, India, 2014, pp. 1231-1236, doi: 10.1109/IAdCC.2014.6779503.
Ikoma, N. ASO Author Reflections: Fluorescent-Image Guidance in Surgical Oncology. Ann Surg Oncol 27, 5323-5324 (2020). https://doi.org/10.1245/s10434-020-08551-1.
J. Dargahi, S. Najarian, and K. Najarian, "Development and threedimensional modelling of a biological-tissue grasper tool equipped with a tactile sensor," Canadian Journal of Electrical and Computer Engineering, vol. 30, No. 4, pp. 225-230, 2005.
J. Lee et al., "Risk factors of missed colorectal lesions after colonoscopy," Med. (United States), vol. 96, No. 27, Jul. 2017, doi: 10.1097/MD.0000000000007468 (pp. 1-6).
J. M. Gandarias, J. M. Gomez-de Gabriel, and A. J. Garc' '$_{l}$a-Cerezo, "Enhancing perception with tactile object recognition in adaptive grippers for human-robot interaction," Sensors, vol. 18, No. 3, p. 692, 2018.
J. Zhu, A. Cherubini, C. Dune, D. Navarro-Alarcon, F. Alambeigi, D. Berenson, F. Ficuciello, K. Harada, X. Li, J. Pan et al., "Challenges and outlook in robotic manipulation of deformable objects," arXiv preprint arXiv:2105.01767, 2021 (pp. 1-9).
Japanese Gastric Cancer Association. Japanese gastric cancer treatment guidelines 2014 (ver. 4). Gastric Cancer. Jan. 2017;20(1):1-19.
Jung K, Park MI, Kim SE, Park SJ. Borrmann Type 4 Advanced Gastric Cancer: Focus on the Development of Scirrhous Gastric Cancer. Clin Endosc. Jul. 2016;49(4):336-45.
K. Kamiyama, K. Vlack, T. Mizota, H. Kajimoto, K. Kawakami, and S. Tachi, "Vision-based sensor for real-time measuring of surface traction fields," IEEE Computer Graphics and Applications, vol. 25, No. 1, pp. 68-75, 2005.
K. Nozu and K. Shimonomura, "Robotic bolt insertion and tightening based on in-hand object localization and force sensing," in 2018 IEEE/ASME International Conference on Advanced Intelligent Mechatronics (AIM). IEEE, 2018, pp. 310-315.
K. Sato, K. Kamiyama, N. Kawakami, and S. Tachi, "Finger-shaped gelforce: sensor for measuring surface traction fields for robotic hand," IEEE Transactions on Haptics, vol. 3, No. 1, pp. 37-47, 2009.
K. Shimonomura, "Tactile image sensors employing camera: A review," Sensors, vol. 19, No. 18, p. 3933, 2019.
Kudo, S et al. "Diagnosis of colorectal tumorous lesions by magnifying endoscopy." Gastrointestinal endoscopy vol. 44,1 (1996): 8-14. doi:10.1016/s0016-5107(96)70222-5.
Ladabaum, Uri et al. "Real-time optical biopsy of colon polyps with narrow band imaging in community practice does not yet meet key thresholds for clinical decisions." Gastroenterology vol. 144,1 (2013): 81-91. doi:10.1053/j.gastro.2012.09.054 Edition: Oct. 3, 2012.
Li, Chen et al. "Macroscopic Borrmann type as a simple prognostic indicator in patients with advanced gastric cancer." Oncology vol. 77,3-4 (2009): 197-204.
M. A. Turk and A. P. Pentland, "Face recognition using eigenfaces," Proceedings. 1991 IEEE Computer Society Conference on Computer Vision and Pattern Recognition, Maui, HI, USA, 1991, pp. 586-591, doi: 10.1109/CVPR.1991.139758.
M. Beyeler, OpenCV with Python blueprints. Packt Publishing Ltd, 2015 (pp. 1-231).
M. Fiala, "Artag, a fiducial marker system using digital techniques," in 2005 IEEE Computer Society Conference on Computer Vision and Pattern Recognition (CVPR'05), vol. 2. IEEE, 2005, pp. 590-596.
M. K. Johnson and E. H. Adelson, "Retrographic sensing for the measurement of surface texture and shape," in 2009 IEEE Conference on Computer Vision and Pattern Recognition. IEEE, 2009, pp. 1070-1077.

* cited by examiner

MATERIAL PROPERTIES OF POLYP PHANTOMS

| Material | Color | Material Property* | | |
|---|---|---|---|---|
| | | SH | TS | ME |
| CLEAR | Clear | ≥ D-80 | 38 MPa | 12 % |
| Vero | Black | D-85 | 55 MPa | 20 % |
| Elastic | Clear | A-50 | 3.2 MPa | 100 % |
| TangoBlackPlus | Black | A-27 | 1.2 MPa | 110 % |

* SH: Shore Hardness; TS: Tensile Strength; FS: Flexural Strength ME: Max Elongation

FIG. 12

FOUR-DIMENSIONAL TACTILE SENSING SYSTEM, DEVICE, AND METHOD

CROSS-REFERENCE TO RELATED APPLICATIONS

This application is a U.S. national phase application filed under 35 U.S.C. § 371 claiming benefit to International Patent Application No. PCT/US2022/048940, filed Nov. 4, 2022, which is entitled to priority of U.S. Provisional Patent Application No. 63/276,259, filed on Nov. 5, 2021, the contents of which are each incorporated by reference herein in their entirety.

BACKGROUND OF THE INVENTION

Tactile sensing can provide increased information for a variety of applications ranging from medical applications such as tumor classification, inspections of industrial and municipal systems such as pipe inspections, and farming applications such as fruit harvesting, for example.

Colorectal and gastric cancers are leading types of cancer worldwide and are the third leading cause of death related to cancer in the US (see A. Bhandari et al., "Colorectal cancer is a leading cause of cancer incidence and mortality among adults younger than 50 years in the USA: a SEER-based analysis with comparison to other young-onset cancers," vol. 65, no. 2, p. 311). Morphological characteristics (i.e., shape and texture) of gastric and colorectal cancers are well-known to be associated with tumor stage, pathological subtypes, presence of signet-ring cell morphology, incidence of lymph node involvement, and treatment and survival outcomes. A strong association has been reported between tumor morphology and pathologic and molecular characteristics of the tumor such as tumor grade, signet-ringed cell, and microsatellite instability histology. However, evaluation of the shape and texture of the tumor is subjective and accurate classification requires extensive experience and has not achieved international consensus. Therefore, despite its significant potential, tumor geometry and texture has not yet fully been integrated to guide treatment strategy, such as neoadjuvant therapy regimen (e.g., microsatellite instability-high colorectal cancer frequently responds to immune-checkpoint inhibitor, diffuse-type signet ring cell gastric cancer are less likely to respond to conventional chemotherapy).

Furthermore, current robotic surgical platforms still lack providing reliable tactile feedback to a surgeon, which limits the safety and efficacy of the operations. Hence, surgeons rely solely on visual feedback to identify tumor type and location to guide the extent of the resection of colorectal and gastric cancer. Of note, this may increase the risk of missed lesions and/or unnecessarily extended resection of those organs due to the lack of accurate tumor localization.

Haptics-enabled robots that can provide accurate feedback to surgeons are critically needed to improve surgical accuracy and treatment outcomes of colorectal and gastric cancer surgery. Similarly, in endoscopy (colonoscopy and gastroscopy), even with the recent advancement of optics, the technology still lacks tactile sensation for further detection and evaluation of the lesions. Endoscopic evaluation is still technically demanding (in terms of safe introduction and steering of the scope to evaluate the entire colon) and lesions can be easily missed at flexures of the colon or behind folds since the technique is completely dependent solely on visual information.

Tactile Sensing (TS) is the process of perceiving the physical properties of an object through a cutaneous touch-based interaction (see R. S. Dahiya et al., "Tactile sensing for robotic applications," Sensors, Focus on Tactile, Force and Stress Sensors, pp. 298-304, 2008). The acquired information can be very beneficial in many areas of robotics in which a robot interacts with hard or deformable objects. Examples include object manipulation (see A. Yamaguchi and C. G. Atkeson, "Recent progress in tactile sensing and sensors for robotic manipulation: can we turn tactile sensing into vision?" Advanced Robotics, vol. 33, no. 14, pp. 661-673, 2019), object texture or stiffness recognition (see G. Li et al., "Skin-inspired quadruple tactile sensors integrated on a robot hand enable object recognition," Science Robotics, vol. 5, no. 49, p. eabc8134, 2020), human-robot interaction (see J. M. Gandarias et al., "Enhancing perception with tactile object recognition in adaptive grippers for human-robot interaction," Sensors, vol. 18, no. 3, p. 692, 2018), and robot-assisted minimally invasive surgery (see F. Ju et al., A miniature piezoelectric spiral tactile sensor for tissue hardness palpation with catheter robot in minimally invasive surgery," Smart Materials and Structures, vol. 28, no. 2, p. 025033, 2019). As the application of TS in robotics is increasing, there is an imminent need for the development of high-resolution and high-accuracy TS devices that can safely and robustly interact with a soft or rigid environment. To address this crucial need, various tactile sensing technologies have been developed by many researchers. Examples include but are not limited to various electrical-based (e.g., piezoresistive, piezoelectric, inductive, and capacitive) and optical-based (e.g., intensity modulation, wavelength modulation, and phase modulation) hardware (see Y. Liu et al., "Recent progress in tactile sensors and their applications in intelligent systems," Science Bulletin, vol. 65, no. 1, pp. 70-88, 2020) (see M. Park et al., "Recent advances in tactile sensing technology," Micromachines, vol. 9, no. 7, p. 321, 2018). However, these approaches still mainly suffer from the large size (for optical tactile sensors), poor resolution (for piezoelectric tactile sensors), poor reliability (for inductive tactile sensors), and rigidity of the sensorized instrument making their usage impractical in a sensitive environment such as medical applications (see N. Kattavenos et al., "Force-sensitive tactile sensor for minimal access surgery," Minimally Invasive Therapy & Allied Technologies, vol. 13, no. 1, pp. 42-46, 2004) (see J. Dargahi et al., "Development and three-dimensional modelling of a biological-tissue grasper tool equipped with a tactile sensor," Canadian Journal of Electrical and Computer Engineering, vol. 30, no. 4, pp. 225-230, 2005) (see M. S. Arian et al., "Using the biotac as a tumor localization tool," in 2014 IEEE Haptics Symposium (HAPTICS). IEEE, 2014, pp. 443-448) (see P. S. Wellman et al., "Tactile imaging of breast masses: first clinical report," Archives of surgery, vol. 136, no. 2, pp. 204-208, 2001) (see N. Wettels et al., "Biomimetic tactile sensor array," Advanced Robotics, vol. 22, no. 8, pp. 829-849, 2008). Additionally, high interaction forces for providing adequate tactile feedback hinders the use of these TS devices when interacting with deformable and delicate environments (see E. Heijnsdijk et al., "Inter- and intraindividual variabilities of perforation forces of human and pig bowel tissue," Surgical Endoscopy and other interventional Techniques, vol. 17, no. 12, pp. 1923-1926, 2003) (see W. Othman and M. A. Qasaimeh, "Tactile sensing for minimally invasive surgery: Conventional methods and potential emerging tactile technologies," Frontiers in Robotics and AI, p. 376, 2021). Discrete or localized low-quality TS measurement area is another drawback of the aforementioned technologies (see F. Bianchi et al, "Endoscopic tactile instrument for remote tissue palpation in colonoscopic procedures," in 2017 IEEE International Conference on Cyborg and Bionic Systems (CBS). IEEE, 2017, pp. 248-252) (see C.-H. Won et al., "Tactile sensing systems for tumor characterization: A review," IEEE Sensors Journal, vol. 21, no. 11, pp. 12578-12588, 2021) (see C.-H. Chuang et al., "Piezoelectric tactile sensor for submucosal tumor detection in endoscopy," Sensors and Actuators A: Physical, vol. 244, pp. 299-309, 2016) (see P. Baki et al., "Design and characterization of' a novel, robust, tri-axial force sensor," Sensors and actuators A: physical, vol. 192, pp. 101-110, 2013) (see R. Ahmadi et al., "Microoptical force distribution sensing suitable for lump/artery detection," Biomedical microdevices, vol. 17, no. 1, pp. 1-12, 2015).

Besides the aforementioned TS devices, Vision-based Tactile Sensors (VTSs) have also recently been developed to enhance tactile perception via high-resolution visual information (see A. Yamaguchi and C. G. Atkeson, "Tactile behaviors with the visionbased tactile sensor fingervision," International Journal of Humanoid Robotics, vol. 16, no. 03, p. 1940002, 2019). Particularly, VTSs can provide qualitative 3D visual image reconstruction and localization of the interacting rigid or deformable objects by capturing very small deformations of an elastic gel layer that directly interacts with the objects' surface (see U. H. Shah et al., "On the design and development of vision-based tactile sensors," Journal of Intelligent & Robotic Systems, vol. 102, no. 4, pp. 1-27, 2021). The evolution of digital and small size cameras has improved the fabrication, sensitivity, and integration of the VTSs with different robotic systems (see A. C. Abad and A. Ranasinghe, "Visuotactile sensors with emphasis on gelsight sensor: A review," IEEE Sensors Journal, vol. 20, no. 14, pp. 7628-7638, 2020). Further, advancements in computer vision and machine learning algorithms have enabled real-time post processing and analysis of the high-resolution TS information provided by this sensor (see M. K. Johnson and E. H. Adelson, "Retrographic sensing for the measurement of surface texture and shape," in 2009 IEEE Conference on Computer Vision and Pattern Recognition. IEEE, 2009, pp. 1070-1077) (see K. Shimonomura, "Tactile image sensors employing camera: A review," Sensors, vol. 19, no. 18, p. 3933, 2019). GelSight is the most well-known VTS and has been used in various applications such as the surface texture recognition (see R. Li and E. H. Adelson, "Sensing and recognizing surface textures using a gelsight sensor," in Proceedings of the IEEE Conference on Computer Vision and Pattern Recognition, 2013, pp. 1241-1247), geometry measurement with deep learning algorithms (see W. Yuan et al., "Gelsight: High-resolution robot tactile sensors for estimating geometry and force," Sensors, vol. 17, no. 12, p. 2762, 2017), localization and manipulation of small objects (see R. Li et al., "Localization and manipulation of small parts using gelsight tactile sensing," in 2014 IEEE/RSJ International Conference on Intelligent Robots and Systems. IEEE, 2014, pp. 3988-3993), and hardness estimation (see W. Yuan et al., "Shape-independent hardness estimation using deep learning and a gelsight tactile sensor," in 2017 IEEE International Conference on Robotics and Automation (ICRA). IEEE, 2017, pp. 951-958). Despite these advancements and as one of the major drawbacks of these sensors, most of the current VTSs still can solely provide qualitative visual deformation images and cannot yet directly provide a quantitative measure of the gel layer deformation (see W. Yuan et al., "Gelsight: High-resolution robot tactile sensors for estimating geometry and force," Sensors, vol. 17, no. 12, p. 2762, 2017) (see W. K. Do and M. Kennedy, "Densetact: Optical tactile sensor for dense shape reconstruction," in 2022 International Conference on Robotics and Automation (ICRA). IEEE, 2022, pp. 6188-6194).

To address this limitation, various techniques have been proposed in the literature to provide a quantitative measure of the deformation when a VTS interacts with an object. These approaches can be mainly divided into two classes: the marker-tracking-based and reflective-membrane-based [21], sensors (see U. H. Shah et al., "On the design and development of vision-based tactile sensors," Journal of Intelligent & Robotic Systems, vol. 102, no. 4, pp. 1-27, 2021) (see W. Kim et al., "Uvtac: Switchable uv marker-based tactile sensing finger for effective force estimation and object localization," IEEE Robotics and Automation Letters, vol. 7, no. 3, pp. 6036-6043, 2022). For instance, GelForce (see K. Kamiyama et al., "Vision-based sensor for real-time measuring of surface traction fields," IEEE Computer Graphics and Applications, vol. 25, no. 1, pp. 68-75, 2005) (see K. Sato et al., "Finger-shaped gelforce: sensor for measuring surface traction fields for robotic hand," IEEE Transactions on Haptics, vol. 3, no. 1, pp. 37-47, 2009), and Chromatouch (see X. Lin et al., "Curvature sensing with a spherical tactile sensor using the color-interference of a marker array," in 2020 IEEE International Conference on Robotics and Automation (ICRA). IEEE, 2020, pp. 603-609) (see X. Lin and M. Wiertlewski, "Sensing the frictional state of a robotic skin via subtractive color mixing," IEEE Robotics and Automation Letters, vol. 4, no. 3, pp. 2386-2392, 2019), are examples of marker-tracking-based sensors, in which a pattern of markers is utilized within the elastomer body. When the interaction occurs between the sensing gel layer and the object, the markers' pattern is affected, and their movements can be processed to infer the tactile information. However, marker-based designs require an arduous and complex manufacturing procedure to robustly adhere and integrate the markers with the VTS gel layer. Examples of these procedures include casting or 3D-printing of gel layers (see U. H. Shah et al., "On the design and development of vision-based tactile sensors," Journal of Intelligent & Robotic Systems, vol. 102, no. 4, pp. 1-27, 2021) as well as relatively easier and inaccurate marker-printing approaches based on transfer papers or handwriting (see W. Yuan et al., "Gelsight: High-resolution robot tactile sensors for estimating geometry and force," Sensors, vol. 17, no. 12, p. 2762, 2017) (see W. Yuan et al., "Shape-independent hardness estimation using deep learning and a gelsight tactile sensor," in 2017 IEEE International Conference on Robotics and Automation (ICRA). IEEE, 2017, pp. 951-958). Nevertheless, these techniques suffer from wrinkling or inconsistencies in the printing pattern, which directly deteriorates the accuracy of the deformation measurements. On the contrary, reflective membrane-based sensors, called retrographic sensors, are employed for sensing the shape and texture of the objects through the analysis of the intensity change of the reflected light from the reflective elastic sensing surfaces (see U. H. Shah et al., "On the design and development of vision-based tactile sensors," Journal of Intelligent & Robotic Systems, vol. 102, no. 4, pp. 1-27, 2021). GelSight is the typical example of the reflective membrane-based VTS that can sense the deformations occurred on the sensor gel layer by the reconstruction of a high-resolution heightmap using colored LED lights, and photometric stereo (see M. K. Johnson and E. H. Adelson, "Retrographic sensing for the measurement of surface texture and shape," in 2009 IEEE Conference on Computer Vision and Pattern Recognition. IEEE, 2009, pp. 1070-

1077). Despite the benefits of using this technique, the flat surface of the gel layer can limit the sensing of the object's orientation. Moreover, tactile information regarding tangential forces and deformation cannot be accurately detected in this approach, and objects without textures or edges are not recognized very well in reflective membrane-based sensors (see W. Kim et al., "Uvtac: Switchable uv marker-based tactile sensing finger for effective force estimation and object localization," IEEE Robotics and Automation Letters, vol. 7, no. 3, pp. 6036-6043, 2022). To address the challenges associated with these two types of VTSs, Nozu et al. (see K. Nozu and K. Shimonomura, "Robotic bolt insertion and tightening based on in-hand object localization and force sensing," in 2018 IEEE/ASME International Conference on Advanced Intelligent Mechatronics (AIM). IEEE, 2018, pp. 310-315) developed a tactile sensor incorporating both reflective membrane-based sensing and marker-based design for in-hand object localization and force sensing. However, in this approach, utilized markers on the surface of the gel layer may occlude the view of the camera looking towards the reflective membrane, and therefore, deteriorating the quality of the extracted tactile information from the visual output. To mitigate this issue, recently, Kim et al. (see W. Kim et al., "Uvtac: Switchable uv marker-based tactile sensing finger for effective force estimation and object localization," IEEE Robotics and Automation Letters, vol. 7, no. 3, pp. 6036-6043, 2022) proposed a tactile sensor that merges both reflective membrane-based sensing and marker-based design to decouple the marker and reflective membrane images and offer a 3-axis force estimation and object localization. Similar to the previous VTS, however, this sensor only provides an estimated interaction force between the VTS and the object and does not provide quantitative information on the deformation of the gel layer.

Amid the tactile sensors, Vision-based Tactile Sensors (VTSs) have recently been developed to improve tactile perception via high-resolution visual information (see J. Zhu et al., "Challenges and outlook in robotic manipulation of deformable objects," arXiv preprint arXiv: 2105.01767, 2021). VTSs can provide high-resolution 3D visual image reconstruction and localization of the interacting objects by capturing tiny deformations of an elastic gel layer that directly interacts with the objects' surface (see U. H. Shah at al. "On the design and development of vision-based tactile sensors," Journal of Intelligent & Robotic Systems, vol. 102, no. 4, pp. 1-27, 2021). GelSight is the most well known VTS, developed by Johnson and Adelson (see M. K. Johnson and E. H. Adelson, "Retrographic sensing for the measurement of surface texture and shape," in 2009 IEEE Conference on Computer Vision and Pattern Recognition. IEEE, 2009, pp. 1070-1077), and has been utilized for various applications, including the surface texture recognition (see R. Li and E. H. Adelson, "Sensing and recognizing surface textures using a gelsight sensor," in Proceedings of the IEEE Conference on Computer Vision and Pattern Recognition, 2013, pp. 1241-1247), geometry measurement with deep learning algorithms (see W. Yuan et al., "Gelsight: High-resolution robot tactile sensors for estimating geometry and force," Sensors, vol. 17, no. 12, p. 2762, 2017), localization and manipulation of small objects (see R. Li et al. "Localization and manipulation of small parts using gelsight tactile sensing," in 2014 IEEE/RSJ International Conference on Intelligent Robots and Systems. IEEE, 2014, pp. 3988-3993, and hardness estimation (see W. Yuan et al., "Shape-independent hardness estimation using deep learning and a gelsight tactile sensor," in 2017 IEEE International Conference on Robotics and Automation (ICRA). IEEE, 2017, pp. 951-958). More details about the use of VTSs can be found in A. C. Abad and A. Ranasinghe, "Visuotactile sensors with emphasis on gelsight sensor: A review," IEEE Sensors Journal, vol. 20, no. 14, pp. 7628-7638, 2020.

The resolution and quality of the GelSight output (i.e., 3D images) highly depends on its hardware components (e.g., the utilized elastomer, optics, illumination (see W. Yuan et al., "Gelsight: High-resolution robot tactile sensors for estimating geometry and force," Sensors, vol. 17, no. 12, p. 2762, 2017) (see S. Dong et al. "Improved gelsight tactile sensor for measuring geometry and slip," in 2017 IEEE/RSJ International Conference on Intelligent Robots and Systems (IROS). IEEE, 2017, pp. 137-144), fabrication procedure (e.g., thickness and hardness of gel layer (see W. Yuan et al., "Tactile measurement with a gelsight sensor," Ph.D. dissertation, Massachusetts Institute of Technology, 2014)), and post-processing algorithms (see M. K. Johnson, F. Cole, A. Raj, and E. H. Adelson, "Microgeometry capture using an elastomeric sensor," ACM Transactions on Graphics (TOG), vol. 30, no. 4, pp. 1-8, 2011). More importantly, the above-mentioned parameters also directly affect the sensitivity and the durability of the fabricated VTS, where sensitivity is defined as the ability to obtain high-quality 3D images while applying low interaction forces independent of the shape, size, and material properties of objects, whereas durability refers to the effective life of the VTS without experiencing any wear and tear after multiple use cases on different objects.

The sensitivity and durability of VTSs are highly correlated. To build a sensitive sensor using the fabrication procedure proposed by Yuan et al., durability needs to be often compromised. For instance, reducing the gel layer's stiffness and/or thickness is a common technique to increase the sensitivity of the GelSight sensors; however, this approach may substantially reduce the durability of the sensor when interacting with different objects (see W. Yuan et al., "Gelsight: High-resolution robot tactile sensors for estimating geometry and force," Sensors, vol. 17, no. 12, p. 2762, 2017) (see M. K. Johnson et al., F. Cole, A. Raj, and E. H. Adelson, "Microgeometry capture using an elastomeric sensor," ACM Transactions on Graphics (TOG), vol. 30, no. 4, pp. 1-8, 2011). Moreover, to obtain a high-resolution image using a less sensitive GelSight sensor (i.e., having a high thickness and stiffness gel layer), often a higher interaction force is required to deform the gel layer and obtain high-resolution images. Of note, this might not be feasible for several applications (e.g., high-fidelity manipulation of fragile objects (see N. R. Sinatra et al. "Ultragentle manipulation of delicate structures using a soft robotic gripper," Science Robotics, vol. 4, no. 33, p. eaax5425, 2019) and surgical applications (see E. Heijnsdijk et al., "Inter- and intraindividual variabilities of perforation forces of human and pig bowel tissue," Surgical Endoscopy and other interventional Techniques, vol. 17, no. 12, pp. 1923-1926, 2003) (see Y. Liu at al., "Multiphysical analytical modeling and design of a magnetically steerable robotic catheter for treatment of peripheral artery disease," IEEE/ASME Transactions on Mechatronics, 2022) (see N. Venkatayogi et al., "Classification of colorectal cancer polyps via transfer learning and vision-based tactile sensing," To be appeared in 2022 IEEE Sensors) and may damage the sensor and reduce its durability. Therefore, there is a critical need for developing a VTS that simultaneously has high sensitivity and durability independent of its application.

Thus, there is a need in the art for systems and methods for quantifying tumor shape, texture, and stiffness to enable universal morphological classification that can be used to predict tumor histology, stage, and survival of colorectal and gastric cancers, and guide appropriate treatment regimens for tumors resulting in improved treatment outcomes. Moreover, endoscopic evaluation with shape and stiffness information using haptics technology would enable early detection of polyps/cancers and morphologic classification that leads to treatment guidance.

SUMMARY OF THE INVENTION

Some embodiments of the invention disclosed herein are set forth below, and any combination of these embodiments (or portions thereof) may be made to define another embodiment.

In one aspect, a four-dimensional tactile sensing system comprises a housing including a front-facing camera, and at least one tactile sensor device positioned on an exterior surface of the housing, comprising an elastomer attached to a support plate, a camera positioned proximate to the support plate, and opposite the elastomer, and at least one light source positioned proximate to the support plate and the camera, and opposite the elastomer.

In one embodiment, the housing comprises a pneumatically controlled soft robot. In one embodiment, the housing comprises a cable controlled soft robot. In one embodiment, the housing comprises a pneumatic actuation system configured to actuate the at least one tactile sensor device. In one embodiment, the at least one tactile sensor device is positioned within a skin on the exterior surface of the housing.

In one embodiment, the system further comprises a non-transitory computer-readable medium with instructions stored thereon, that when executed by a processor, perform the steps of acquiring a set of input images, each input image having an associated known target type and an applied force, performing a principal component analysis on the set of input images to calculate a set of parameters for each image of the set of input images, providing the sets of parameters to a support vector machine to calculate a set of support vectors to classify the parameters, and selecting a subset of the set of support vectors and an applied force threshold, such that for images having an applied force above the applied force threshold, the set of support vectors is configured to predict a target type from the parameters with a characterization confidence of at least 80%.

In one embodiment, the system further comprises a non-transitory computer-readable medium with instructions stored thereon, that when executed by a processor, perform the steps of obtaining a set of calculated support vectors to form a classification scheme, obtaining a set of at least one input image of an object, the at least one input image having an associated applied force value, selecting a subset of the set of at least one input image having an associated applied force value above a threshold, performing a principal component analysis on the subset of input images to calculate a set of parameters of each image in the subset, and applying the classification scheme to the set of parameters to classify the object.

In another aspect, a four-dimensional tactile sensor device comprises an elastomer attached to a support plate, a camera positioned proximate to the support plate, and opposite the elastomer, and at least one light source positioned proximate to the support plate and the camera, and opposite the elastomer.

In one embodiment, the at least one light source is positioned at an oblique angle to the support plate. In one embodiment, the at least one light source comprises a light emitting diode. In one embodiment, the at least one light source comprises a fiberoptic cable. In one embodiment, the at least one light source comprises a first light source of a first color, a second light source of a second color, and a third light source of a third color. In one embodiment, the first color is green, the second color is red, and the third color is blue.

In one embodiment, the elastomer comprises Polydimethylsiloxane (PDMS) or silicone. In one embodiment, the elastomer has a thickness of 0.1 mm to 10 mm. In one embodiment, the elastomer has a hardness of 00-0 to 00-80 or A-10 to A-55. In one embodiment, the elastomer is softer than an object to be measured.

In one embodiment, the support plate comprises a transparent material. In one embodiment, the support plate comprises clear methyl methacrylate. In one embodiment, the support plate has a thickness of 0.1 mm to 10 mm. In one embodiment, the device is configured to measure a four-dimensional morphology of an object comprising a three-dimensional shape of and a stiffness of the object. In one embodiment, the device further comprises a least one marker. In one embodiment, the device further comprises a reflective coating on the surface of the elastomer opposite the support plate.

In another aspect, a four-dimensional tactile morphology method comprises providing at least one tactile sensor device, pressing the at least one tactile sensor device against an object to be measured, and calculating a four-dimensional morphology of the measured object.

In one embodiment, the at least one tactile sensor device comprises an elastomer attached to a support plate, a camera positioned proximate to the support plate, and opposite the elastomer, and at least one light source positioned proximate to the support plate and the camera, and opposite the elastomer.

In one embodiment, the four-dimensional morphology is calculated based on an observation by the camera of a deformation of the elastomer. In one embodiment, the at least one light source is configured to highlight the deformation of the elastomer. In one embodiment, the at least one tactile sensor device is positioned on an exterior surface of a housing. In one embodiment, the four-dimensional morphology of the object comprises a three-dimensional shape of and a stiffness of the object. In one embodiment, the measured object comprises at least one of a tumor, a cancer polyp, and a lesion. In one embodiment, the method further comprises identifying a tumor classification based on the four-dimensional morphology.

In one embodiment, the four-dimensional morphology is calculated using a machine learning or artificial intelligence algorithm. In one embodiment, the machine learning algorithm comprises a convolutional neural network.

In one embodiment, the machine learning or artificial intelligence algorithm is trained via a method comprising acquiring a set of input images, each input image having an associated known target type and an applied force, performing a principal component analysis on the set of input images to calculate a set of parameters for each image of the set of input images, providing the sets of parameters to a support vector machine to calculate a set of support vectors to classify the parameters, and selecting a subset of the set of support vectors and an applied force threshold, such that for images having an applied force above the applied force threshold, the set of support vectors is configured to predict a target type from the parameters with a characterization confidence of at least 80%. In one embodiment, the set of input images comprises interval displacement input images and force interval input images.

In another aspect, a four-dimensional tactile sensing system comprises a flexible sleeve, and at least one tactile sensor device positioned on an exterior surface of the flexible sleeve, comprising an elastomer attached to a support plate, a camera positioned proximate to the support plate, and opposite the elastomer, and at least one light source positioned proximate to the support plate and the camera, and opposite the elastomer.

In another aspect, a method of fabricating the elastomer comprises mixing a multi-part elastomer at a desired mass ratio, molding the elastomer mixture in a mold to form the elastomer, removing the elastomer from the mold, spraying a reflective coating onto the elastomer, and pouring a thin protective coating over the reflective coating.

In one embodiment, the mold is coated to prevent adhesion to the elastomer mixture and to ensure a high elastomer surface quality after molding. In one embodiment, the mold is coated with Ease 200. In one embodiment, the step of molding the elastomer mixture comprises pouring the elastomer mixture into the mold, degassing the mixture in a vacuum chamber, and curing the mixture in a curing station. In one embodiment, the reflective coating has a thickness of 1 μm to 500 μm and comprises a silver coating, a chromium coating, a spray on coating, a specialty mirror effect spray paint, a liquid metal, gallium, or mercury. In one embodiment, the thin protective coating comprises a silicone mixture. In one embodiment, the elastomer has a hardness of 00-18.

In another aspect, an elastomer composition comprises a substrate of Polydimethylsiloxane (PDMS) or silicone, and a reflective coating on a surface of the substrate.

In one embodiment, the elastomer composition has a hardness of 00-0 to 00-80 or A-10 to A-55. In one embodiment, the elastomer composition has a hardness of 00-18. In one embodiment, the reflective coating has a thickness of 1 μm to 500 μm and comprises a silver coating, a chromium coating, a spray on coating, a specialty mirror effect spray paint, a liquid metal, gallium, or mercury. In one embodiment, the substrate further comprises a two part Polydimethylsiloxane (PDMS) or a two part silicone mixture combined with a phenyl trimethicone softener mixed at a mass ratio of 14:10:4.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which:

FIG. 12 is a table showing details of the properties of the phantom test bed in accordance with some embodiments.

DETAILED DESCRIPTION OF THE INVENTION

Figure 1:
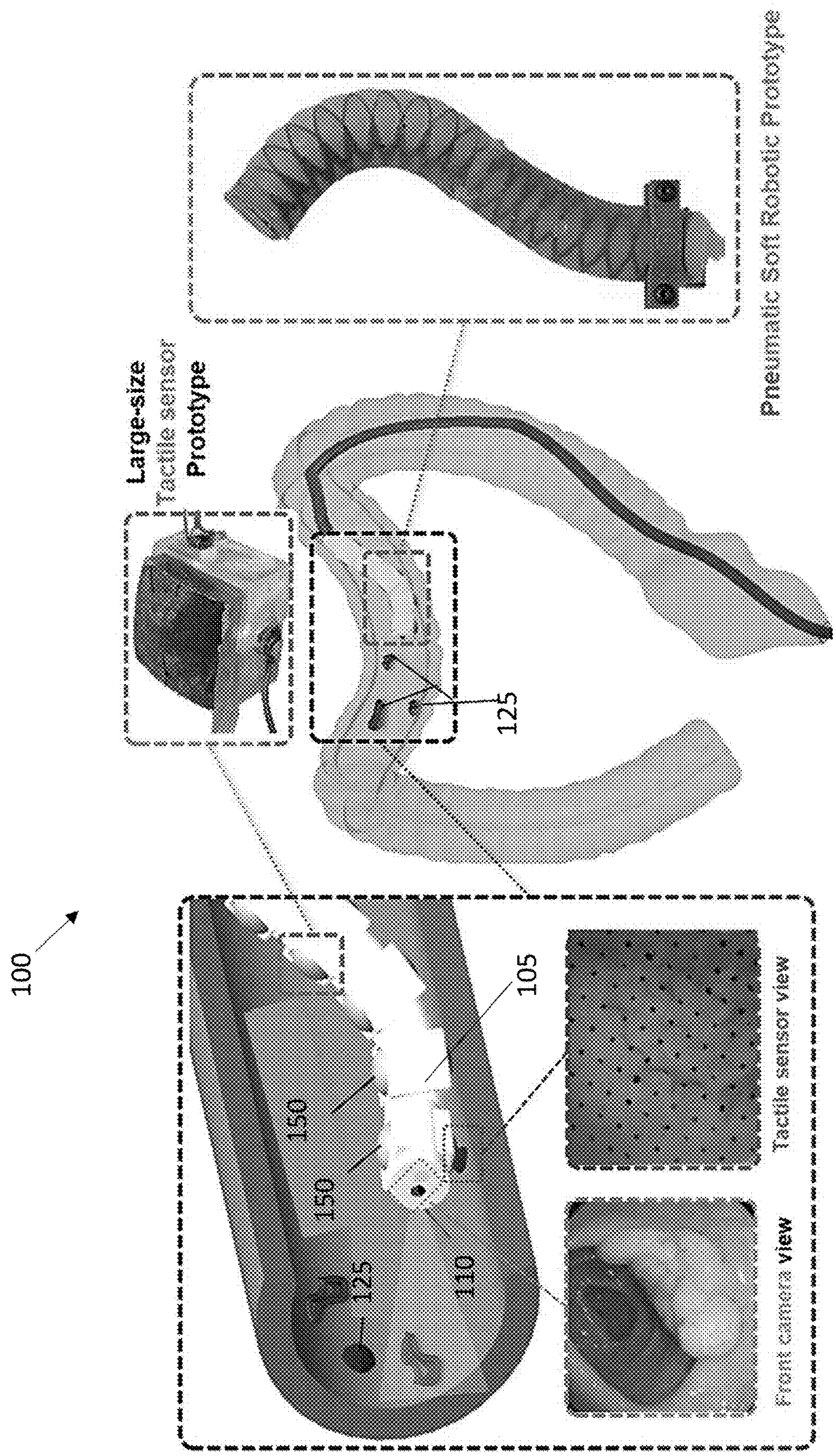
FIG. 1 depicts an exemplary tactile sensing system in accordance with some embodiments.

It is to be understood that the figures and descriptions of the present invention have been simplified to illustrate elements that are relevant for a clearer comprehension of the present invention, while eliminating, for the purpose of clarity, many other elements found in systems and methods of tactile sensing. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Ranges: throughout this disclosure, various aspects of the invention can be presented in a range format. It should be understood that the description in range format is merely for convenience and brevity and should not be construed as an inflexible limitation on the scope of the invention. Where appropriate, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Referring now in detail to the drawings, in which like reference numerals indicate like parts or elements throughout the several views, in various embodiments, presented herein is a tactile sensing system, device and method.

FIG. 1 shows a tactile sensing system 100 in accordance with some embodiments. In some embodiments, the system 100 comprises a housing 105 including a front facing camera 110. The front-facing camera 110 can be used to guide the position of the housing 105. In some embodiments, the system 100 further comprises at least one tactile sensor device 150 positioned on the exterior surface of the housing 105. In some embodiments, the at least one tactile sensor device 150 comprises a skin on the exterior surface of the housing 105. Any suitable number of tactile sensor devices 150, spacing between the devices 150, and arrangement of the devices 150 can be utilized. In some embodiments, the tactile sensor devices 150 can be arranged linearly, annularly, spirally, geometrically, or in any other suitable arrangement or combination thereof. In some embodiments, the center to center spacing of the tactile sensor devices 150 is 5 mm to 100 mm. The tactile sensor device 150 can be utilized to measure fine textural details, size, shape and stiffness an object of interest 125. In some embodiments, the object of interest 125 can be a polyp or lesion. In some embodiments, the housing 105 comprises a soft robot, a hard robot, a flexible robot, an endoscope, a colonoscope, a probe, a catheter, or any other suitable housing or combination thereof. In some embodiments, the housing 105 comprises a pneumatically controlled soft robot. In some embodiments, the housing 105 comprises a cable controlled soft robot. In some embodiments, the tactile sensing device 150 is configured to detect texture-based features.

In some embodiments, the system 100 can provide haptic feedback. In some embodiments, the system 100 can map the 3D shape and stiffness of small features of a measured object 125, up to 100 μm. In some embodiments, the system 100 can be utilized to create a topological mapping of internal anatomies and create high resolution detailed mapping of the internal surface of internal anatomies such as the colon or stomach, for example. In some embodiments the tactile sensing device 150 can have a normal displacement via a pneumatic actuation to provide normal interaction forces for texture and stiffness measurement, wherein only tactile sensing device 150 is displaced rather than the whole robot 105. In some embodiments, actuation of the embedded tactile sensing device 150 can be performed via a cable actuator and/or a pneumatic actuator configured to move the tactile sensing robot system 100. In some embodiments, actuation of the embedded tactile sensing device 150 can be performed via a cable actuator and/or a pneumatic actuator configured to move the embedded tactile sensing device 150 independently of the tactile sensing robot system 100.

Figure 2:
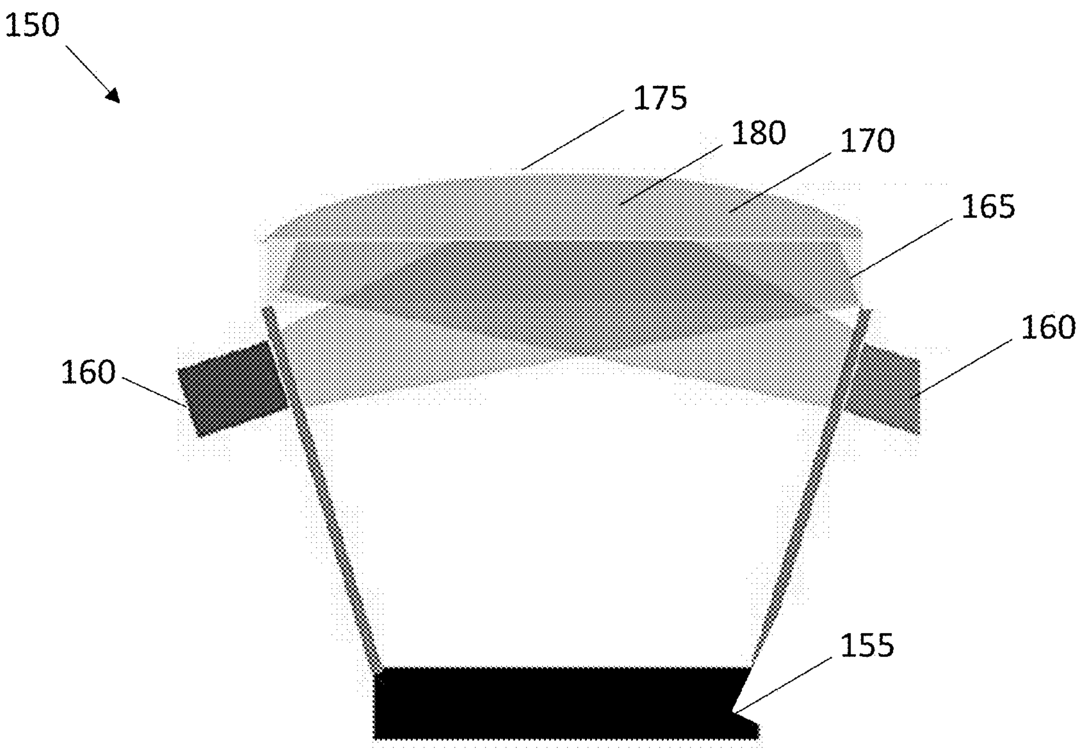
FIG. 2 depicts an exemplary tactile sensor device in accordance with some embodiments.

Referring now to FIG. 2, an exemplary tactile sensor device 150 is depicted. In some embodiments, the tactile sensor device 150 comprises an elastomer 170 attached to a support plate 165, a camera 155 positioned proximate to the support plate 165 and opposite the elastomer 170, and at least one light source 160 positioned proximate to the support plate 165 and the camera 155, and opposite the elastomer 170. In some embodiments the device 150 is vision based. In some embodiments, the elastomer stiffness is adjusted dependent on the application. In some embodiments, the support plate 165 is rigid. In some embodiments, the support plate 165 is flexible. In some embodiments, a plurality of cameras 155 are included. In some embodiments, the camera 155 comprises a fiberoptic camera, wherein the fiberoptic portion is positioned proximate to the support plate 165 and opposite the elastomer 170. In some embodiments, the camera 155 is a wireless camera. In some embodiments, the camera 155 has a size greater than or equal to 1 mm. In some embodiments, the at least one light source 160 is positioned at an oblique angle to the support plate 165. In some embodiments, the at least one light source 160 comprises at least one of a light emitting diode (LED), a fiberoptic cable, and any other suitable light source or combination thereof. In some embodiments, the light source 160 is configured to provide at least one of visible light, ultraviolet (UV) light, infrared (IR) light, and any other suitable light or combination thereof. In some embodiments, the device 150 is configured to measure a four-dimensional morphology of an object 125 comprising the three-dimensional shape of and the stiffness of the object in a radiation free manor.

In some embodiments, the at least one light source 160 comprises a first light source of a first color, a second light source of a second color, and a third light source of a third color. In some embodiments, the first color is green, the second color is red, and the third color is blue, but any suitable number and combination of colors can be utilized. In some embodiments, the first, second and third colors each comprise at least one of visible light, ultraviolet (UV) light, infrared (IR) light, and any other suitable light or combination thereof. The at least one light source 160 can be configured to simultaneously illuminate the tactile sensor device 150 or can be programmed to provide application dependent illumination where a subset of the at least one light source 160 is used to illuminate the tactile sensor device 150 for a set amount of time.

In some embodiments, the elastomer 170 comprises Polydimethylsiloxane (PDMS), silicone, or any type of flexible elastomer, has a thickness of 0.1 mm to 10 mm, and has a hardness of 00-0 to 00-80 or A-10 to A-55. In some embodiments, the elastomer 170 is softer than an object to be measured 125.

In some embodiments, the support plate 165 comprises a transparent material. In some embodiments, the support plate comprises clear methyl methacrylate plate (acrylic plate) or any other suitable material, and has a thickness of 0.1 mm to 10 mm.

In some embodiments, the device 150 further includes a reflective coating 175 on a surface of the elastomer 170, such as the surface opposite the support plate 165. In some embodiments, the reflective coating 175 is configured to enhance light collection. In some embodiments, the reflective coating 175 is used to create a mirror effect. In some embodiments, the reflective coating 175 comprises a silver coating, a chromium coating, a spray on coating, a specialty mirror effect spray paint, a liquid metal such as gallium or mercury, or any suitable reflective coating or combination thereof. In some embodiments, the reflective coating 175 has a thickness of 1 μm to 500 μm or any other suitable thickness.

In some embodiments, the device 150 further includes at least one marker on a surface of and/or within the elastomer 170. In some embodiments, the at least one marker 180 is configured for use as a reference mark for vision-based calculations of properties of a sample being measured with the device 150 such as stiffness, size, and shape, for example.

Figure 3:
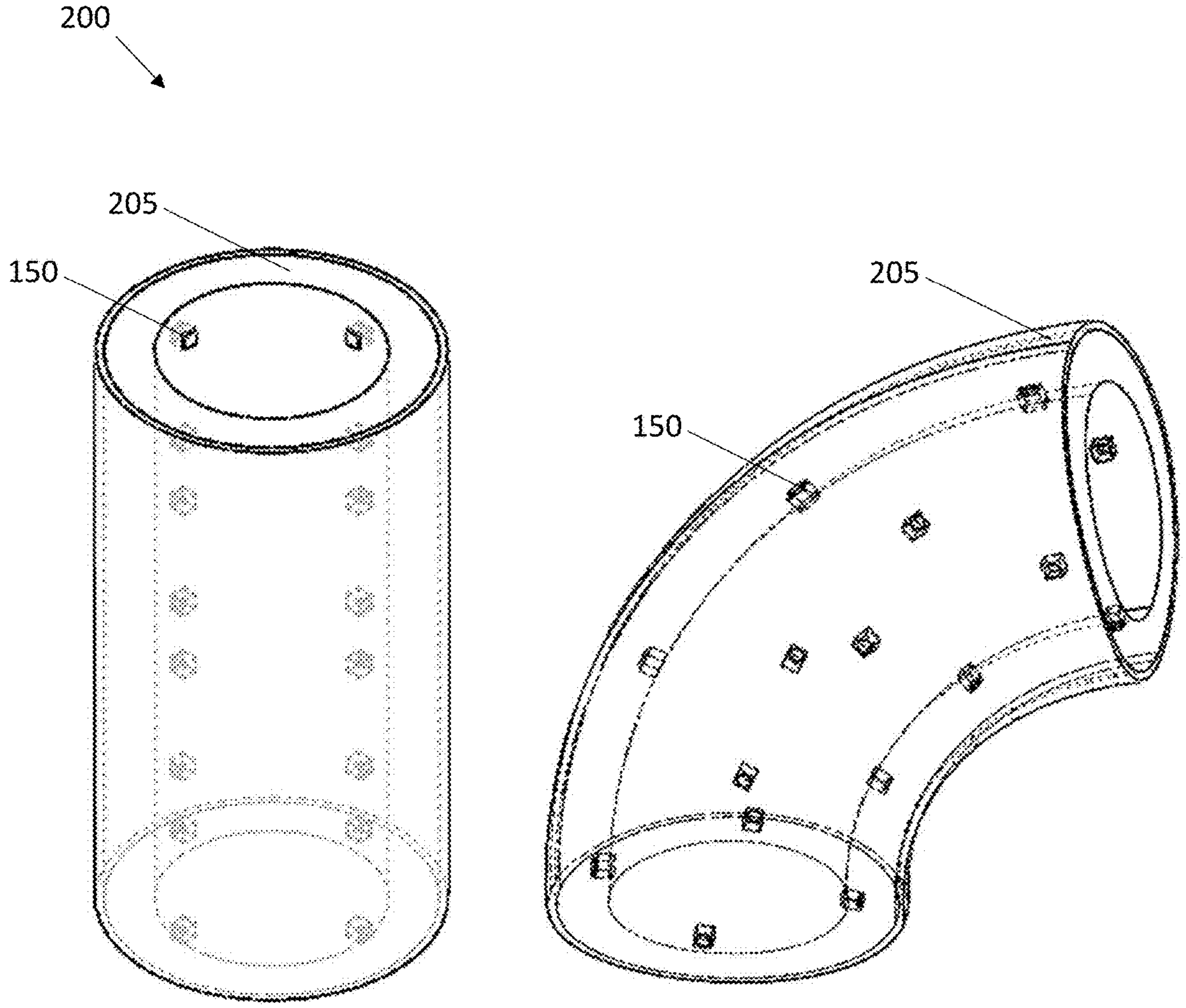
FIG. 3 depicts an exemplary tactile sensing system in accordance with some embodiments.

FIG. 3 shows a tactile sensing system 200 in accordance with some embodiments. In some embodiments, the tactile sensing system 200 comprises a flexible sleeve and at least one tactile sensor device positioned on an exterior surface of the flexible sleeve. In some embodiments, the sleeve 205 is permanently connected to the exterior surface of a device such as, for example, a soft robot, a hard robot, a flexible robot, an endoscope, a colonoscope, a probe, a catheter, or any other suitable device or combination thereof. In some embodiments, the sleeve 205 is removably connected to the exterior surface of a device such as, for example, a soft robot, a hard robot, a flexible robot, an endoscope, a colonoscope, a probe, a catheter, or any other suitable device or combination thereof. In some embodiments the sleeve 205 comprises Polydimethylsiloxane (PDMS), silicone, or any other suitable type of flexible elastomer or combination thereof. In some embodiments, the sleeve 205 generally has a hollow cylindrical shape including a cavity configured to accept a device such as, for example, a soft robot, a hard robot, a flexible robot, an endoscope, a colonoscope, a probe, a catheter, or any other suitable device or combination thereof. In some embodiments, the sleeve 205 has an outer diameter of 1 mm to 25 mm, an inner diameter of 0.8 mm to 24.8 mm, and a length of 10 mm to 500 mm. In some embodiments, the sleeve 205 material is configured as the elastomer 170 of the tactile sensor device 150.

Any suitable number of tactile sensor devices 150, spacing between the devices 150, and arrangement of the devices 150 can be utilized. In some embodiments, the tactile sensor devices 150 can be arranged linearly, annularly, spirally, geometrically, or in any other suitable arrangement or combination thereof. In some embodiments, the center to center spacing of the tactile sensor devices 150 is 5 mm to 100 mm. The tactile sensor device 150 can be utilized to measure fine textural details, size, shape and stiffness an object of interest. In some embodiments, the object of interest can be a polyp or lesion. In some embodiments, the tactile sensing device 150 is configured to detect texture-based features.

In some embodiments, the system 200 can provide haptic feedback. In some embodiments, the system 200 can map the 3D shape and stiffness of small features of a measured object, up to 100 μm. In some embodiments, the system 200 can be utilized to create a topological mapping of internal anatomies and create high resolution detailed mapping of the internal surface of internal anatomies such as the colon or stomach, for example.

Figure 4:
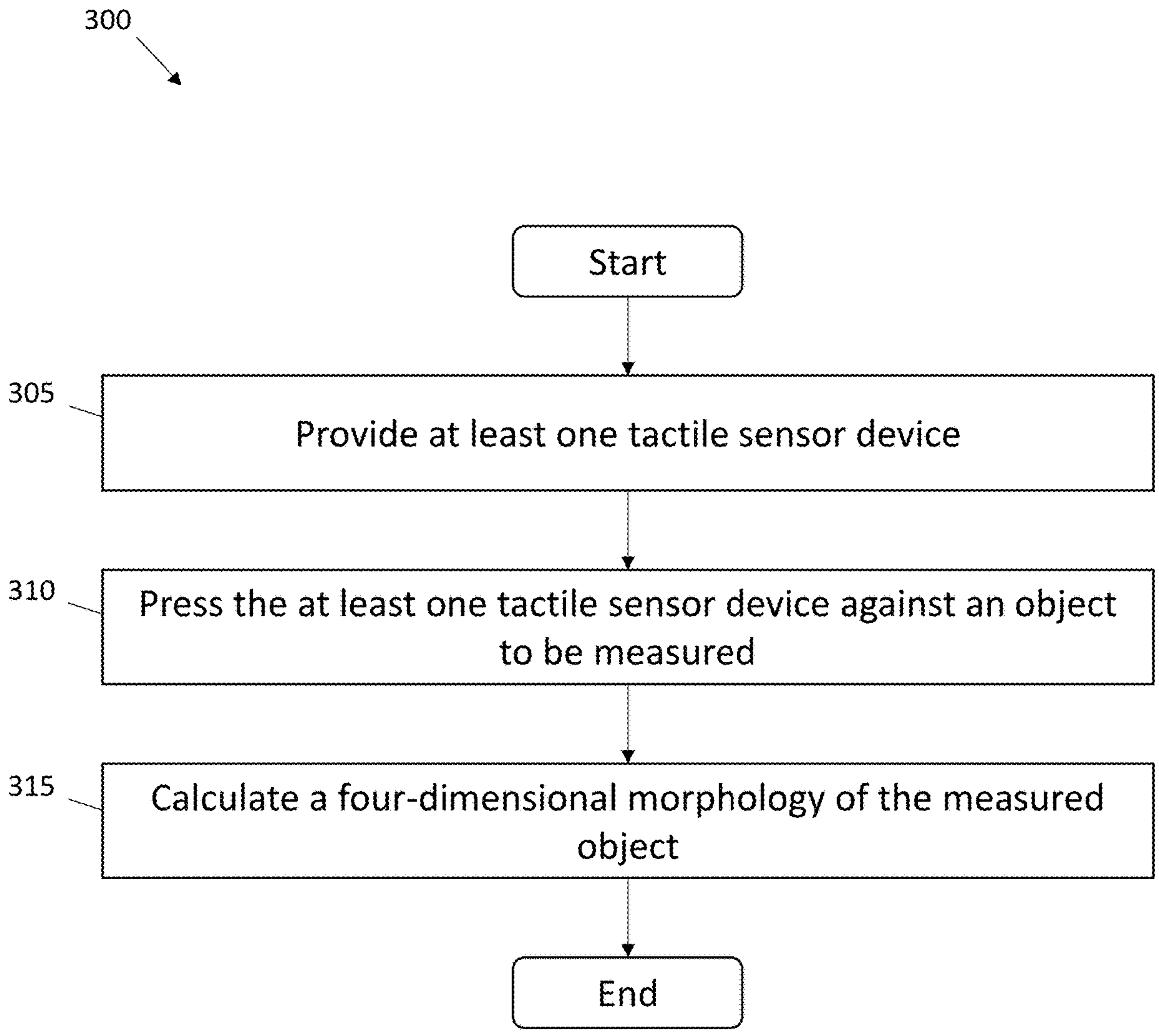
FIG. 4 is a flow chart depicting an exemplary tactile morphology method in accordance with some embodiments.

FIG. 4 is a flow chart showing an exemplary tactile morphology method 300. The method 300 starts at Operation 305 where at least one tactile sensor device 150 is provided. In some embodiments, the tactile sensor device 150 comprises an elastomer 170 attached to a support plate 165, a camera 155 positioned proximate to the support plate 165 and opposite the elastomer 170, and at least one light source 160 positioned proximate to the support plate 165 and the camera 155, and opposite the elastomer 170. In some embodiments, the at least one light source 160 is positioned at an oblique angle to the support plate 165. In some embodiments, the at least one light source 160 comprises at least one of a light emitting diode (LED), a fiberoptic cable, and any other suitable light source or combination thereof. In some embodiments, the at least one tactile sensor device 150 is positioned on the exterior surface of a housing 105.

At Operation 310, the at least one tactile sensor device 150 is pressed against an object to be measured 125. As the device 150 is pressed against the object to be measured 125, the elastomer 170 is deformed.

The method ends at Operation 315, where a four-dimensional morphology of the measured object 125 is calculated. The four-dimensional morphology is calculated based on an observation by the camera 155 of a deformation of the elastomer 170. In some embodiments, the four-dimensional morphology of the object 125 comprises the three-dimensional shape of and the stiffness of the object. In some embodiments, the at least one light source 160 is configured to highlight the deformation of the elastomer 170.

In some embodiments, the measured object 125 comprises at least one of a tumor, a cancer polyp, and a lesion. In some embodiments, the method 300 further comprises identifying a tumor classification based on the four-dimensional morphology. In some embodiments, the four-dimensional morphology is calculated using a machine learning algorithm. In some embodiments, the machine learning algorithm comprises a convolutional neural network. In some embodiments, the algorithm is configured to provide real time tumor identification, tumor classification and/or stiffness scoring based on the visual feedback of the tactile sensor device 150.

In some embodiments, the measure object 125 comprises an interior component of a pipe in an industrial or municipal system. For example, the system 100 can be utilized in a pipe inspection setting taking measurements of pipe connection points to look for degradation and/or cracking. In some embodiments, the measured object comprises a fruit. For example, the system 100 can be utilized in a farming application such as harvesting by taking a measurement of the fruit to see if is ripe enough to pick.

In another aspect, a method of fabricating the elastomer comprises mixing a multi-part elastomer at a desired mass ratio, molding the elastomer mixture in a mold to form the elastomer, removing the elastomer from the mold, spraying a reflective coating onto the elastomer, and pouring a thin protective coating over the reflective coating.

In one embodiment, the mold is coated to prevent adhesion to the elastomer mixture and to ensure a high elastomer surface quality after molding. In one embodiment, the mold is coated with Ease 200. In one embodiment, the step of molding the elastomer mixture comprises pouring the elastomer mixture into the mold, degassing the mixture in a vacuum chamber, and curing the mixture in a curing station. In one embodiment, the reflective coating comprises sprayed specialty mirror effect spray paint. In one embodiment, the thin protective coating comprises a silicone mixture. In one embodiment, the elastomer has a hardness of 00-18. In some embodiments, markers are place in or on the elastomer during the molding step.

In some embodiments an elastomer composition comprises a substrate of Polydimethylsiloxane (PDMS) or silicone, and a reflective coating on a surface of the substrate. In one embodiment, the elastomer composition has a hardness of 00-0 to 00-80 or A-10 to A-55. In one embodiment, the elastomer composition has a hardness of 00-18. In one embodiment, the reflective coating has a thickness of 1 μm to 500 μm and comprises a silver coating, a chromium coating, a spray on coating, a specialty mirror effect spray paint, a liquid metal, gallium, or mercury. In one embodiment, the substrate comprises a two part Polydimethylsiloxane (PDMS) or a two part silicone mixture combined with a phenyl trimethicone softener mixed at a mass ratio of 14:10:4.

In some aspects of the present invention, software executing the instructions provided herein may be stored on a non-transitory computer-readable medium, wherein the software performs some or all of the steps of the present invention when executed on a processor.

Aspects of the invention relate to algorithms executed in computer software. Though certain embodiments may be described as written in particular programming languages, or executed on particular operating systems or computing platforms, it is understood that the system and method of the present invention is not limited to any particular computing language, platform, or combination thereof. Software executing the algorithms described herein may be written in any programming language known in the art, compiled or interpreted, including but not limited to C, C++, C#, Objective-C, Java, JavaScript, MATLAB, Python, PHP, Perl, Ruby, or Visual Basic. It is further understood that elements of the present invention may be executed on any acceptable computing platform, including but not limited to a server, a cloud instance, a workstation, a thin client, a mobile device, an embedded microcontroller, a television, or any other suitable computing device known in the art.

Parts of this invention are described as software running on a computing device. Though software described herein may be disclosed as operating on one particular computing device (e.g. a dedicated server or a workstation), it is understood in the art that software is intrinsically portable and that most software running on a dedicated server may also be run, for the purposes of the present invention, on any of a wide range of devices including desktop or mobile devices, laptops, tablets, smartphones, watches, wearable electronics or other wireless digital/cellular phones, televisions, cloud instances, embedded microcontrollers, thin client devices, or any other suitable computing device known in the art.

Similarly, parts of this invention are described as communicating over a variety of wireless or wired computer networks. For the purposes of this invention, the words "network", "networked", and "networking" are understood to encompass wired Ethernet, fiber optic connections, wireless connections including any of the various 802.11 standards, cellular WAN infrastructures such as 3G, 4G/LTE, or 5G networks, Bluetooth®, Bluetooth® Low Energy (BLE) or Zigbee® communication links, or any other method by which one electronic device is capable of communicating with another. In some embodiments, elements of the networked portion of the invention may be implemented over a Virtual Private Network (VPN).

Figure 5:
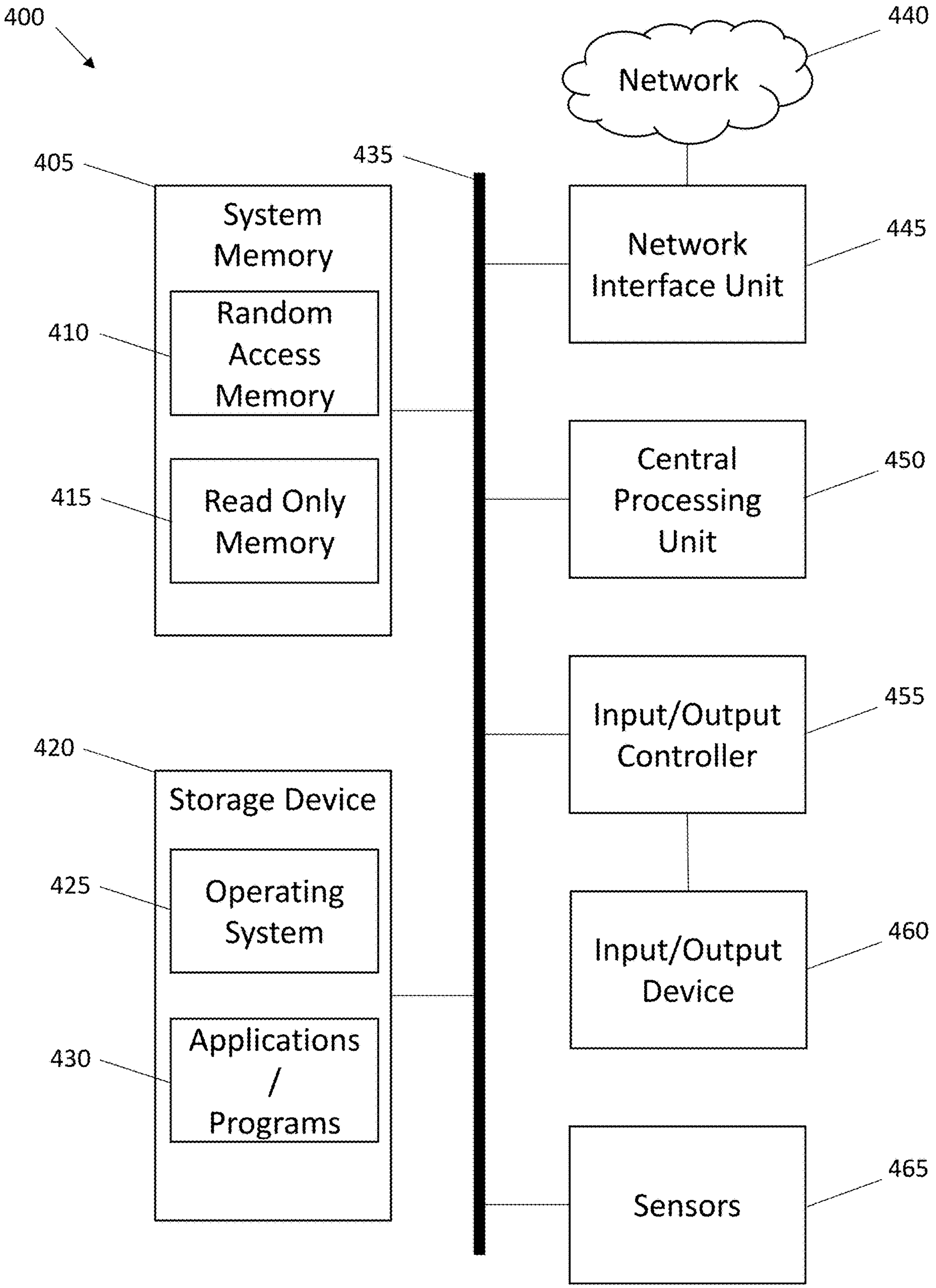
FIG. 5 depicts an exemplary computing system in accordance with some embodiments.

FIG. 5 and the following discussion are intended to provide a brief, general description of a suitable computing environment in which the invention may be implemented. While the invention is described above in the general context of program modules that execute in conjunction with an application program that runs on an operating system on a computer, those skilled in the art will recognize that the invention may also be implemented in combination with other program modules.

Generally, program modules include routines, programs, components, data structures, and other types of structures that perform particular tasks or implement particular abstract data types. Moreover, those skilled in the art will appreciate that the invention may be practiced with other computer system configurations, including hand-held devices, multiprocessor systems, microprocessor-based or programmable consumer electronics, minicomputers, mainframe computers, and the like. The invention may also be practiced in distributed computing environments where tasks are performed by remote processing devices that are linked through a communications network. In a distributed computing environment, program modules may be located in both local and remote memory storage devices.

FIG. 5 depicts an illustrative computer architecture for a computer 400 for practicing the various embodiments of the invention. The computer architecture shown in FIG. 4 illustrates a conventional personal computer, including a central processing unit 450 ("CPU"), a system memory 405, including a random-access memory 410 ("RAM") and a read-only memory ("ROM") 415, and a system bus 435 that couples the system memory 405 to the CPU 450. A basic input/output system containing the basic routines that help to transfer information between elements within the computer, such as during startup, is stored in the ROM 415. The computer 400 further includes a storage device 420 for storing an operating system 425, application/program 430, and data.

The storage device 420 is connected to the CPU 450 through a storage controller (not shown) connected to the bus 435. The storage device 420 and its associated computer-readable media, provide non-volatile storage for the computer 400. Although the description of computer-readable media contained herein refers to a storage device, such as a hard disk or CD-ROM drive, it should be appreciated by those skilled in the art that computer-readable media can be any available media that can be accessed by the computer 400.

By way of example, and not to be limiting, computer-readable media may comprise computer storage media. Computer storage media includes volatile and non-volatile, removable and non-removable media implemented in any method or technology for storage of information such as computer-readable instructions, data structures, program modules or other data. Computer storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information, and which can be accessed by the computer.

According to various embodiments of the invention, the computer 400 may operate in a networked environment using logical connections to remote computers through a network 440, such as TCP/IP network such as the Internet or an intranet. The computer 400 may connect to the network 440 through a network interface unit 445 connected to the bus 435. It should be appreciated that the network interface unit 445 may also be utilized to connect to other types of networks and remote computer systems.

The computer 400 may also include an input/output controller 455 for receiving and processing input from a number of input/output devices 460, including a keyboard, a mouse, a touchscreen, a camera, a microphone, a controller, a joystick, or other type of input device. Similarly, the input/output controller 455 may provide output to a display screen, a printer, a speaker, or other type of output device. The computer 400 can connect to the input/output device 460 via a wired connection including, but not limited to, fiber optic, ethernet, or copper wire or wireless means including, but not limited to, Bluetooth, Near-Field Communication (NFC), infrared, or other suitable wired or wireless connections.

As mentioned briefly above, a number of program modules and data files may be stored in the storage device 420 and RAM 410 of the computer 400, including an operating system 425 suitable for controlling the operation of a networked computer. The storage device 420 and RAM 410 may also store one or more applications/programs 430. In particular, the storage device 420 and RAM 410 may store an application/program 430 for providing a variety of functionalities to a user. For instance, the application/program 430 may comprise many types of programs such as a word processing application, a spreadsheet application, a desktop publishing application, a database application, a gaming application, internet browsing application, electronic mail application, messaging application, and the like. According to an embodiment of the present invention, the application/program 430 comprises a multiple functionality software application for providing word processing functionality, slide presentation functionality, spreadsheet functionality, database functionality and the like.

The computer 400 in some embodiments can include a variety of sensors 465 for monitoring the environment surrounding and the environment internal to the computer 400. These sensors 465 can include a Global Positioning System (GPS) sensor, a photosensitive sensor, a gyroscope, a magnetometer, thermometer, a proximity sensor, an accelerometer, a microphone, biometric sensor, barometer, humidity sensor, radiation sensor, or any other suitable sensor.

In some embodiments, artificial intelligence (AI) and machine learning (ML) methods and algorithms are utilized for performing image recognition, calculation, and classification of the measured objects based on the measured morphology. In some embodiments, the machine learning algorithm comprises a convolutional neural network, or any other suitable machine learning algorithm. In some embodiments, the machine learning or artificial intelligence algorithm is trained via a method comprising acquiring a set of input images, each input image having an associated known target type and an applied force, performing a principal component analysis on the set of input images to calculate a set of parameters for each image of the set of input images, providing the sets of parameters to a support vector machine to calculate a set of support vectors to classify the parameters, and selecting a subset of the set of support vectors and an applied force threshold, such that for images having an applied force above the applied force threshold, the set of support vectors is configured to predict a target type from the parameters with a characterization confidence of at least 80%. In some embodiments, the machine learning or artificial intelligence algorithm calculates the four-dimensional morphology via a method comprising obtaining a set of calculated support vectors to form a classification scheme, obtaining a set of at least one input image of an object, the at least one input image having an associated applied force value selecting a subset of the set of at least one input image having an associated applied force value above a threshold, performing a principal component analysis on the subset of input images to calculate a set of parameters of each image in the subset, and applying the classification scheme to the set of parameters to classify the object.

Experimental Examples

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore specifically point out exemplary embodiments of the present invention and are not to be construed as limiting in any way the remainder of the disclosure.

Figure 6:
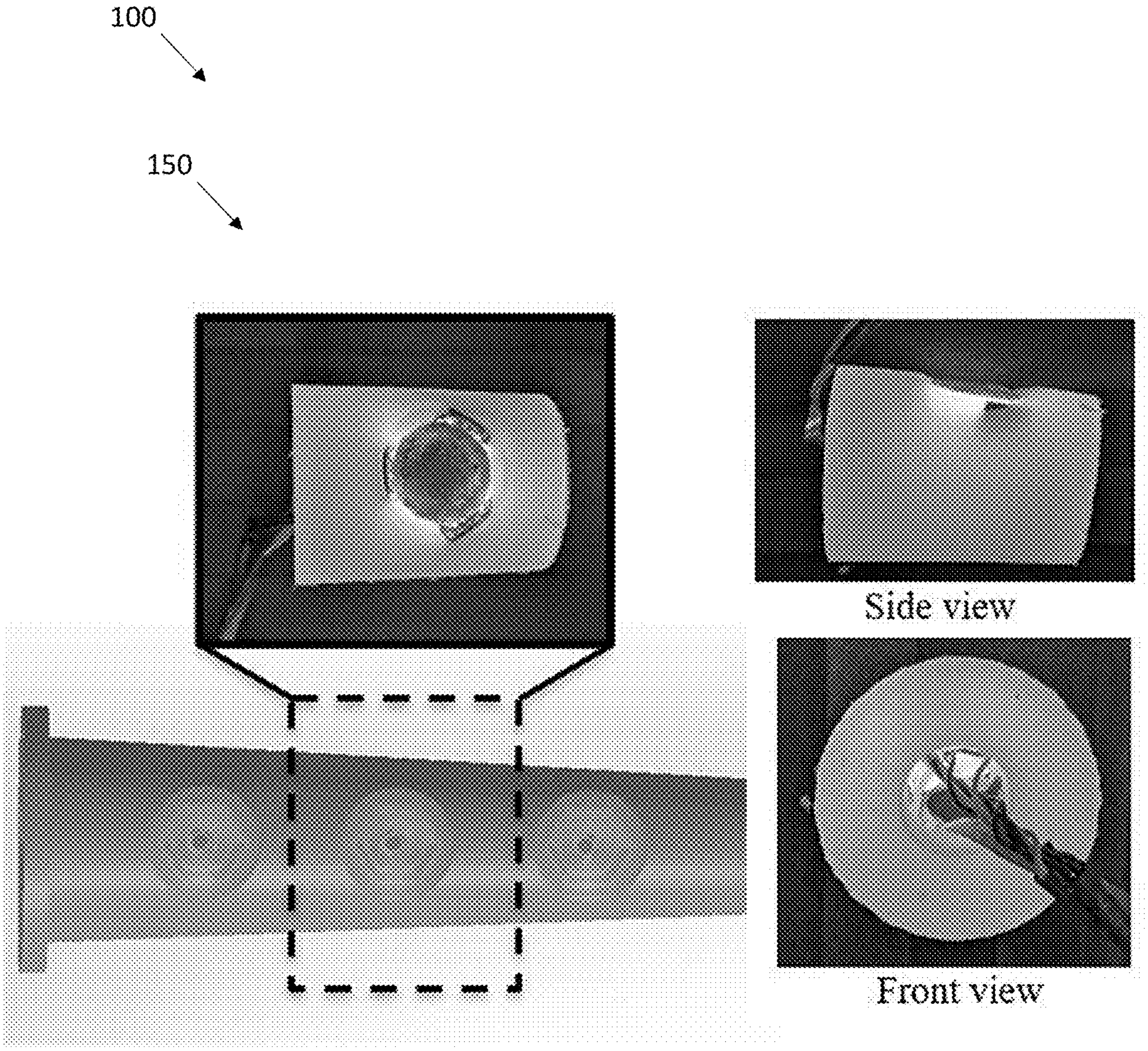
FIG. 6 depicts an exemplary experimental tactile sensor device in accordance with some embodiments.
Figure 7A:
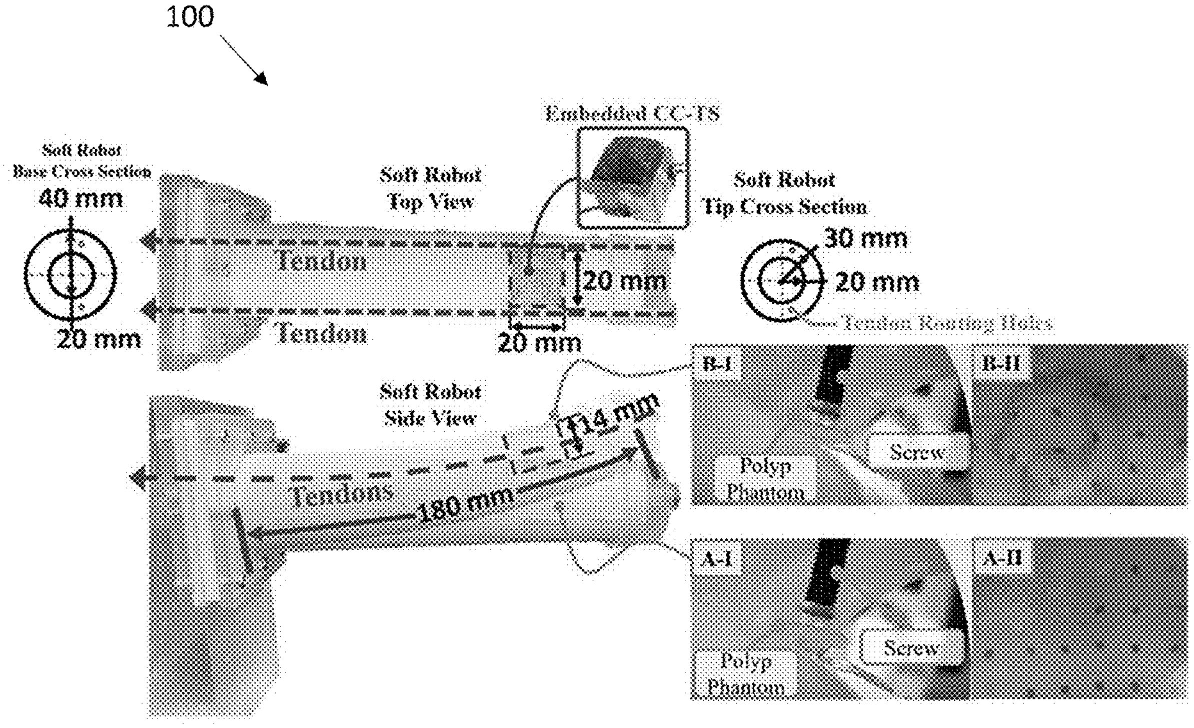
FIGS. 7A and 7B depict exemplary experimental tactile sensing robots in accordance with some embodiments.

FIGS. 6 and 7 show example experimental prototypes of the tactile sensor device 150 and tactile sensing system 100. FIG. 6 shows top, front, and side views of a system 100 with a tactile sensor device 150 including 3 LED light sources 160. The LEDs 160 are place annularly around the sensor camera 155 with 120 degrees between each LED 160. A blue, a red, and a green LED comprise the 3 LED light sources 160. FIG. 7A shows an example experimental embodiment of a soft robot (housing 105) with embedded tactile sensor device 150. The parallel tendons enable the robot to bend towards the sensor 150 and allow direct contact with polyps from various orientations based on the robot's position. The tendon-driven soft robot was designed and fabricated to allow the tactile sensor device 150 to be embedded near the tip of the robot and in the bending plane of the soft robot as shown in FIG. 7A. The base of the robot had an overall diameter of 40 mm and the tip had overall diameter of 30 mm. Silicone (Smooth-Sil 940, Smooth-On, Inc.) with the Young's modulus of E=1.4 MPa was used and poured into a 3-part mold designed to fabricate the robot. Furthermore, the cross-section was left hollow to allow camera signal cables to pass through and reduce the cable tension required to cause bending. To allow the designed sensor to be embedded, a square cut-out was made 28 mm from the robot's tip. Based on the robot's tendon routing, the size of the cutout was limited to 20 mm by 20 mm. Also, tendon driven soft robots often require a single tendon routing through the middle of the bending surface to achieve simple C-shaped planar bending. However, since the tactile sensor device 150 occupies the mid-line of the inner bending surface, it was necessary to have two parallel tendons routing near the bending surface. The tendons were routed symmetrically to cause bending towards the device 150.

Figure 7B:
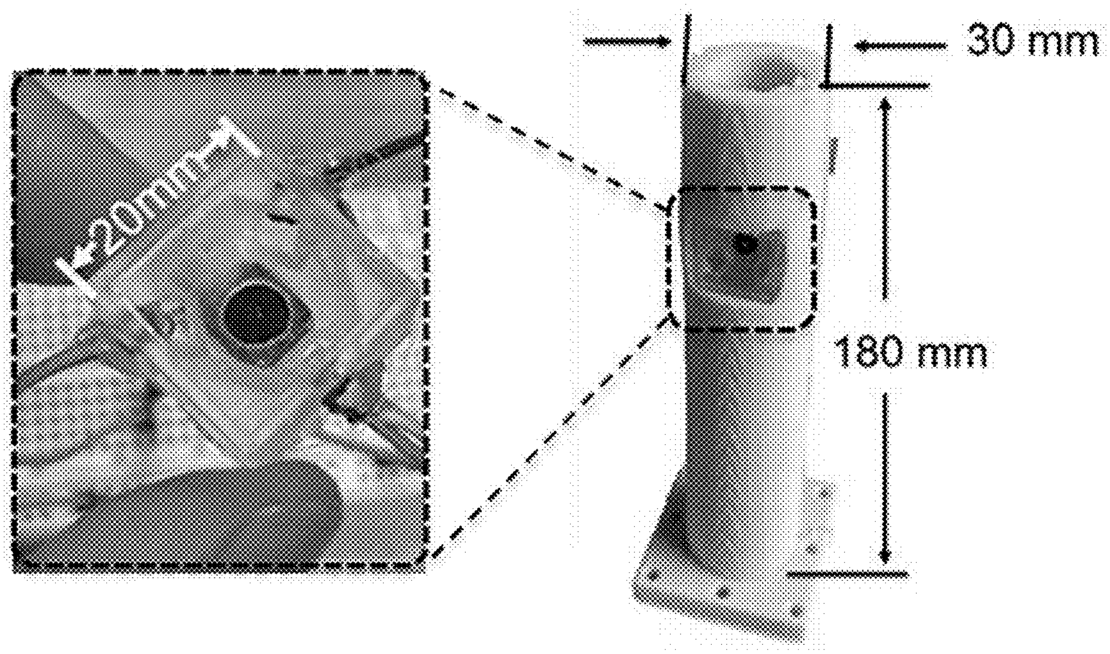

FIG. 7B shows a large-scale prototype of a housing 105 comprising a tactile sensing system 100, including a small prototype of an embedded tactile sensor device 150. In one example prototype, the embedded tactile sensor device 150 had dimensions of 10 mm by 10 mm, which was small enough to fit within the housing 105. This sensor needs to be small enough to be embedded within the soft body of the housing 105 while providing sufficient field of view and resolution for detecting polyps shape, texture, and stiffness. In another prototype, the embedded tactile sensor device 150 has dimensions of 20 mm by 20 mm.

Figure 8A:
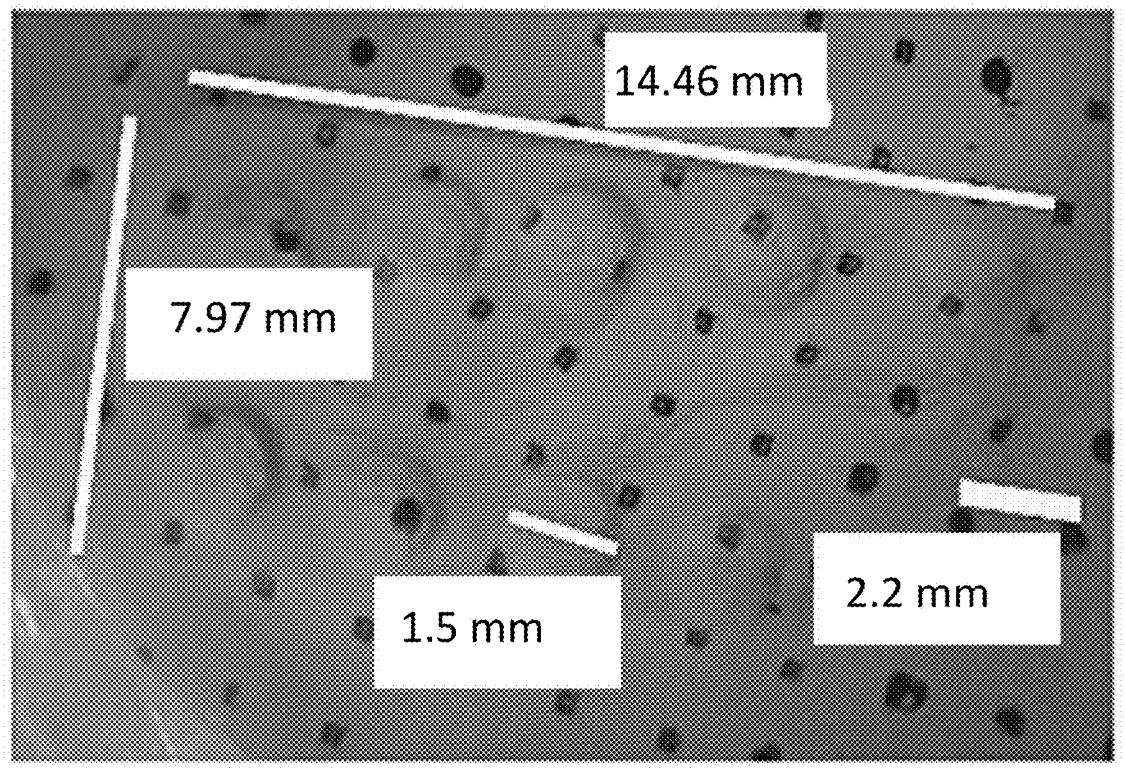
FIGS. 8A and 8B depict exemplary experimental results in accordance with some embodiments.
Figure 8B:
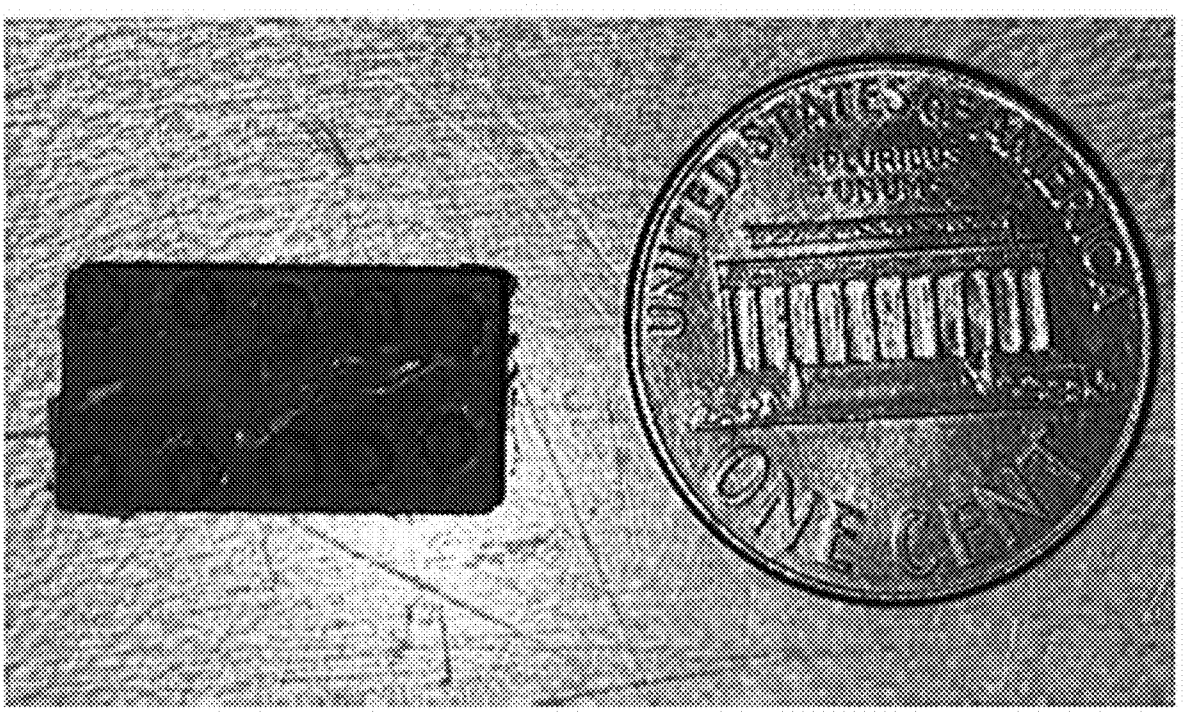

FIGS. 8A and 8B show example experimental result for the system 100. A series of 1.5 mm test polyps according to the Kudo Classification were scaled down by 10× of the original size to test the resolution of the tactile sensor device 150. FIG. 8A shows the sensor output representation of the model, and FIG. 8B shows the actual model next to a US penny for scale. The system 100 can detect small features of the test model including the sizes, types, and features of the polyps.

Figure 9A:
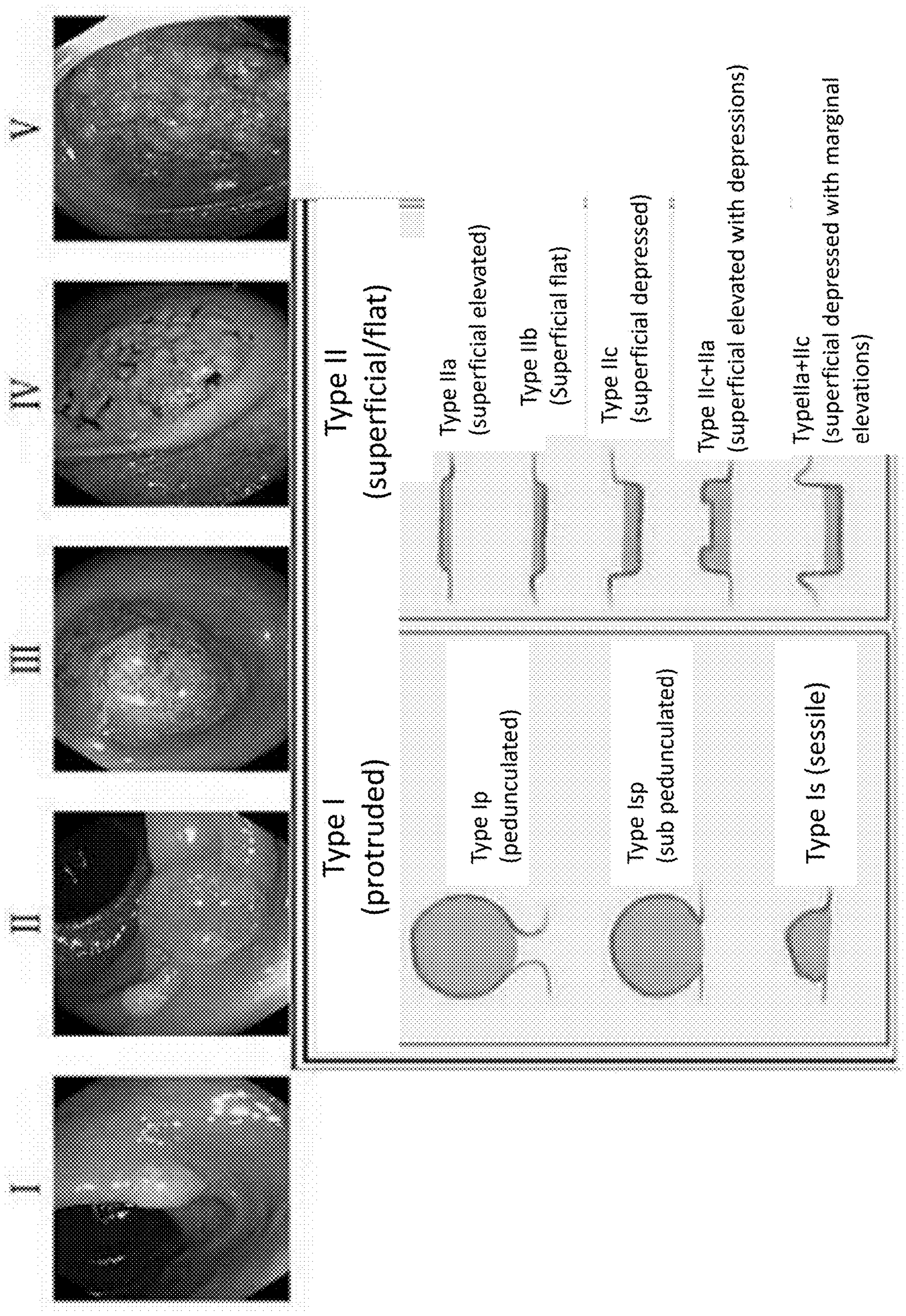
FIGS. 9A and 9B depict exemplary classifications for colorectal polyps in accordance with some embodiments.
Figure 9B:
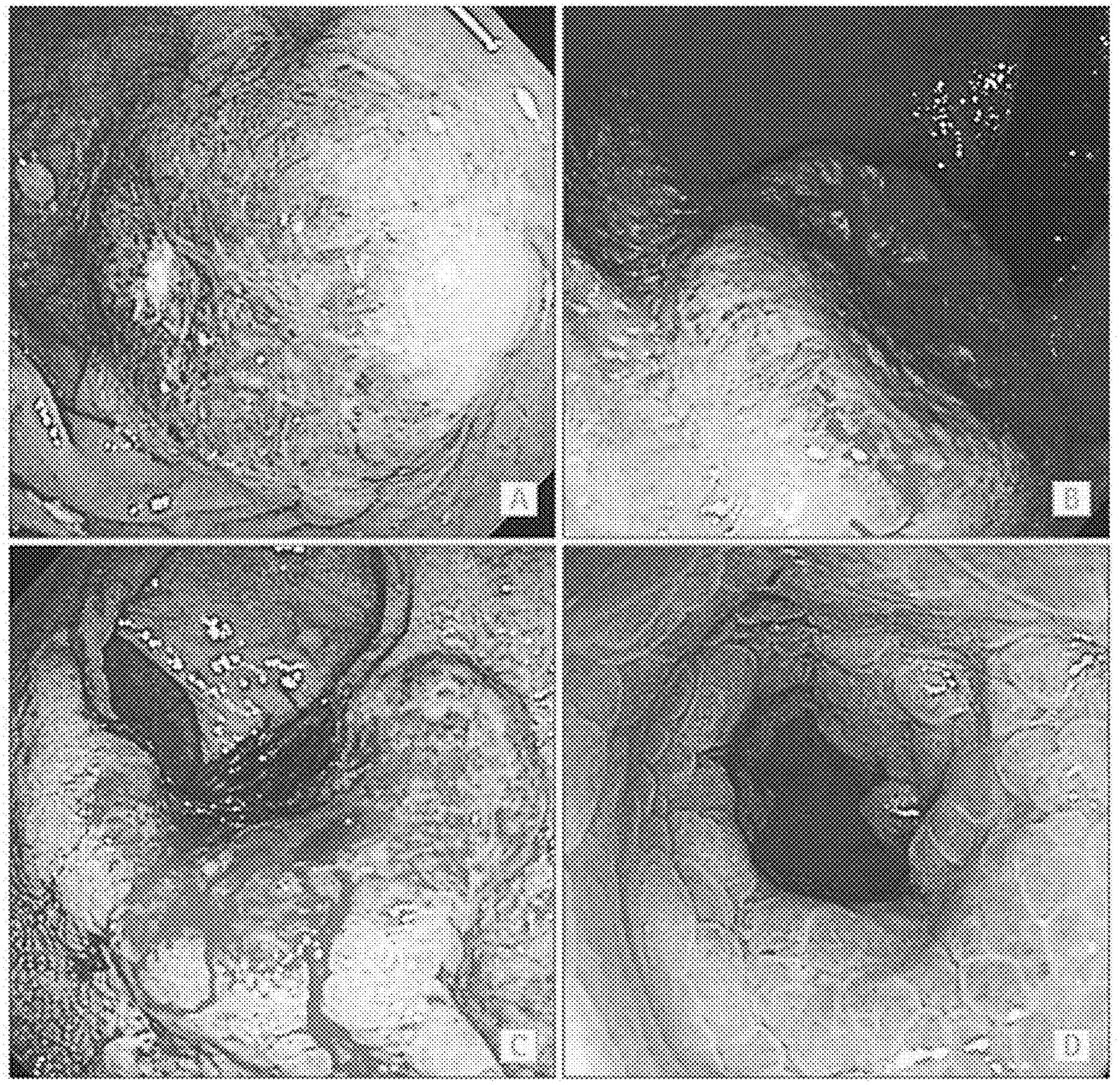

FIGS. 9A and 9B show example polyp classifications. FIG. 9A shows images of colorectal polyps as well as the Paris Classification for tumors based on shape. As shown, type V tumors are classified as cancerous by the Kudo Classification. FIG. 9B shows images of colorectal polyps under the Bormann classification. The system 100 can be utilized to identify and classify tumors based on these classification schemes.

Figure 10:
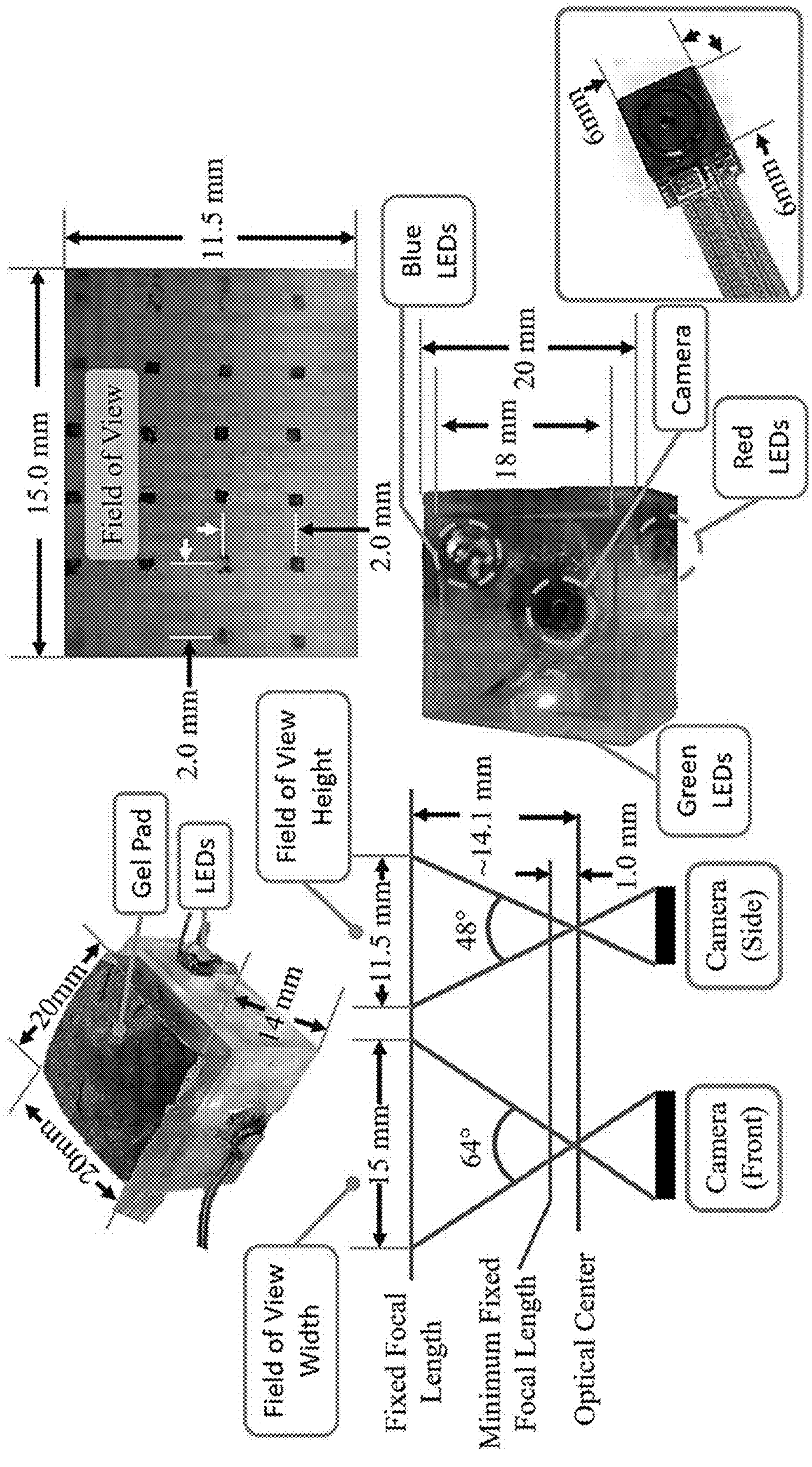
FIG. 10 depicts details of an example experimental tactile sensing device in accordance with some embodiments.

FIGS. 10-18 show example experimental results for the system 100. FIG. 10 shows details of an example experimental tactile sensing device 150. The field of view was optimized to maximize the active sensing area while remaining compact. The elastomer gel layer 170 was fabricated first by mixing the parts A and B of XP-565 Silicone (Silicones, Inc.) with 1:14 ratio by mass respectively. Then phenyl trimethicone (LC1550, Lotioncrafter LLC) was mixed in with the silicone at 1:3 ratio respectively. The mixture was then put into a rectangular mold. After curing, a grid of black dots 2 mm apart from each other was added to the top of the molded gel pad with a water transfer paper. Next, a thin layer of silicone was poured on top to protect the grid. A mixture of the silicone, black pigment paint (Silc Pig Black, Smooth-On, Inc.) and white pigment paint (Silc Pig White, Smooth-On, Inc.) was poured on top to prevent light contamination. An acrylic glass layer is then placed under the gel pad to provide a rigid reference surface and detect deformation. As illustrated in FIG. 10, the fabricated tactile sensor device 150 also had a red LED (LR T64F, OSRAM Opto Semiconductors, Inc.), a blue LED (LB T64G, OSRAM Opto Semiconductors, Inc.) and a green LED (LT T66G, OSRAM Opto Semiconductors, Inc.) facing the gel pad and oriented 120 degrees from each other to illuminate and highlight depth of gel pad deformation.

Since colonoscopic environments are spatially constrained, design optimization is necessary to reduce the size of the tactile sensor device 150 while maximizing the sensorized tactile sensing region to provide a sufficient contact surface (i.e., maximum size of 10 mm×10 mm) between the sensor and polyp's surface. To this end, the required size for the housing body of the tactile sensor device 150 was analyzed as well as angle of view and focal length of camera. Based on the robot geometry and dimensions used for the experiment, the maximum allowable housing body before interfering with tendon routes was calculated as 20 mm by 20 mm. To allow sufficient room for LEDs and wiring, the maximum active sensorized surface was then obtained as 15 mm by 15 mm. The focal length, given angle of view (AOV), determined the field of view. Based on the performed analysis and calculations, a compact camera was selected for the experimental application (Noir Mini Camera, Arducam), which had AOV of 64 by 48 degrees. The field of view of the camera was calculated as a function of focal length from the geometrical relationships of the camera optics. Based on this relationship, the desired focal length was found to be 14.1 mm to achieve the desired field of view (i.e., 15 mm by 11.5 mm) defined by robot's space constraints. In order to embed the sensor within the developed soft robot's body, external geometry of the sensor's housing body was designed such that it fills the considered cut in the soft robot's molded geometry. The sensor was then embedded into the soft robot's body sing a silicone adhesive (Sil-Poxy, SmoothOn, Inc.).

Figure 11:
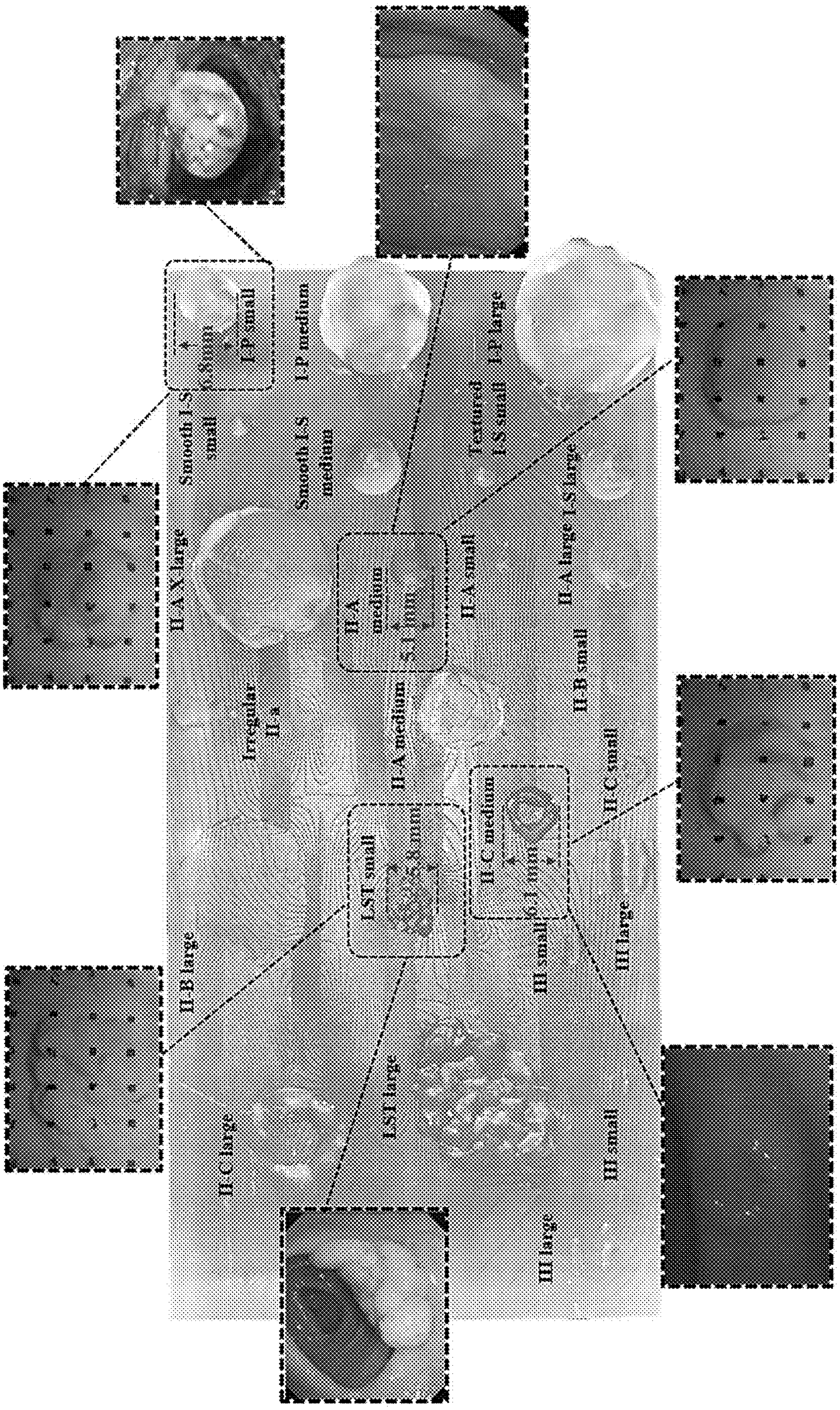
FIG. 11 depicts a realistic high-resolution phantom of various types of colon polyps based on the Kudos classifications that was 3D printed with a rigid material to evaluate the performance of the system in accordance with some embodiments.

FIG. 11 depicts a realistic high-resolution phantom of various types of colon polyps based on the Kudos classifications that was 3D printed with a rigid material to evaluate the performance of the system 100, and FIG. 12 is a table showing details of the properties of the phantom test bed. The inset figures of FIG. 11 show the output of the tactile sensor device 150 and a corresponding real image of four different types of polyps. The texture of the polyps is clearly visible in the output of the tactile sensor device 150.

In contrast to previously presented polyp phantoms in the literature that largely simplified polyp phantoms to generic lumps and simple geometrical structures, the anatomically correct texture and fine details of polyps was replicated. To represent the widely varying polyp classes, a subset including the slightly elevated nonpolypoid polyp (IIa), slightly depressed nonpolypoid polyp (IIc), pedunculated polyp (Ip) and laterally spreading type (LST), were selected for experimentation. Aside from the size and geometry of these polyps, to simulate different stiffnesses for these phantoms, they were fabricated from the following materials and with different high resolution printing technologies (i.e., SLA and Polyjet 3D Printing): Clear Resin (FLGPCL04, Formlabs Inc.), Vero (VeroBlackPlus, Stratasys, Ltd.), Elastic Resin (FLELCL01, Formlabs Inc.) and Tango (TangoBlackPlus, Stratasys, Ltd.). The properties of the polyp phantom's materials are listed in the table of FIG. 12. The polyp phantoms were printed with the compatible 3D printers Form 3 (Formlabs Form 3, Formlabs Inc.) and Digital Anatomy Printer (J750, Stratasys, Ltd).

Figure 13:
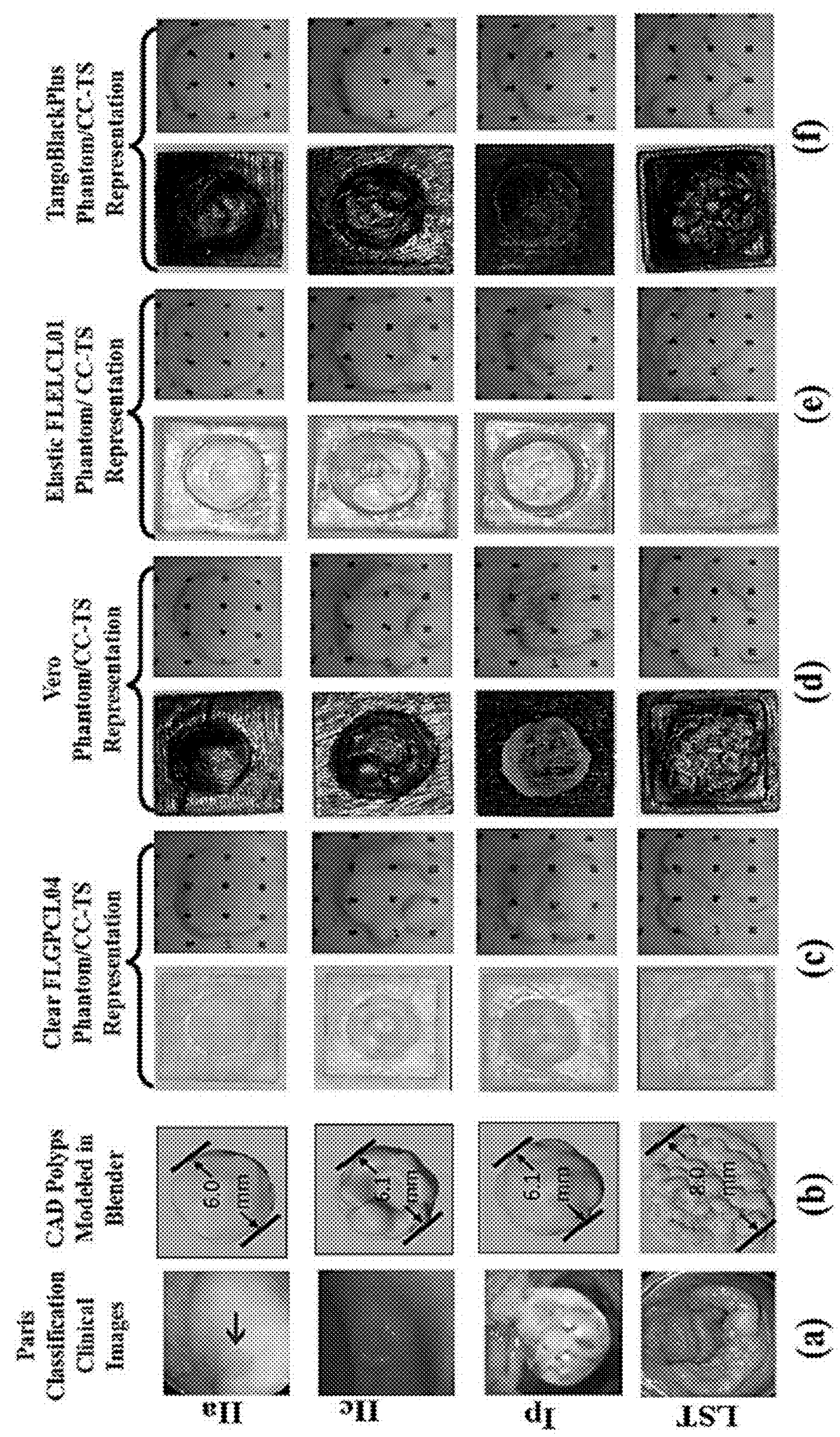
FIG. 13 shows clinical images of the selected polyp types, the CAD designs and their corresponding 3D printed models, as well as their tactile sensor device representation at 3.0 N of applied force in accordance with some embodiments.

The clinical images of the selected polyp types, the CAD designs and their corresponding 3D printed models, as well as their tactile sensor device representation at 3.0 N of applied force are shown in FIG. 13. The IIa type polyp phantom was 6.0 mm in diameter and 1.7 mm in height, the IIc type polyp phantom was 6.1 mm in diameter and 2.39 mm in height, the Ip polyp phantom was 6.1 mm in diameter and 6.06 mm in height, and the LST type polyp phantom was 8.0 mm in diameter and 2.5 mm in height. The polyp phantoms were designed to be modular with threaded ports that allows them to be replaced and positioned easily inside the colon phantom.

Figure 14:
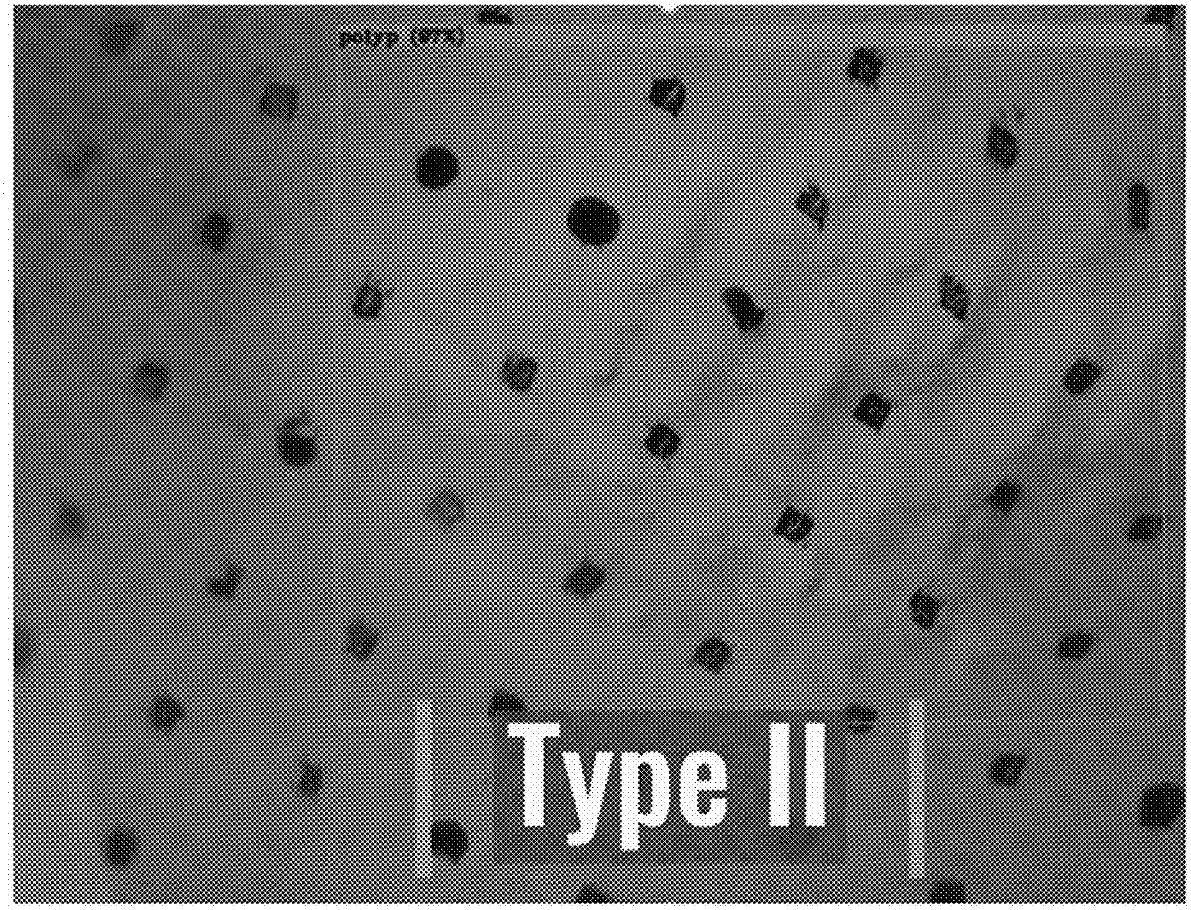
FIG. 14 depicts an example experimental result from an automatic detection of a Type II polyp based on the output of the tactile sensor device 150 in combination with analysis via the machine learning algorithm in accordance with some embodiments.

The result shown in FIG. 14 is from an automatic detection of a Type II polyp based on the output of the tactile sensor device 150 in combination with analysis via the machine learning algorithm. In the example shown, a convolutional neural network was utilized as the machine learning algorithm. The figure clearly shows the high-fidelity and resolution of the device 150 in capturing fine textural features of the printed tumors with different materials. As it can be noted in FIGS. 13 and 14 the device 150 can detect the print layers of J750 Digital Anatomy Printer with the layer height set to 100 μm.

Figure 15A:
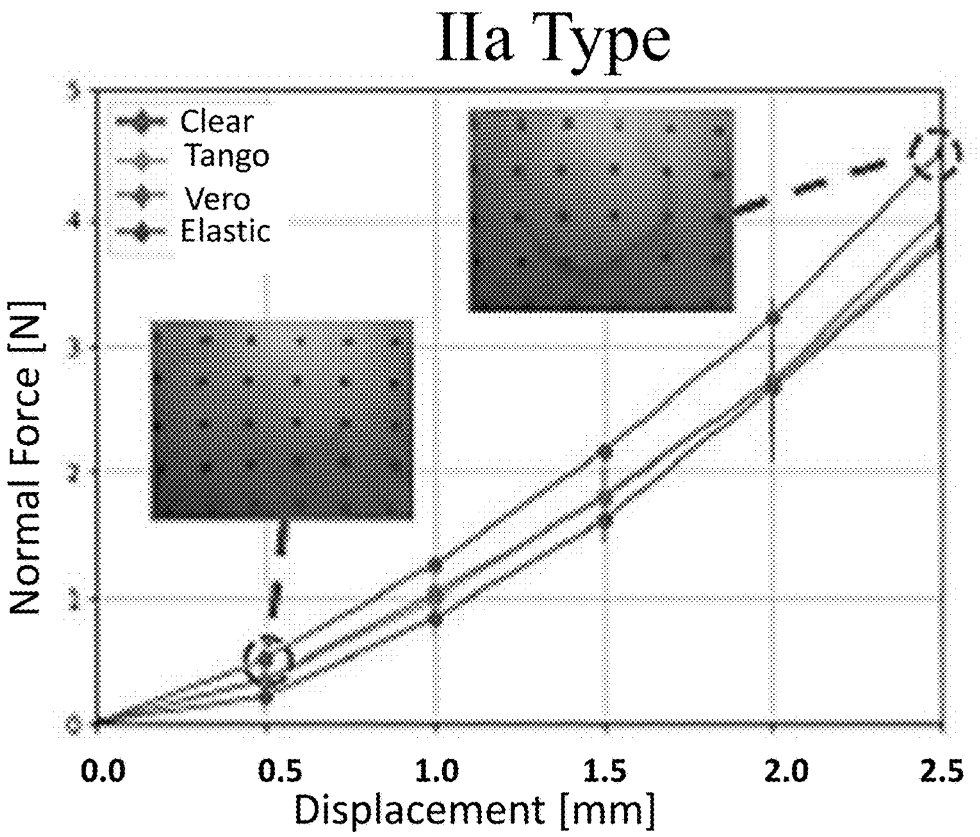
FIGS. 15A and 15B show the experimental results of a displacement versus measured interaction normal force between the system and phantom in accordance with some embodiments.
Figure 15B:
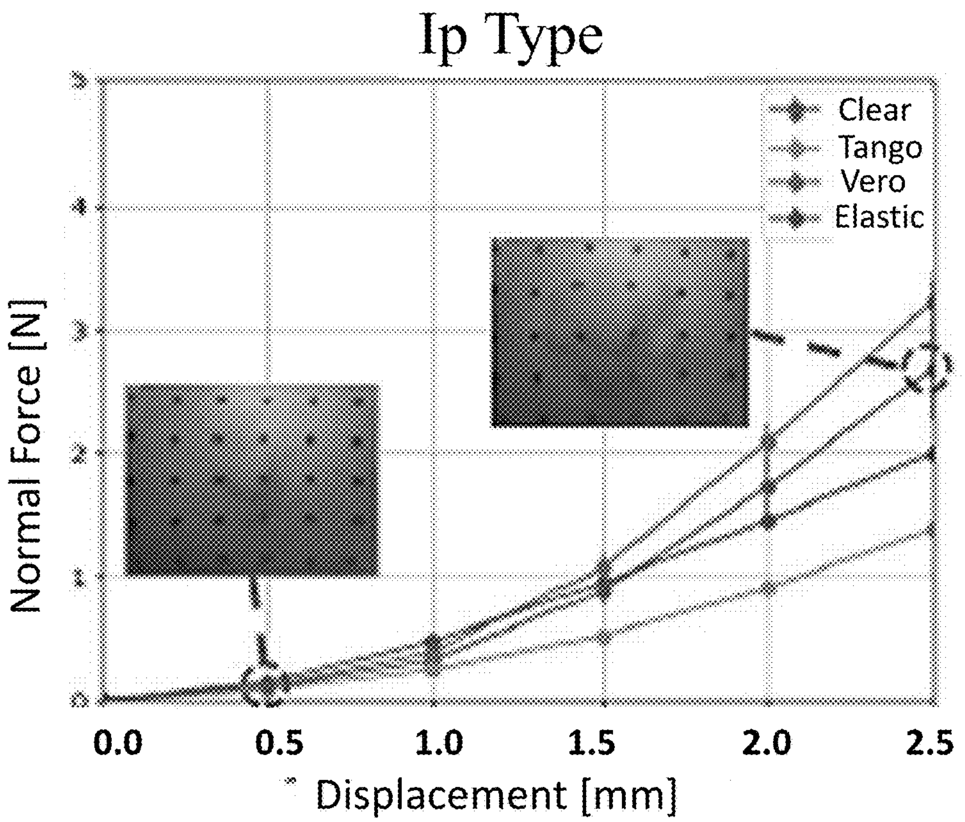
Figure 16A:
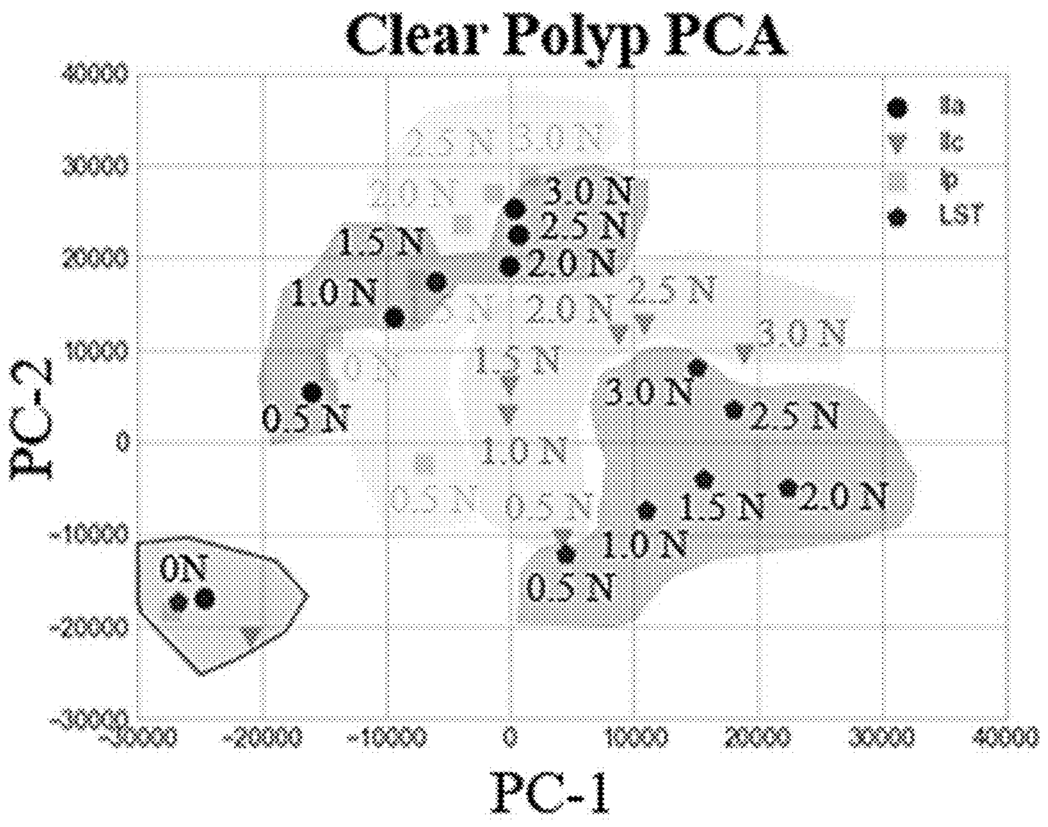
FIGS. 16A through 16D show the first two principal components (i.e., PC-1, PC-2) obtained by PCA analysis on the obtained system images after pushing the polyps with different forces in accordance with some embodiments.
Figure 16B:
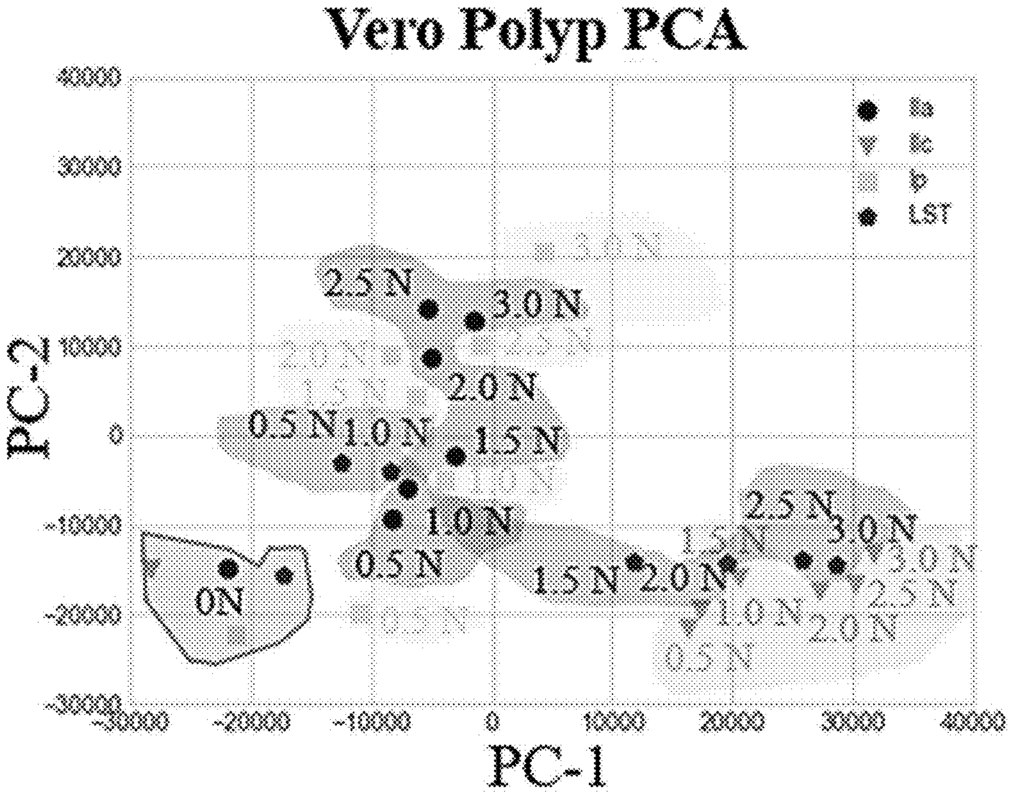
Figure 16C:
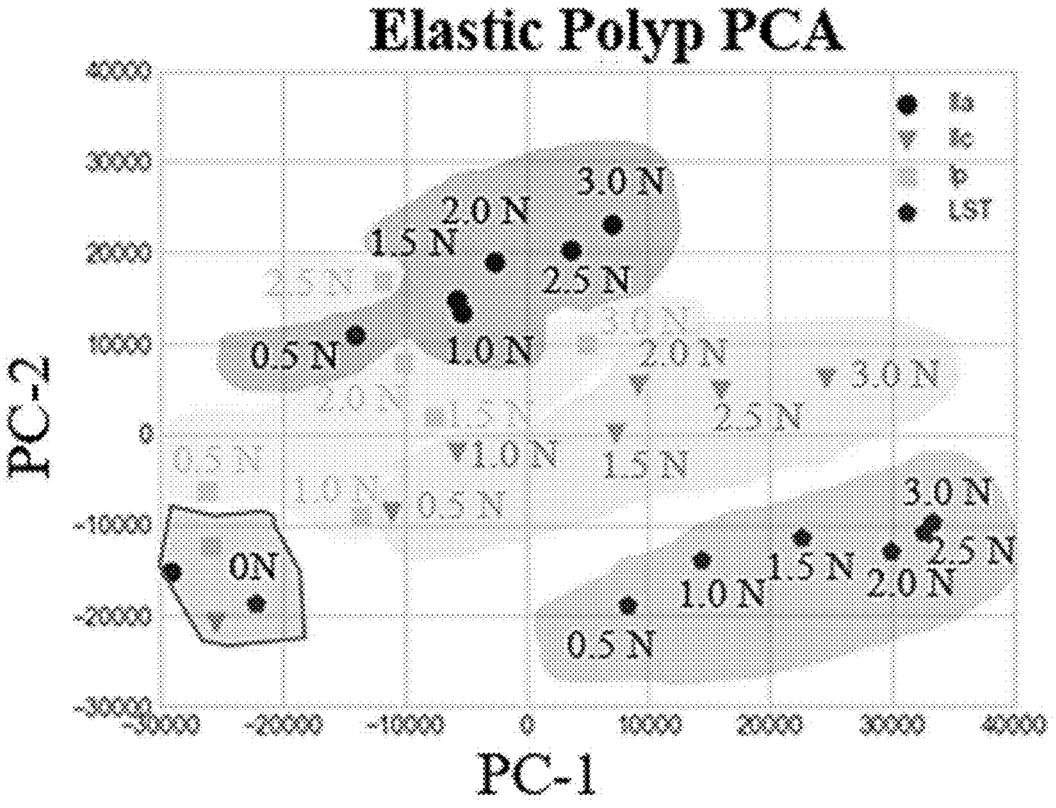
Figure 16D:
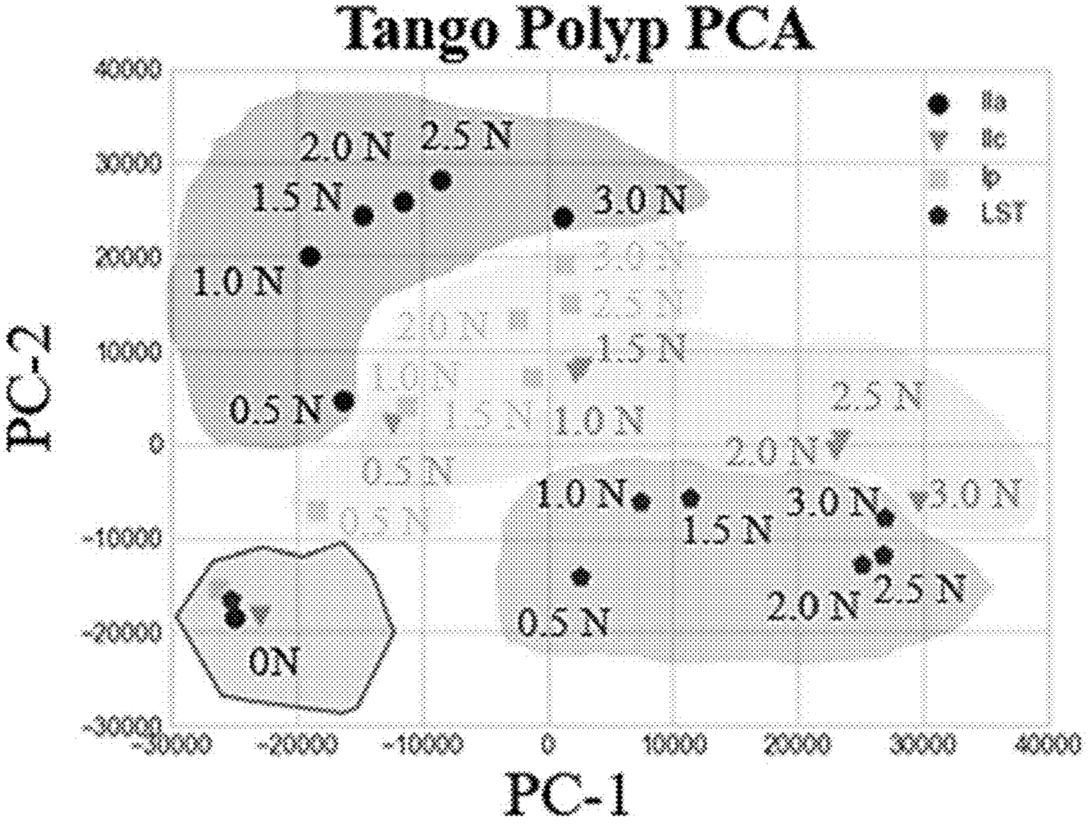
Figure 17A:
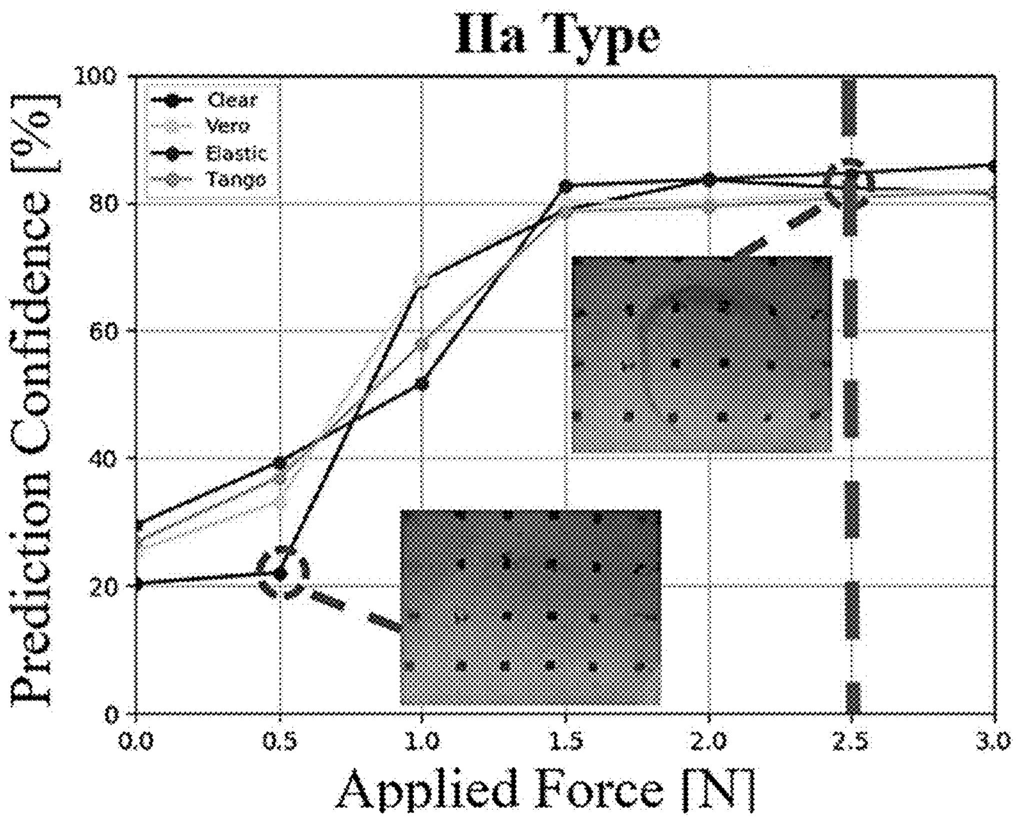
FIGS. 17A through 17D show results of the SVM trained on random samples of the interval displacement data set and tested on the force interval experiment data to find the applied force threshold where the characterization of the polyp can be achieved reliably (≥80%) in accordance with some embodiments.
Figure 17B:
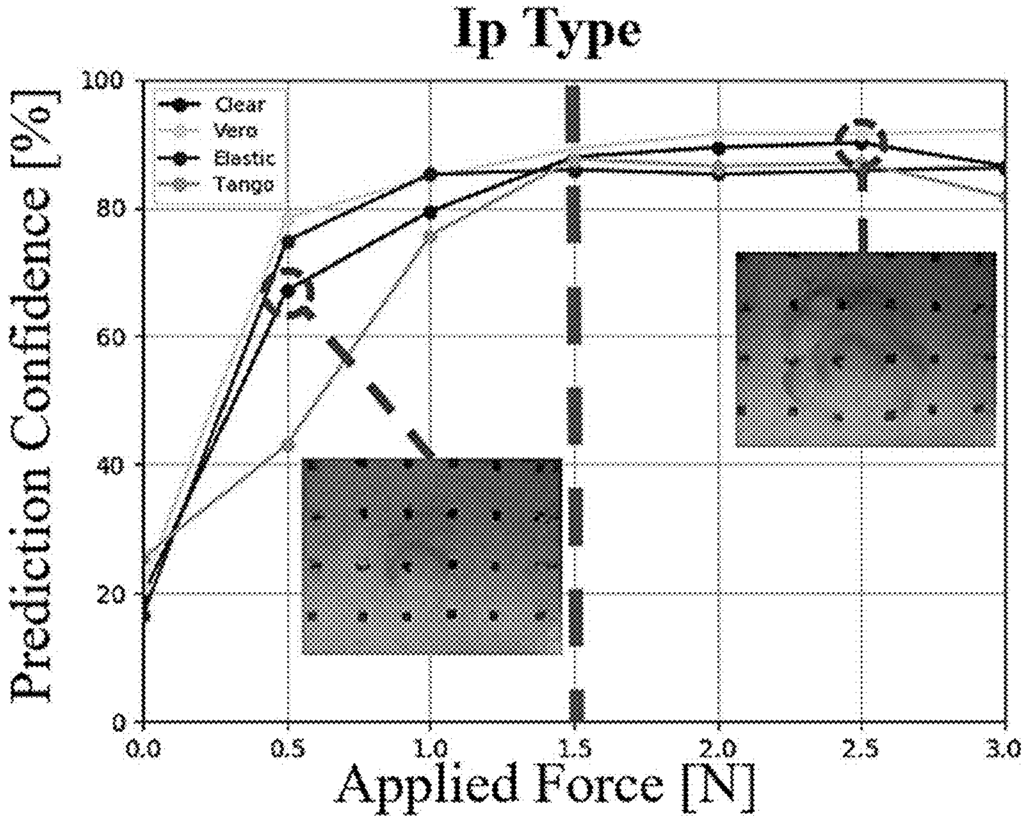
Figure 17C:
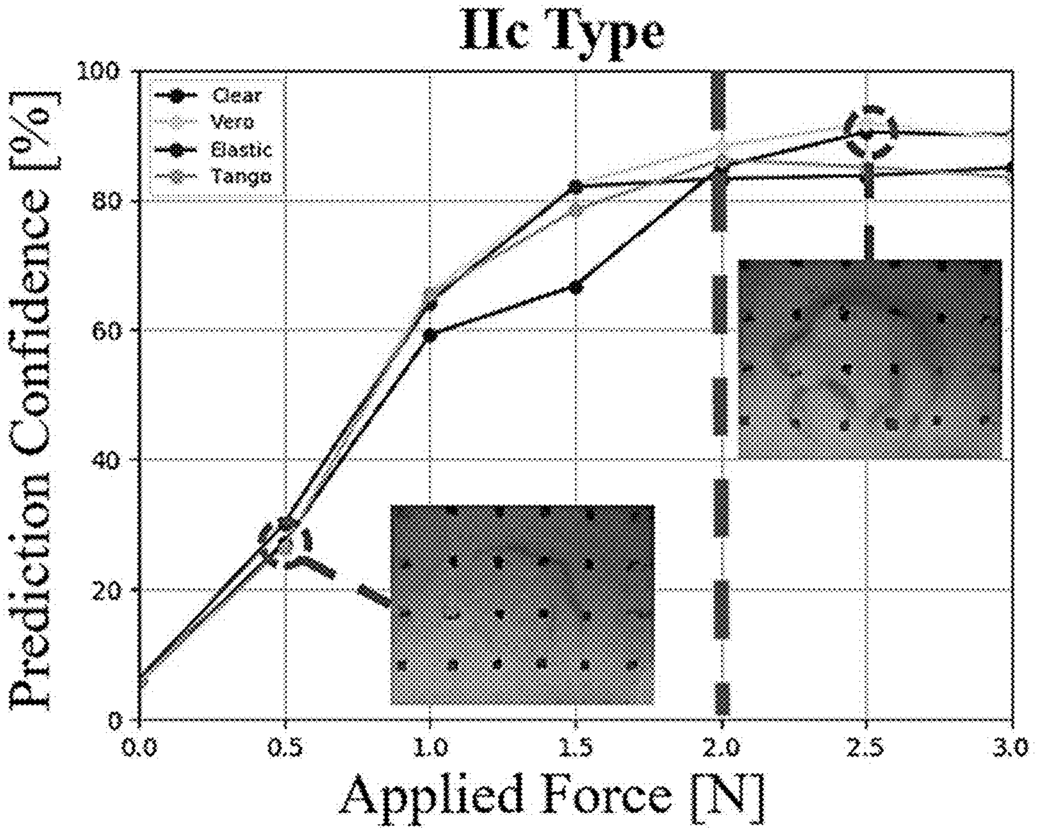
Figure 17D:
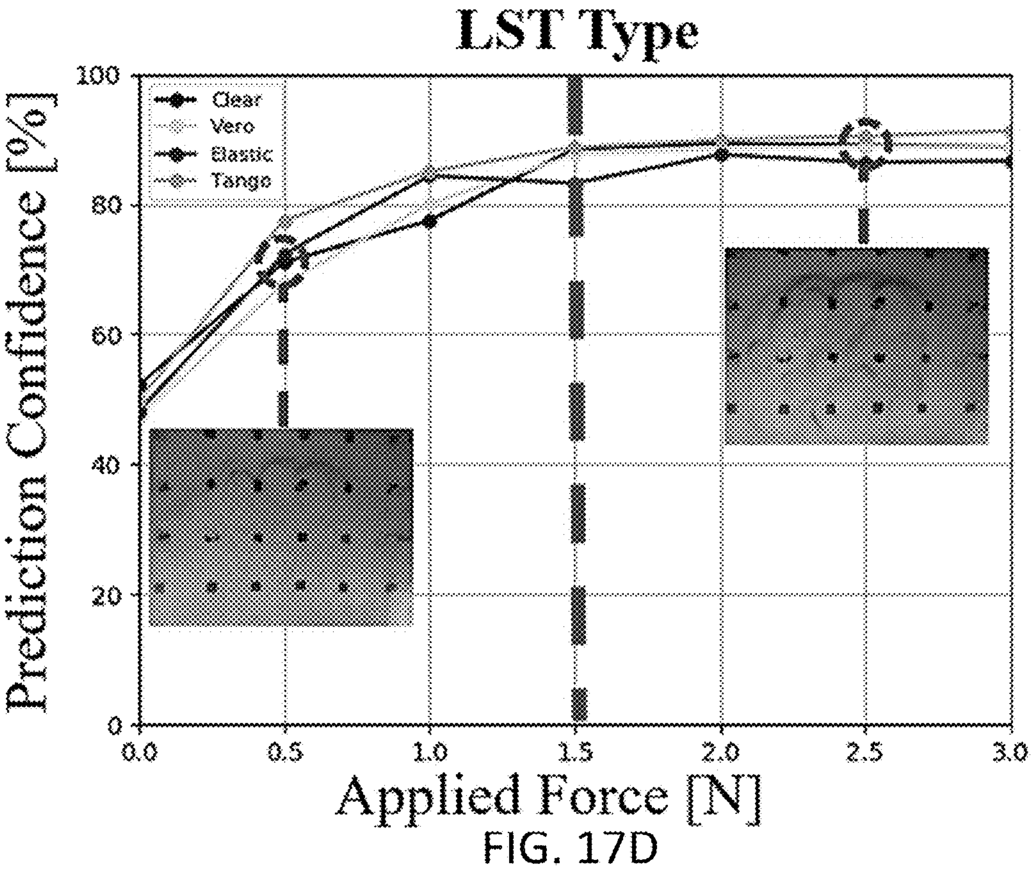
Figure 18A:
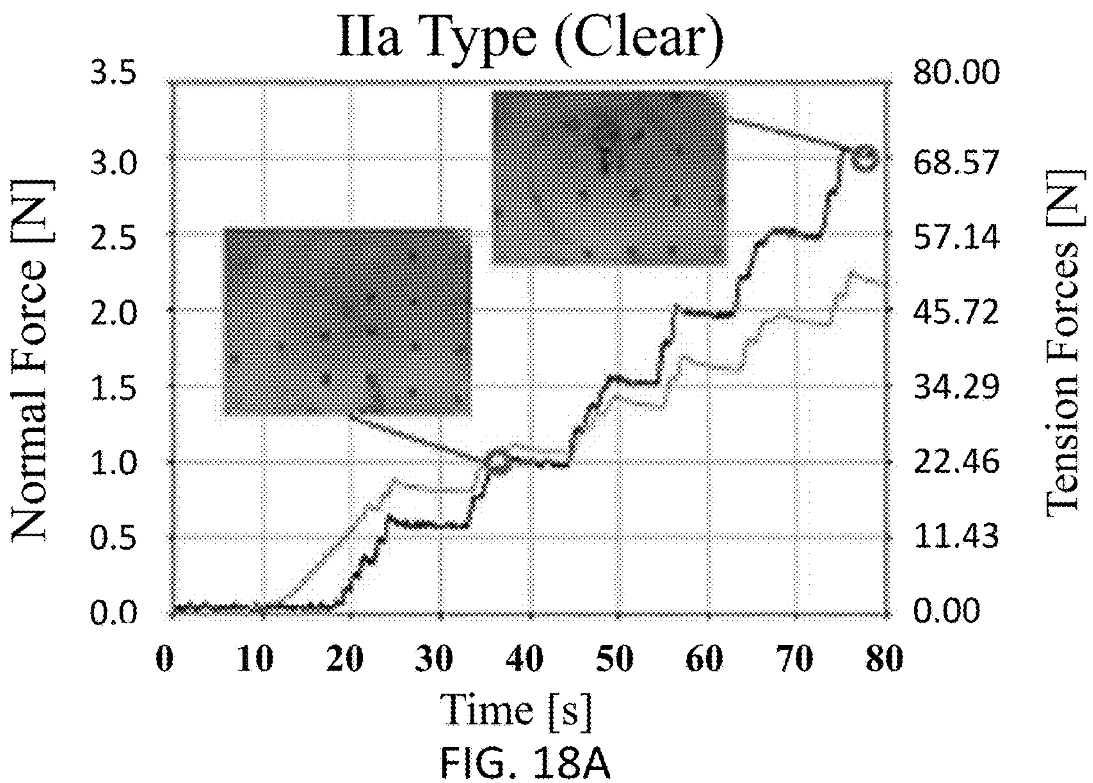
FIGS. 18A through 18D shows results of the embedded tactile sensor device 150 characterization in the colon phantom in accordance with some embodiments.
Figure 18B:
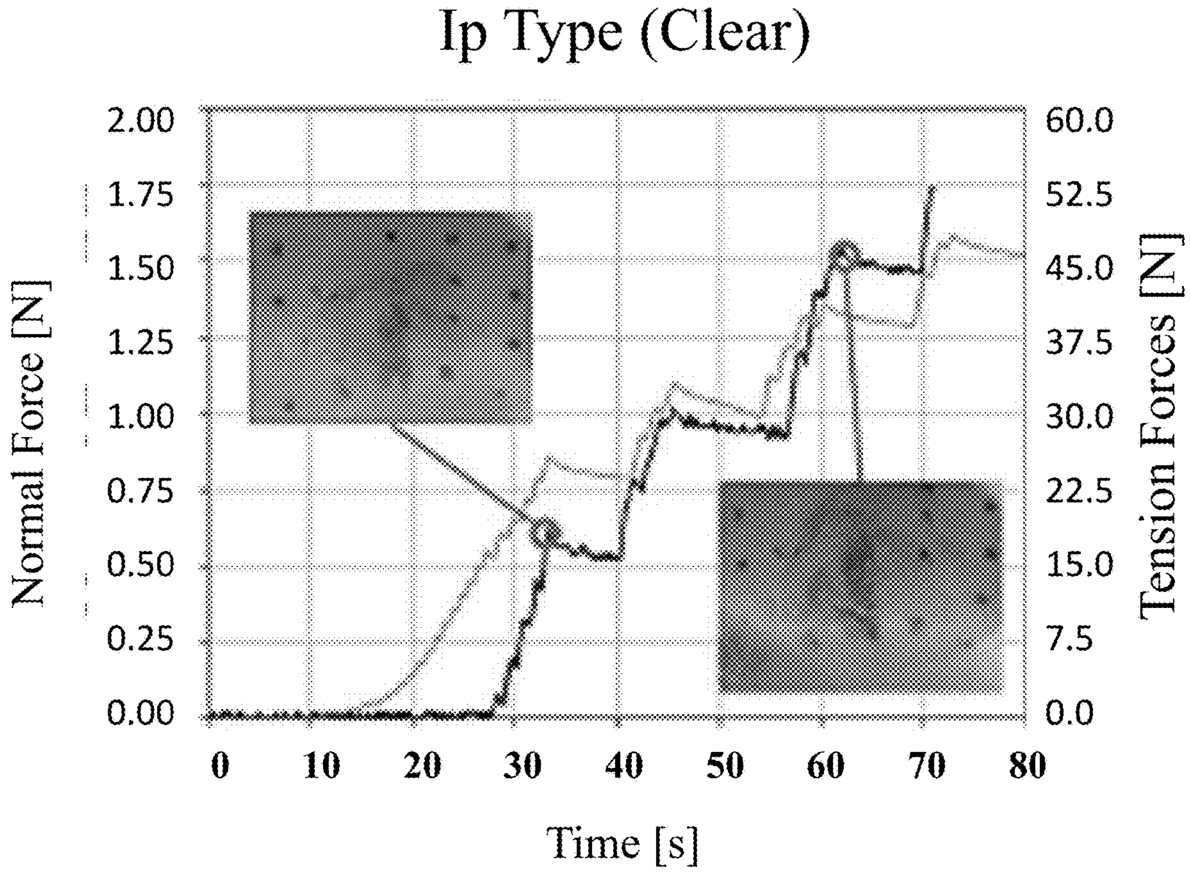
Figure 18C:
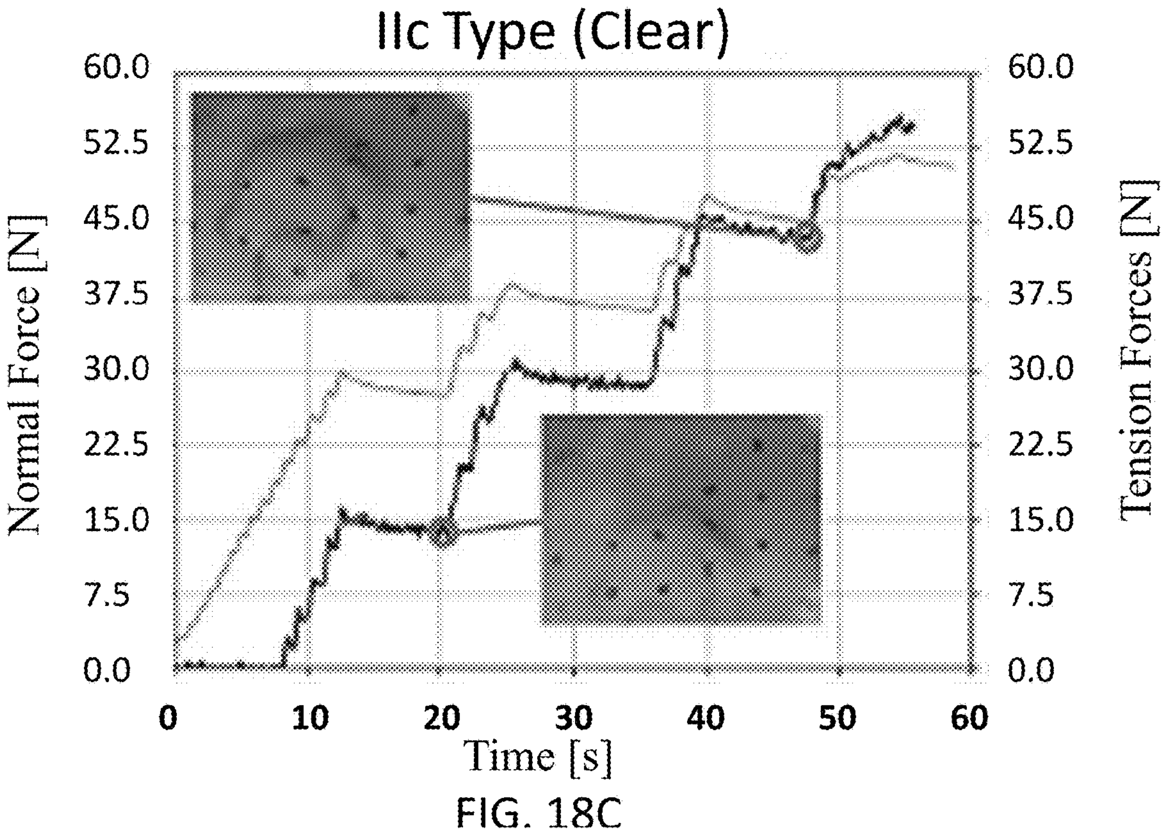
Figure 18D:
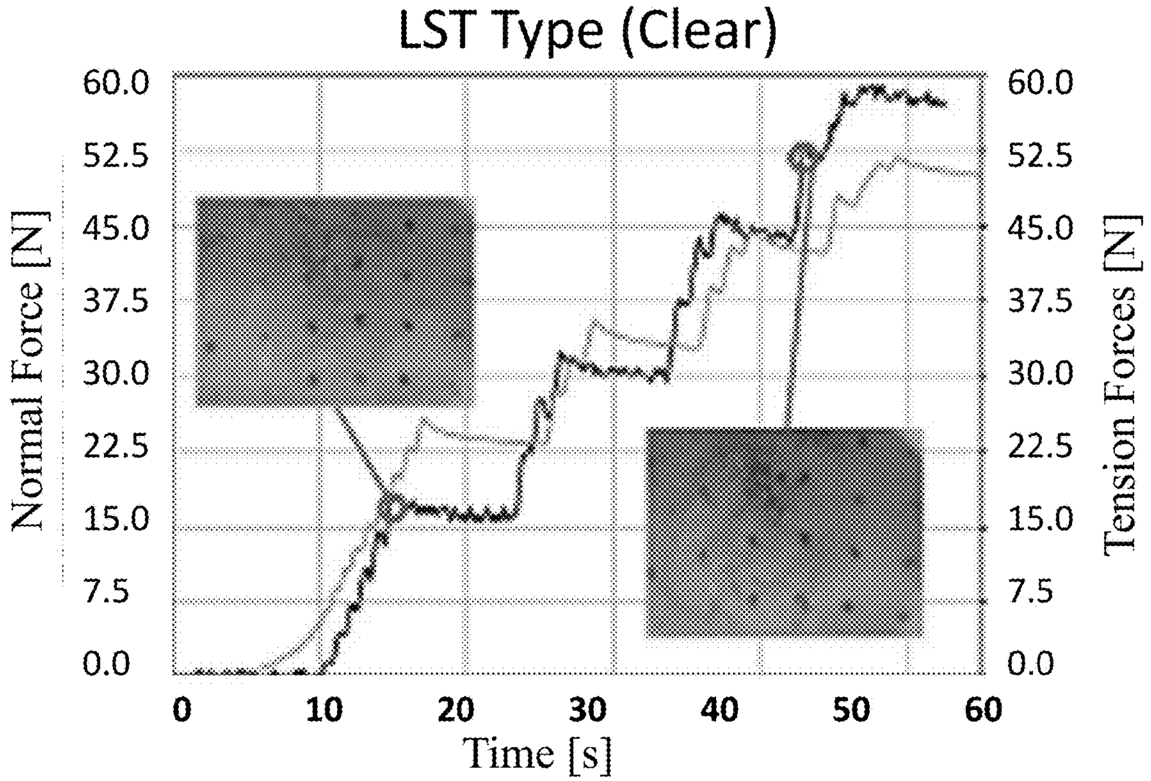

FIGS. 15A-15B show the experimental results of a displacement versus measured interaction normal force between the system 100 and phantom. The results of FIGS. 15A-15B show the influence of geometry and material property on polyp's deformation. In looking at the normal forces with respect to displacement, the material property of the polyp phantom mattered very little except with the pedunculated (Ip) polyp type. Note that the softer Ip type polyp phantoms experienced lower normal forces based on displacement compared to the harder Ip type polyp phantoms based on the shore hardness presented in the table of FIG. 12. This can be attributed to the Ip polyps being able to deform significantly with applied forces as opposed to the flat polyp types (IIa, IIc, LST). Such results have significant implication on how the deformation of the polyp, the sensor, and the soft robot can affect the applied forces on the polyp and colon environments.

FIGS. 16A-16D show the first two principal components (i.e., PC-1, PC-2) obtained by PCA analysis on the obtained system 100 images after pushing the polyps with different forces. The first two principal components account for over 44% of the variance in the data set. Principal component analysis (PCA) was performed on the polyp representation data set. For pre-processing, the mean image of 112 down-sampled 308 by 410 device images for all types at each force increment was taken. Then, the images were individually subtracted by the mean image and PCA was performed directly on these images. Note that the device images of the same polyp cluster together. Furthermore, note that the distances between the polyps increase as the applied force increases. This phenomenon is explained by the textural details available with each applied force. At low forces, tactile sensing device images may reveal there is contact but lack the sufficient textural details to inform polyp characterization. For the application of endoscopic/colonoscopic procedures, understanding this force-characterization confidence relationship is crucial as one needs to apply enough force to gather textural information without the risk of polyp rupture or gastrointestinal damages.

To explore the relationship between applied force and characterization confidence, classification and classification confidence of the images were studied. To this end, a support vector machine (SVM) approach was utilized. Specifically, to avoid overfitting based on the relatively limited image set, a cubic polynomial kernel was selected, and the regularization parameter was tuned. The model was trained using a random sample of the images from the displacement-normal force experiments and tested on the device images from the force increment experiments (i.e., 0.0-3.0 N at 0.5 N increments). Then, the distances to the support vectors for each image was calculated. The distances were then normalized to get a prediction confidence where the sum of the prediction confidences for each polyp type on an image summed to 100%. The resulting prediction confidences for each force increment and for each polyp type were plotted in FIGS. 17A-17D. For comparison, the red line indicates where the confidence threshold of 80% is reached by polyps of all materials of the polyp type. Note that the prediction confidence plateaus at just above 80% at 2 N, which is well below the safety limit of the colon (i.e., 13.5 N on a surface of 3.5 $mm^2$). Note that for IIa, IIc and LST type polyps, material properties have little effect on the prediction confidence. However, again for Ip type polyps, it was observed in the force range 0 to 1 N that Tango polyp sample lags behind others. The increased importance of material property was credited with Ip polyp type's topology that allowed folding at the stem.

FIGS. 17A-17D show results of the SVM trained on random samples of the interval displacement data set and tested on the force interval experiment data to find the applied force threshold where the characterization of the polyp can be achieved reliably (≥80%). The red line indicates the force threshold. The relationship between the input tension and the robot's applied force on the polyp is plotted in FIGS. 18A-18D along with the corresponding device images. The textural details were comparable to the direct external force measurement experiments. The bending motion of the robot also enabled the robot and the tactile sensor device 150 to gather textural detail from a different relative orientation compared to simply pressing the polyp onto the sensor. In colonoscopy, the ability to get texture from different orientations can assist in polyp characterization. These features hint at the usefulness of the disclosed soft robot with embedded tactile sensor device in the colonoscopy application.

FIGS. 18A-18D shows results of the embedded tactile sensor device 150 characterization in the colon phantom.

To address the sensitivity and durability trade-off of common VTSs, further disclosed are embodiments of designs and fabrication methods of a hyper-sensitive and high-fidelity VTS (referred to as HySenSe) that requires a very low interaction force (i.e., <1.5N) to obtain high-resolution images. To fabricate the high-fidelity VTS, the standard fabrication procedure of GelSight sensors (see W. Yuan et al., "Tactile measurement with a gelsight sensor," Ph.D. dissertation, Massachusetts Institute of Technology, 2014) was followed and altered to drastically improve the device's sensitivity and obtain high-quality images, all while applying a very low interaction force that does not compromise its durability. To thoroughly evaluate the performance of HySenSe, 3D image outputs were analyze and compared its results with a similar Gelsight sensor on different objects (with different shapes, textures, and stiffness) and under various interaction forces.

Figure 19:
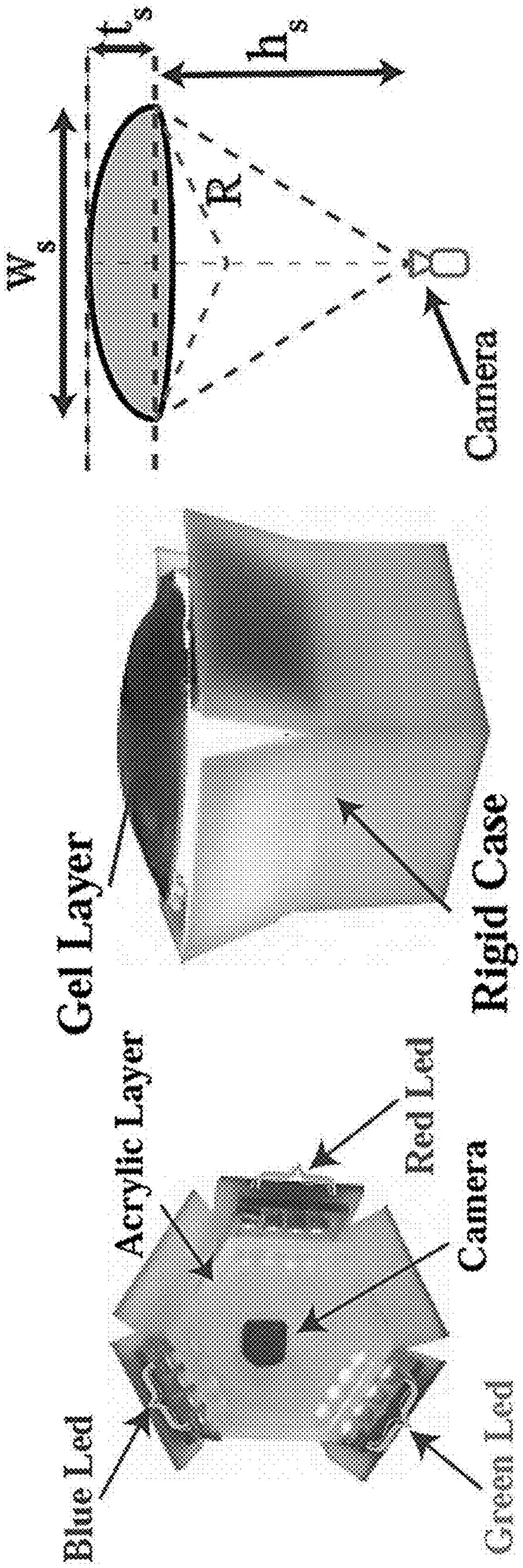
FIG. 19 depicts an exemplary experimental tactile sensor device in accordance with some embodiments.

As illustrated in FIG. 19 and similar to the GelSight sensor (see M. K. Johnson and E. H. Adelson, "Retrographic sensing for the measurement of surface texture and shape," in 2009 IEEE Conference on Computer Vision and Pattern Recognition. IEEE, 2009, pp. 1070-1077), HySenSe includes a dome-shape deformable silicone layer that directly interacts with an object, a camera that faces toward the gel layer and captures the deformation of the gel layer, and is fixed to the rigid frame of the sensor, a transparent acrylic layer that supports the gel layer and an array of Red, Green and Blue LEDs creating illumination and aiding in a recreation of the 3D textural features when an object interacts with the sensor. The working principle of GelSight and HySenSe are identical and very simple yet highly intuitive. The deformation caused by the interaction of the gel layer with the object can be visually captured by the small camera embedded in the frame.

To thoroughly evaluate the performance of HySenSe, similar GelSight and HySenSe sensors were fabricated. For both sensors, a 5 MP camera (Arducam ¼ inch 5 MP sensor mini) was used that was fixed to the rigid frame printed with high-resolution printing technology, a Form 3 printer (Formlabs Form 3, Formlabs Inc.), and the clear resin material (FLGPCL04, Formlabs Inc.). The rigid frame height was designed as $h_s$=24 mm, determined based on the camera focus and field of view. Of note, the other dimensions of the rigid frame are determined based on the size of the gel layer described below. Moreover, an array of Red, Green and Blue LEDs (WL-SMTD Mono-Color 150141RS63130, 150141GS63130, 150141BS63130, respectively) were placed and arranged 120 degrees apart. To have identical fabricated gel layers for these sensors and in order to build samples with identical volume and geometry, the volume of the spherical shape gel layers V was calculated as follows:

$$V = \frac{1}{3}\pi t_s^2(3R - t_s) \tag{1}$$

where, as conceptually demonstrated in FIG. 19, $w_s$ is the width of the gel layer, $t_s$ is the thickness of the fabricated samples, $h_s$ is the height of the rigid frame, and R is the radius of the hemispherical-shape gel layer.

As mentioned, the sensitivity of a VTS can be controlled using the utilized hardware components (see W. Yuan et al., "Tactile measurement with a gelsight sensor," Ph.D. dissertation, Massachusetts Institute of Technology, 2014) and/or post processing algorithms (see M. K. Johnson, F. Cole, A. Raj, and E. H. Adelson, "Microgeometry capture using an elastomeric sensor," ACM Transactions on Graphics (TOG), vol. 30, no. 4, pp. 1-8, 2011). Nevertheless, in this study, to fabricate a hyper-sensitive and durable VTS, it is shown that solely by changing one step during fabrication of the GelSight's gel layer, one can substantially increase the device's sensitivity and durability. The following briefly describes and compares the steps for fabricating a gel layer for GelSight sensor and the modified procedure for fabricating the gel layer for the HySenSe sensor.

Figure 20:
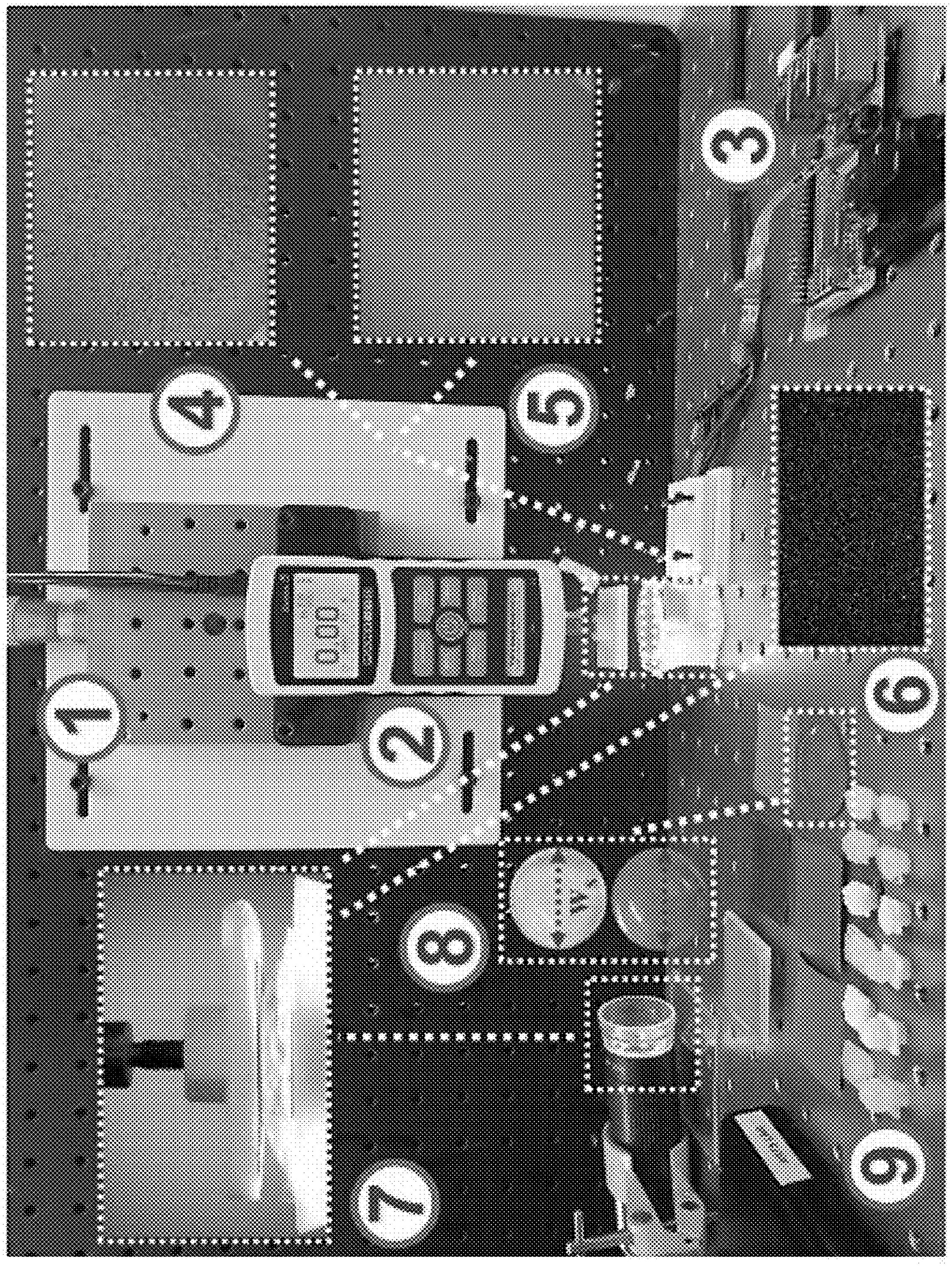
FIG. 20 shows an exemplary experimental setup in accordance with some embodiments.

FIG. 20 shows an image of the experimental setup, where 1 is the Linear Stage, 2 is the Force Gauge, 3 is the Raspberry Pi, 4 is HySenSe's image output of the sand paper, 5 is GelSight's image output of the sand paper (2.5 N), 6 is the 150 grit sand paper (2.5 N), 7 is the Side View of the interaction surface, 8 is HySenSe (above) and GelSight (below) gel layers, $w_s$=33.4, and 9 is the Different objects used for the experiments.

GelSight Gel Layer:

Step 1: For the fabrication of the gel layer (shown in FIG. 20), a soft transparent platinum cure two-part (consisting of Part A and Part B) silicone (P-565, Silicones Inc.) was used. In this study, a 14:10:4 (A:B:C) as a mixture mass proportion was used, in which Part C corresponds to phenyl trimethicone-softener (LC1550, Lotioncrafter). Notably, this proportion can readily be changed depending on the application requirements. Next, to fabricate a hemispherical-shape gel layer (shown in FIG. 19), a silicone mold (Baker depot mold for chocolate) was used with R=35 mm and its surface was coated with Ease 200 (Mann Technologies) to prevent adhesion and ensure a high surface quality after molding. After the coating was dried, the prepared silicone mixture was poured into the mold and then degassed in a vacuum chamber to remove the bubbles trapped within the mixture. Next, samples were cured in a curing station (Formlabs Form Cure Curing Chamber).

Step 2: After curing, the matte-colored aluminum powder (AL-101, Atlantic Equipment Engineers) was brushed on the gel layer's dome surface to avoid light leakage. Of note, the fabricated gel layer had $w_s$=33.8 mm and $t_s$=4.5 mm, which relatively has a higher thickness compared to the previous literature (see W. Yuan et al., "Gelsight: High-resolution robot tactile sensors for estimating geometry and force," Sensors, vol. 17, no. 12, p. 2762, 2017) (see M. K. Johnson et al., "Microgeometry capture using an elastomeric sensor," ACM Transactions on Graphics (TOG), vol. 30, no. 4, pp. 1-8, 2011). Remarkably, these parameters can readily be changed depending on the application requirements.

Step 3: Finally, a thin layer of silicone with the addition of grey pigment (blend of both black and white pigments-Silc Pig Black, Silc Pig White, Smooth-On Inc) was poured, with identical proportion described in STEP I, on the surface of gel layer to prevent light leakage and stabilize the aluminum powder layer. Notably, the hardness of the fabricated gel layer was measured as 00-20 using a Shore 00 scale durometer (Model 1600 Dial Shore 00, Rex Gauge Company). The fabricated gel layer is shown in FIG. 20.

HySenSe Gel Layer:

To fabricate the gel layer for the HySenSe sensor (shown in FIG. 20), the above-described procedure in for GelSight STEP 1 was followed. The major change in the HySenSe fabrication procedure happens in Step 2 in which, instead of brushing the aluminum powder on the surface of the fabricated gel layer, a Specialty Mirror Effect spray paint (Rust-Oleum Inc.) was utilized to create a thin reflective coating that was sprayed on the surface of the fabricated gel layer for 5 times with 1-minute intervals (to ensure the sprayed paint is cured). Using the spray paint eliminates the need for the addition of grey pigment with the silicone mixture in Step 3. Thus, as the last fabrication step, a thin layer of silicone mixture, as prepared in Step 1, was poured on the surface of the gel layer to cover the spray coating. Notably, the hardness of the fabricated gel layer was measured as 00-18 using the Shore 00 scale durometer.

FIG. 20 shows the experimental setup used to evaluate the sensitivity and fidelity of the HySenSe and GelSight sensors by comparing their textural images while measuring the interaction forces between their gel layers and the objects. As shown, the setup includes HySenSe and GelSight sensors, a single-row linear stage with 1 μm precision (M-UMR12.40, Newport), a digital force gauge with 0.02 N resolution (Mark10 Series 5, Mark-10 Corporation) attached to the linear stage to precisely push various objects on the sensors gel layers and measure the applied interaction force, and a Raspberry Pi 4 Model B for streaming and recording the obtained images by sensors. Also utilized was MESUR Lite Basic data acquisition software (Mark-10 Corporation) to record the interaction forces between the gel layers and objects.

Figure 21:
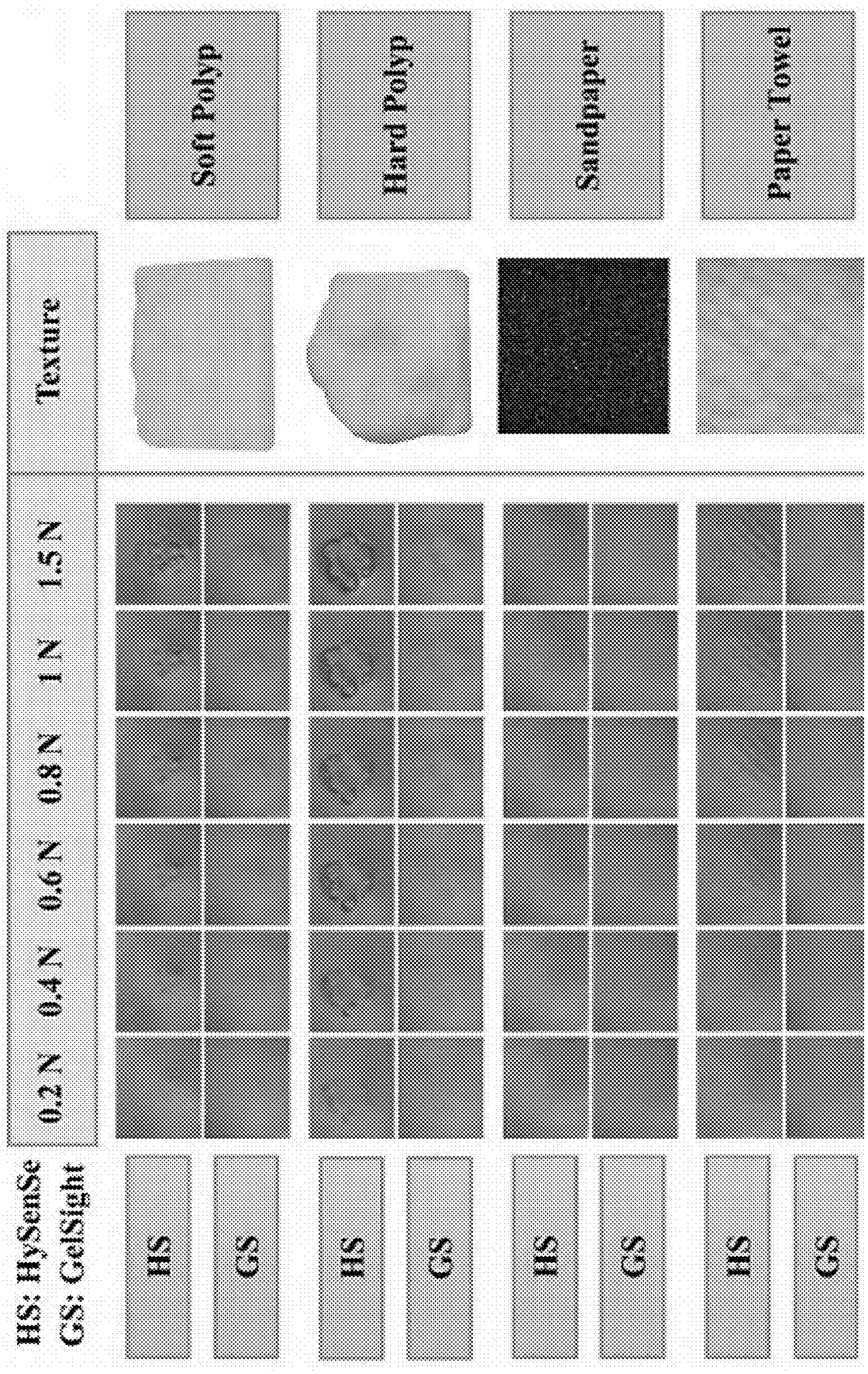
FIG. 21 depicts exemplary experimental results showing evolution of the visual outputs for the HySenSe and GelSight sensors in accordance with some embodiments. Each two rows of the figure corresponds to a specific object used for experiments. Also, the top row indicates the applied forces corresponding to each image.

To thoroughly compare the sensitivity and durability of the HySenSe and GelSight sensors independent of the size, shape, thickness, texture, and hardness of objects, as shown in FIG. 21, distinct test cases were considered. To evaluate performance of the sensors on flat and thin objects with different hardness and texture, samples were made from a 150 grit silicon carbide sandpaper (SKOCHE) with 95 μm grain size and a piece of soft paper towel (Bounty, Procter & Gamble Inc.) with 1.1 mm textural details. Also, to investigate the sensitivity of fabricated sensors on objects with non-flat geometry, heterogeneous texture, and distinct material hardness, 3D printed soft (type LST, DM400 material) and hard (type IIc, Vero PureWhite material) colorectal polyp phantoms (with Shore hardness 0045, D-83, respectively) based on the Paris classification (see T. Kaltenbach et al., "Endoscopic removal of colorectal lesions-recommendations by the us multi-society task force on colorectal cancer," Gastroenterology, vol. 158, no. 4, pp. 1095-1129, 2020), using Digital Anatomy Printer (J750, Stratasys, Ltd) (see H. Heo et al. "Manufacturing and characterization of hybrid bulk voxelated biomaterials printed by digital anatomy 3d printing," Polymers, vol. 13, no. 1, p. 123, 202)) were used. Dimensions (length×width×height) of the soft and hard polyp phantoms were 10.21×9.69×3.16 mm and 12.05×12.00×11.11 mm, respectively. For the performed experiments, the samples were first attached and secured to the force gauge. Then, the gel layers were fixated on the rigid frame, and the whole sensor was fixed to the optical table to block any undesired motion. Next, the linear stage was precisely pushed on the sensors' gel layers while measuring the displacement of the linear stage (i.e., deformation of the gel layer), interaction force, and obtained images by the sensors. FIG. 21 summarizes the results of the performed experiments.

To summarize, to improve the resolution of the VTS image outputs various approaches such as increasing the interaction forces (see W. Yuan et al., "Shape-independent hardness estimation using deep learning and a gelsight tactile sensor," in 2017 IEEE International Conference on Robotics and Automation (ICRA). IEEE, 2017, pp. 951-958), reducing the hardness and thickness of gel layer, complex fabrication procedures (see W. Yuan et al., "Gelsight: High-resolution robot tactile sensors for estimating geometry and force," Sensors, vol. 17, no. 12, p. 2762, 2017), and post processing image processing algorithms (see M. K. Johnson et al., "Microgeometry capture using an elastomeric sensor," ACM Transactions on Graphics (TOG), vol. 30, no. 4, pp. 1-8, 2011) have been implemented and proposed in the literature. Nevertheless, as demonstrated herein, by solely changing one step (i.e., Step 2) during the fabrication procedure of the gel layer, the sensitivity of the GelSight sensor can be drastically improved. More specifically, by using a mirror spray paint instead of aluminum powder and grey pigments, not only can one improve the reflectivity of the illumination, but one can also reduce the thickness of the coating to substantially improve the sensitivity.

FIG. 21 clearly demonstrates the superior sensitivity of the HySenSe compared with the GelSight sensor obtained under identical experimental conditions. As shown, the HySenSe sensor demonstrates substantially better performance than the GelSight sensor in creating high-fidelity images for all of the sample objects used independent of their hardness, size, thickness, and texture at very low interaction forces (i.e., ≤1.5 N). Particularly, even at ≤0.6 N interaction force, HySenSe can provide very visible and high-quality textural images (e.g., 95 μm grains in the sandpaper), whereas at these low forces, GelSight's outputs are very blurry and unclear. Of note, this important feature is critical for several applications (e.g., high-fidelity manipulation of fragile objects (see N. R. Sinatra et al., "Ultragentle manipulation of delicate structures using a soft robotic gripper," Science Robotics, vol. 4, no. 33, p. eaax5425, 2019) and medical applications (see E. Heijnsdijk et al., "Inter- and intraindividual variabilities of perforation forces of human and pig bowel tissue," Surgical Endoscopy and other interventional Techniques, vol. 17, no. 12, pp. 1923-1926, 2003) in which a high sensitivity at low interaction forces is necessary to ensure the safety of tactile measurements while providing a high-resolution image output.

Aside from sensitivity, the disclosed fabrication procedure for the HySenSe also can resolve the existing sensitivity and durability trade-off in VTSs. As described, to improve the durability of the GelSight sensors, the thickness and/or the hardness of the gel layer needs to be increased while this may drastically deteriorate the sensitivity of these sensors (see S. Dong et al., "Improved gelsight tactile sensor for measuring geometry and slip," in 2017 IEEE/RSJ International Conference on Intelligent Robots and Systems (IROS). IEEE, 2017, pp. 137-144). The typical remedy for such situations is to increase the interaction force between the object and the gel layer to obtain a high-quality image, which may not be feasible for many applications and may damage the sensor, too. Nevertheless, as shown in FIG. 21, the hypersensitivity of the HySenSe compared with the GelSight sensor, even in very low interaction forces, addresses the issue of sacrificing the durability for sensitivity and vice versa. In other words, the hypersensitivity of HySenSe mitigates the need for applying a high interaction force that may reduce the durability and the effective life of the sensor.

Disclosed embodiments were also utilized toward collectively addressing the abovementioned limitations of existing VTSs in quantitative measurements of gel layer deformation. Further explored was a design, fabrication, and characterization of a novel Quantitative Vision-based Tactile Sensor (Q-VTS). The core of the disclosed sensor is the utilization of miniature 1.5 mm×1.5 mm synthetic square markers with inner binary patterns and a broad black border called ArUco Markers (see S. Garrido-Jurado, "Automatic generation and detection of highly reliable' fiducial markers under occlusion," Pattern Recognition, vol. 47, no. 6, pp. 2280-2292, 2014). Each ArUco marker can provide real time camera pose estimation that can be used as a quantitative measure for obtaining deformation of the Q-VTS gel layer. Moreover, thanks to the use of ArUco markers, a novel fabrication procedure that mitigates the challenges mentioned above during the fabrication of VTSs is used. Particularly, the disclosed fabrication facilitates the integration and adherence of markers with the gel layer to robustly and reliably obtain a quantitative measure of deformation in real-time.

ArUco Markers:

Pose estimation is a computer vision problem that determines the orientation and position of the camera with respect to a given object and has great importance in many computer vision applications ranging from surgical robotics (see F. P. Villani et al., Development of an augmented reality system based on marker tracking for robotic assisted minimally invasive spine surgery," in International Conference on Pattern Recognition. Springer, 2021, pp. 461-475), and augmented reality (see C. Mela et al., "Novel multimodal, multiscale imaging system with augmented reality," Diagnostics, vol. 11, no. 3, p. 441, 2021), to robot localization (see A. de Oliveira Junior et al., "Improving the mobile robots indoor localization system by combining slam with fiducial markers," in 2021 Latin American Robotics Symposium (LARS), 2021 Brazilian Symposium on Robotics (SBR), and 2021 Workshop on Robotics in Education (WRE). IEEE, 2021, pp. 234-239). Binary square fiducial markers have been emerged as an accurate and reliable solution for the pose estimation problem in various applications (see S. Garrido-Jurado et al., "Automatic generation and detection of highly reliable' fiducial markers under occlusion," Pattern Recognition, vol. 47, no. 6, pp. 2280-2292, 2014). These markers offer easily discernible patterns with strong visual characteristics through their four corners and specific ID to obtain the camera pose. Moreover, their unique inner binary codes add robustness for the misdetections and reduce false positive detections (see M. Kalaitzakis et al., "Fiducial markers for pose estimation," Journal of Intelligent & Robotic Systems, vol. 101, no. 4, pp. 1-26, 2021). Various fiducial marker libraries has been developed progressively in the literature to address the pose estimation problem such as AprilTag (see E. Olson, "Apriltag: A robust and flexible visual fiducial system," in 2011 IEEE international conference on robotics and automation. IEEE, 2011, pp. 3400-3407), ARTag (see M. Fiala, "Artag, a fiducial marker system using digital techniques," in 2005 IEEE Computer Society Conference on Computer Vision and Pattern Recognition (CVPR'05), vol. 2. IEEE, 2005, pp. 590-596), and ArUco (see S. Garrido-Jurado et al., "Automatic generation and detection of highly reliable' fiducial markers under occlusion," Pattern Recognition, vol. 47, no. 6, pp. 2280-2292, 2014). A detailed review of fiducial marker packages and descriptions can be found in C. Mela et al., "Novel multimodal, multiscale imaging system with augmented reality," Diagnostics, vol. 11, no. 3, p. 441, 2021. In this work, ArUco markers were used for estimating the deformation of the VTS gel layer, as they can provide a high detection rate in real-time and allow the use of reconfigurable libraries with less computing time.

Q-VTS Design and Fabrication:

Working Principle and Constructing Elements of QVTS: As demonstrated in FIG. 22 and similar to the GelSight sensor (see W. Yuan et al., "Gelsight: High-resolution robot tactile sensors for estimating geometry and force," Sensors, vol. 17, no. 12, p. 2762, 2017), Q-VTS comprised of a dome-shape deformable silicone gel layer integrated with multiple ArUco markers for the quantification of the deformation field of the elastomer surface that directly interacts with an object, an autofocus camera that is fixed to the 3D printed frame of the sensor and faces toward the elastic gel layer to record the deformation of the gel layer and the movements of the ArUco markers, and a highly transparent Quartz glass layer (7784N13, McMaster-Carr) that supports the gel layer while providing a clear view to the camera. Of note, unlike the typical Gelsight sensors, Q-VTS does not require Red, Blue, and Green (RGB) LEDs, as they create a glare on the inked surface of the printed ArUco markers preventing their edges from properly being detected during deformation. Instead, ambient lighting is preferred and used to not interfere with the ArUco markers edge detection. The working principle of Q-VTS, similar to the GelSight sensor, is very simple yet highly intuitive, in which the deformation caused by the interaction of the silicone gel layer with the object can be captured by the autofocus camera and quantified through ArUco markers adhered to the surface of the gel layer and continuously moving with that.

Fabrication Procedure of the Q-VTS: To fabricate the Q-VTS, a 13 MP autofocus USB camera (IEights 4K ⅓ inch with an IMX 415 sensor and 5-50 mm varifocal lens) was used that was fixed to the rigid frame printed with a 3D printer (E2, Raise3D), and the PLA filament (Art White Extreme Smooth Surface Quality, Raise3D). An autofocus camera was a suitable selection for Q-VTS as one could control and optimize the focal distance through the deformation procedure of the gel layer and always ensure a clear output image. In other words, a fixed focal length camera may create blurry visuals after exceeding the focus threshold and throughout the gel layer deformation. The rigid frame height was designed as $h_s$=55 mm based on the camera focus and 100° field of view. Of note, the zoom parameter of the autofocus camera and the distance between the camera and the ArUco markers were optimized to find the balance between the detection rate and the correct pose estimation of markers.

Fabrication Procedure of the Gel Layer: The following paragraphs describe and compare the steps taken for fabricating a typical GelSight sensor and the novel fabrication method for the Q-VTS sensor.

Figure 22:
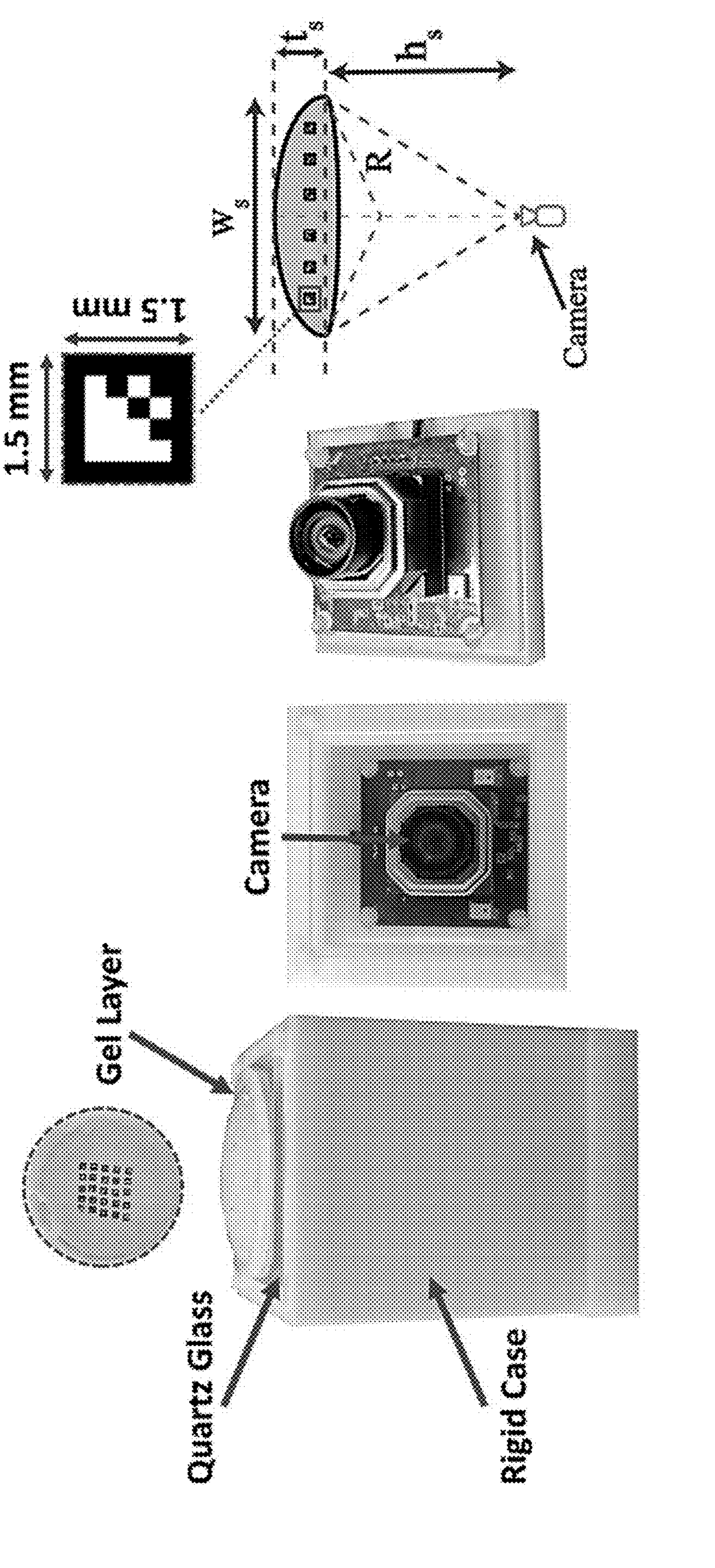
FIG. 22 depicts an exemplary experimental quantitative tactile sensor device in accordance with some embodiments.

GelSight Sensor: STEP 1: To fabricate the deformable gel layer (as illustrated in FIG. 22), a soft transparent platinum cure two-part (consisting of Part A and Part B) silicone (P-565, Silicones Inc.) was used, with a 14:10:4 ratio (A:B:C), in which Part C represents the phenyl trimethicone-softener (LC1550, Lotioncrafter). In this mixture, Part B functions as the activator of the two-part silicone, which can adjust the hardness of the silicone. Before pouring the silicone mixture into the hemispherical-shape silicone mold (Baker depot mold for chocolate with a diameter of 35 mm), the surface of the silicone mold was coated with Ease 200 (Mann Technologies) twice to prevent adhesion and ensure a high surface quality after molding. After waiting for the drying of the coating for 10-12 minutes, the silicone mixture was poured into a silicone mold and then degassed in a vacuum chamber to remove the bubbles trapped within the mixture. Next, samples were solidified in a curing station (Formlabs Form Cure Curing Chamber). Of note, as demonstrated in FIG. 22, the fabricated gel layer had width ($w_s$) and thickness ($t_s$) of 33.8 mm and 4.5 mm, respectively.

GelSight Sensor: STEP 2: After the curing step, black marker dots on the sensor surface could be attached either using waterslide decal paper (see W. Yuan et al., "Gelsight: High-resolution robot tactile sensors for estimating geometry and force," Sensors, vol. 17, no. 12, p. 2762, 2017) or manually marking by hand (see W. Yuan et al., "Shape-independent hardness estimation using deep learning and a gelsight tactile sensor," in 2017 IEEE International Conference on Robotics and Automation (ICRA). IEEE, 2017, pp. 951-958). For the first option, the marker dot pattern was printed on the glossy side of the water transfer paper via a laserjet printer. Then, the transfer paper was soaked in medium-temperature water to wet the paper surface to maneuver and peel the printed side off easily. Afterwards, the transfer paper was placed on the dome-shape gel layer with the marker dots facing up while separating the backing paper. Of note, this arduous procedure demands multiple repetitions and requires experience in working with the decal papers for the integration of it on the sensor surface. Even if the transfer paper is placed correctly on the surface of the gel layer, it will most likely be wrinkled when it interacts with an object, and therefore deteriorates the sensor sensitivity and quality of the output images. The second option is relatively manageable but lacks a consistent black dot marking procedure and does not provide a quantitative measure for the gel layer deformation.

GelSight Sensor: STEP 3: This step includes covering the printed markers on the gel layer's surface. To this end, first, the matte-colored aluminum powder (AL-101, Atlantic Equipment Engineers) was brushed on the gel layer's dome surface to avoid light leakage. Finally, a thin layer of silicone with the addition of grey pigment (blend of both black and white pigments-Silc Pig Black, Silc Pig White, Smooth-On Inc) was poured, with identical proportion described in STEP 1, on the surface of gel layer to stabilize the aluminum powder layer and prevent light leakage since there exist RGB LEDs within the rigid casing. Notably, the hardness of the gel layer sample was measured as 00-20 using a Shore 00 scale durometer (Model 1600 Dial Shore 00, Rex Gauge Company).

Figure 23:
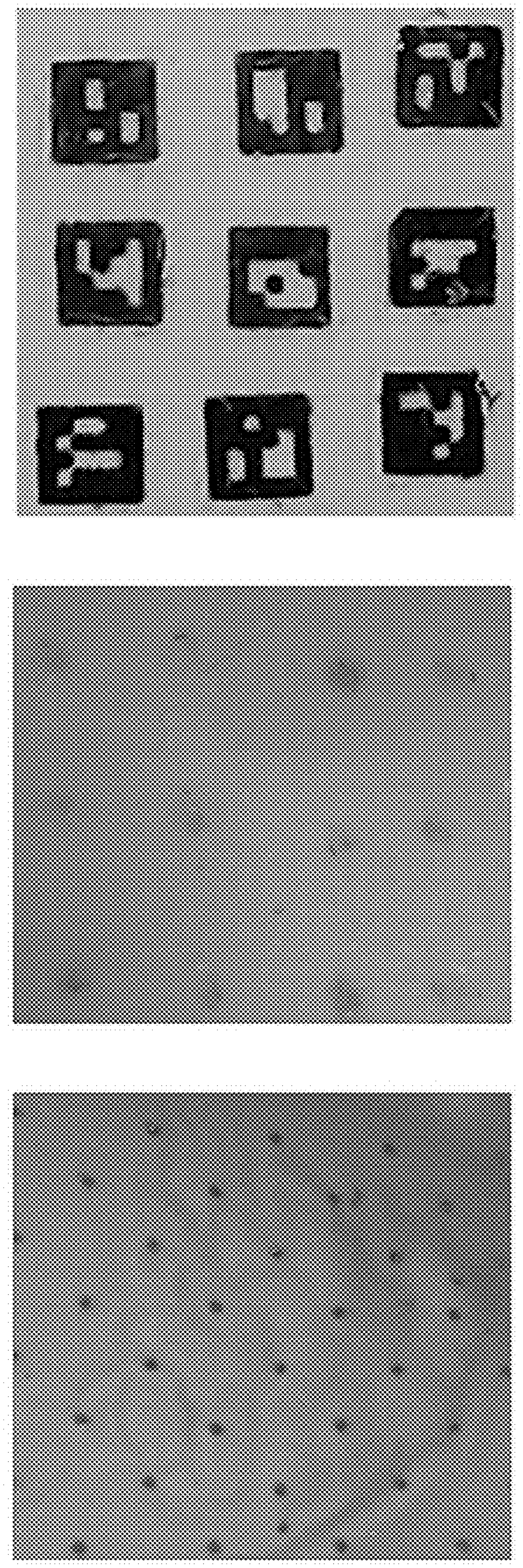
FIG. 23 shows a comparison of marker placement methods in accordance with some embodiments.

Q-VTS: To fabricate the deformable gel layer for the novel sensor, above-described procedure in STEP 1 was followed. The significant change in the Q-VTS fabrication procedure occurs in STEP 2 and STEP 3 in which, instead of utilizing black dot marker patterns, 25 square ArUco Markers were used with the size of 1.5 mm×1.5 mm. They were adhered separately and one by one to the Q-VTS gel layer surface. Each ArUco Markers were printed on a water transfer paper (Sunnyscopa) using a laserjet printer (Color Laser Jet Pro MFP M281fdw, HewlettPackard) with 600×600 DPI to obtain the best printing quality from the utilized printer. Of note, the 1.5 mm×1.5 mm marker size was determined after performing a few preliminary tests with the detection algorithm. It is worth mentioning that high DPI printing quality would enable using smaller marker sizes while still having a high detection rate. Before placing each ArUco marker, the sensor's surface was brushed with the versatile decal setting solution, Micro Set (Microscale Industries), to increase the adhesion and prepare the surface for the application of the transfer paper. After 510 minutes, each marker was placed with precision tweezers one by one by following the instructional procedures of the transfer paper to create a 5×5 array on the sensor surface. Of note, as each marker was positioned separately, and ArUco Markers could be detected independently, regardless of their positioning, orientation, and uniformity, the problems mentioned earlier in STEP 2 of GelSight preparation were not an issue. FIG. 23 shows the fabricated markers using the described procedures. The left figure shows the wrinkle problem that may occur during the interaction or after the removal of the interaction force, the central figures shows Inconsistent black dot patterns due to manual marker placement, and the right figured shows a zoomed view of the ArUco marker pattern on the Q-VTS surface used for the deformation estimation of the gel layer regardless of the orientation of each marker and placement inconsistencies.

It is worth noting that due to the use of ambient light instead of LEDs, the disclosed fabrication method eliminates the need for additional aluminum powder brushing in STEP 3. Thus, as the last fabrication step, a thin layer of silicone mixture with the addition of white pigment (Silc Pig White, Smooth-On Inc) and the same proportion as in STEP 1, was poured on the sensor surface to cover the ArUco Markers. Of note, white pigment is preferred to easily distinguish the black-colored patterns of the markers from the white background and aid the computer vision algorithm during the detection procedure.

Figure 24:
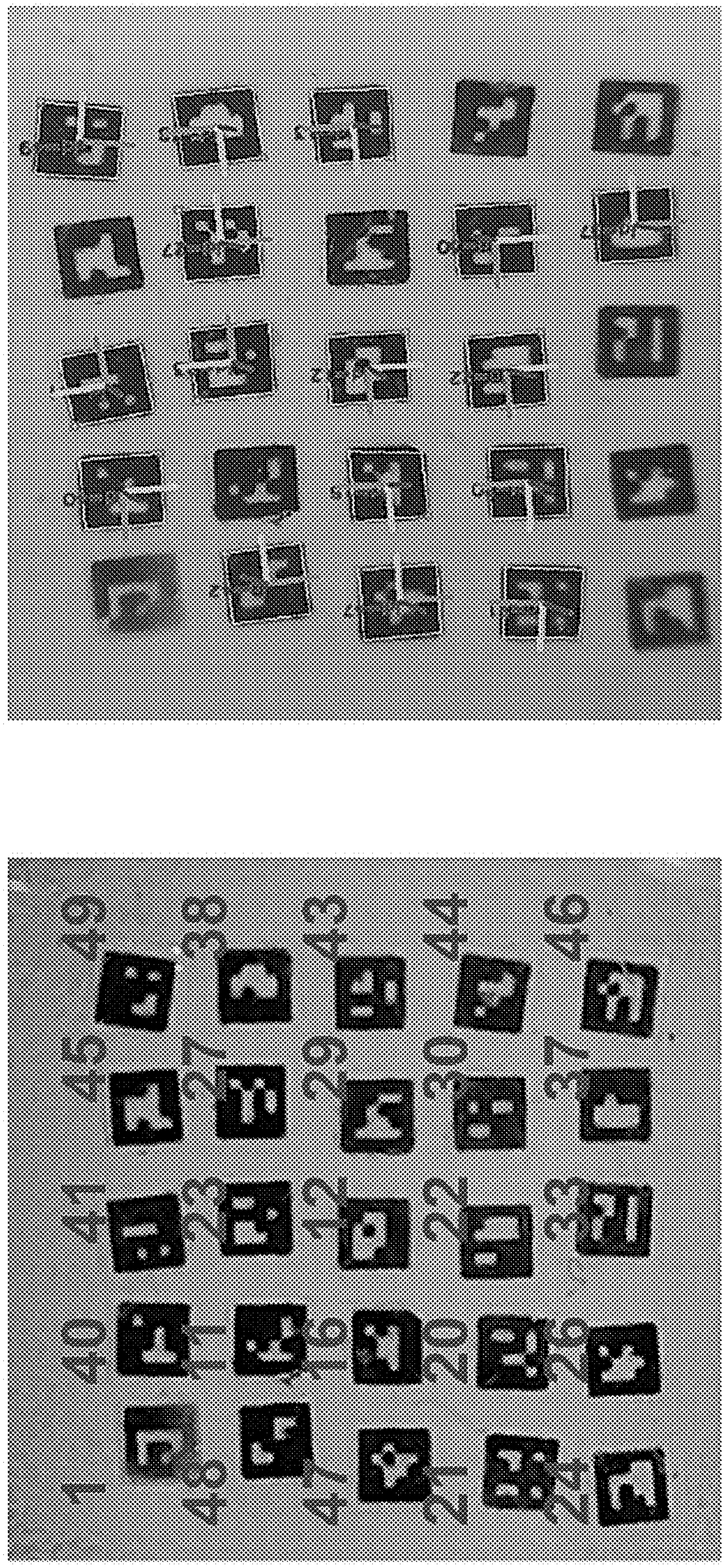
FIG. 24 shows ArUco markers integrated into the device in accordance with some embodiments.

ArUco Marker Detection and Pose Estimation:

As demonstrated in FIG. 24, each ArUco Marker has its own binary codification and identification to provide a 3D position and orientation of the camera toward them. These fiducial markers have libraries based on OpenCV and are written in C++ (see S. Garrido-Jurado et al., "Automatic generation and detection of highly reliable' fiducial markers under occlusion," Pattern Recognition, vol. 47, no. 6, pp. 2280-2292, 2014). This architecture employs square markers, which can be built for different dictionaries varying in number of bits and sizes. ArUco allows us to use reconfigurable predefined marker dictionaries, DICT XXX Y, in which X (4, 5, or 6) and Y (50, 100, 250, 1000) represent marker size in bits, and the number of the markers stored in this library, respectively. The number of bits affects the confusion rate and the required camera accuracy and resolution. If the bit size is small, the patterns are more straightforward, and markers can be detected at lower resolution with the trade-off of a higher confusion rate. In addition to the bit size and number of markers in the dictionary, the intermarker distance, the minimum distance between two separate fiducial markers, is a significant factor that can determine the error detection and correction capabilities. Mainly, larger markers and smaller dictionary sizes can also decrease the confusion between markers and aid in identifying a specific marker with higher accuracy. On the other hand, detecting markers with higher bit sizes becomes complex due to the requirement of a higher number of bits extracted from the image.

FIG. 24 shows ArUco markers integrated with the elastic gel layer of Q-VTS. Each marker has its own ID to be recognized through the computer vision algorithm. The left figure shows a zoomed view of the ArUco markers with their unique identification numbers, and the right figure shows a randomly selected frame showing the detected ArUco markers.

A 4×4 bit library was selected with 50 ArUco markers to have a robust detection of errors for the 25 ArUco markers (as demonstrated in FIG. 24), in consequence of the clarifications mentioned earlier. A 5×5 array of markers, sizing 1.5 mm×1.5 mm square, are prepared in order to create a balance between the total number of markers and the resolution and sensitivity of the sensor since a smaller size of markers means that more markers can be attached to the surface. All markers are generated through an online generator website (see ArUco markers generator!" Accessed: 2022 Jul. 23. [Online]. Available: https://chev.me/arucogen/). Notably, the number, size, and attachment pattern of ArUco markers can be readily optimized and varied based on the application.

After integrating each of the 25 ArUco Marker on the deformable gel layer (shown in FIG. 23), the Hamming coding algorithm proposed in Garrido-Jurado et al. was followed, to optimize the low false negative rate for the pose estimation. The detection process started with the acquisition of the images from the autofocus camera. Then, these images were converted to grayscale to reduce the computational requirement and simplify the overall algorithm. Afterwards, contours were extracted as rectangles and filtered to obtain marker candidates, and perspectives were removed. Finally, the ID of each detected marker was generated with the rotation and translation vectors through the extraction of the unique binary codes secured in the markers and comparison of these codes with the selected marker dictionary. A Python solution was implemented for this algorithm to work in real-time while saving both detection rates and pose estimations to an Excel file. FIG. 23 shows ArUco Markers placed on the elastic gel layer of Q-VTS. As shown, each marker has its own ID to be recognized through the computer vision algorithm.

Figure 25:
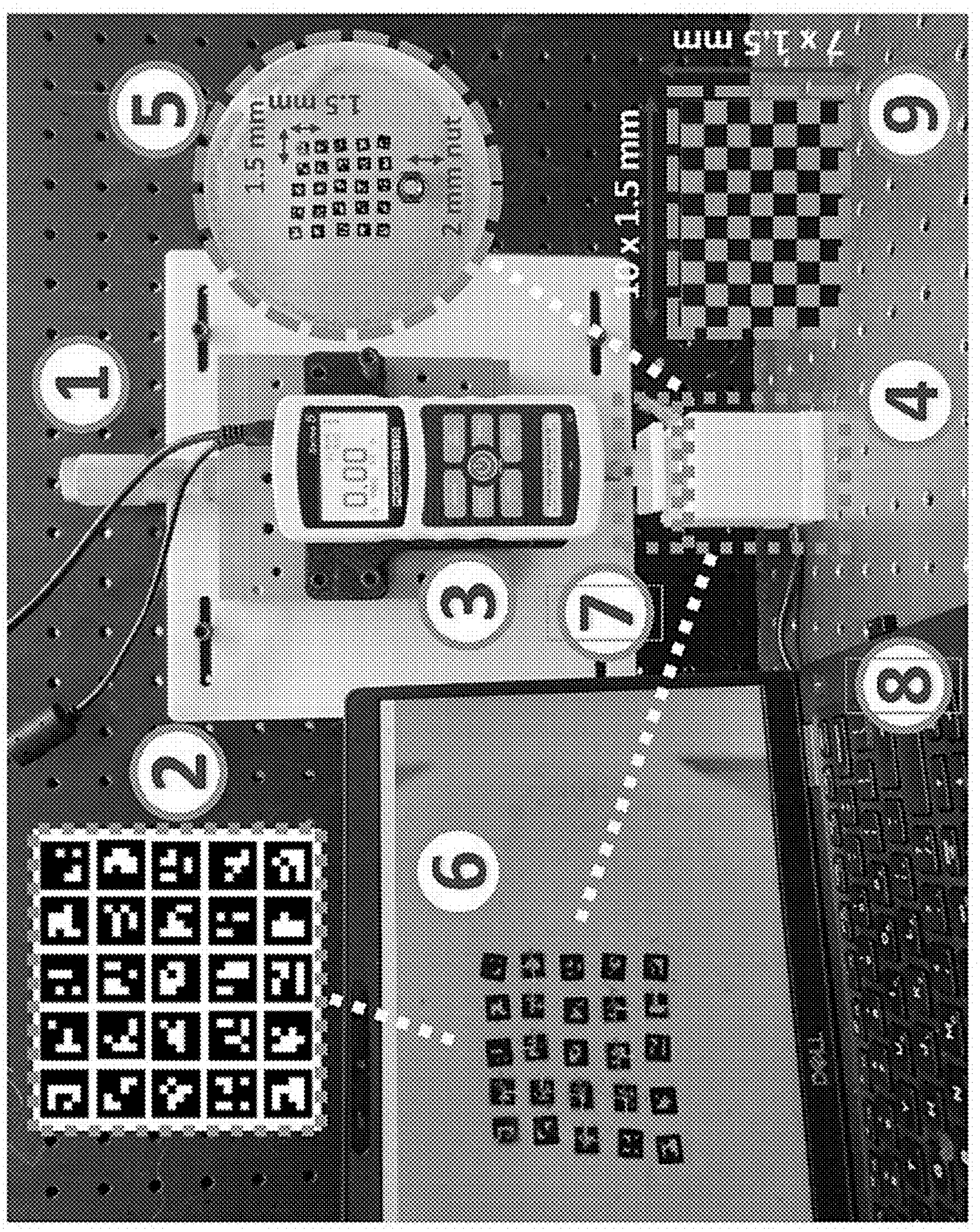
FIG. 25 shows an exemplary experimental setup in accordance with some embodiments.
Figure 26A:
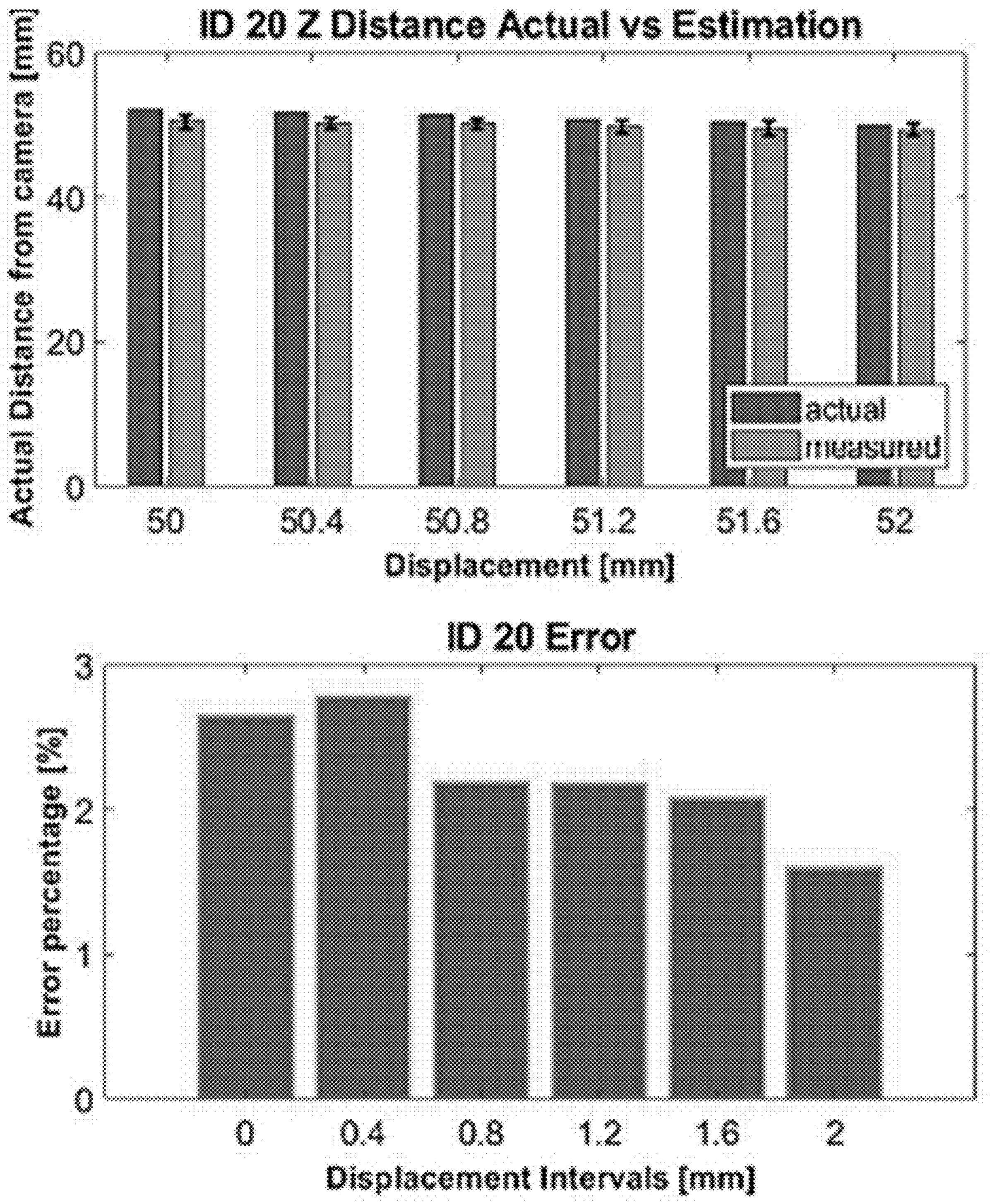
FIG. 26A through 26D are plots showing exemplary experimental results showing a comparison of the Z depth estimation of exemplary ArUco markers (i.e., ID 20, ID 21, ID 40, and ID 47 as marked in FIG. 24) with their actual displacement in accordance with some embodiments. The figure also shows the corresponding relative error percentages of these markers.
Figure 26B:
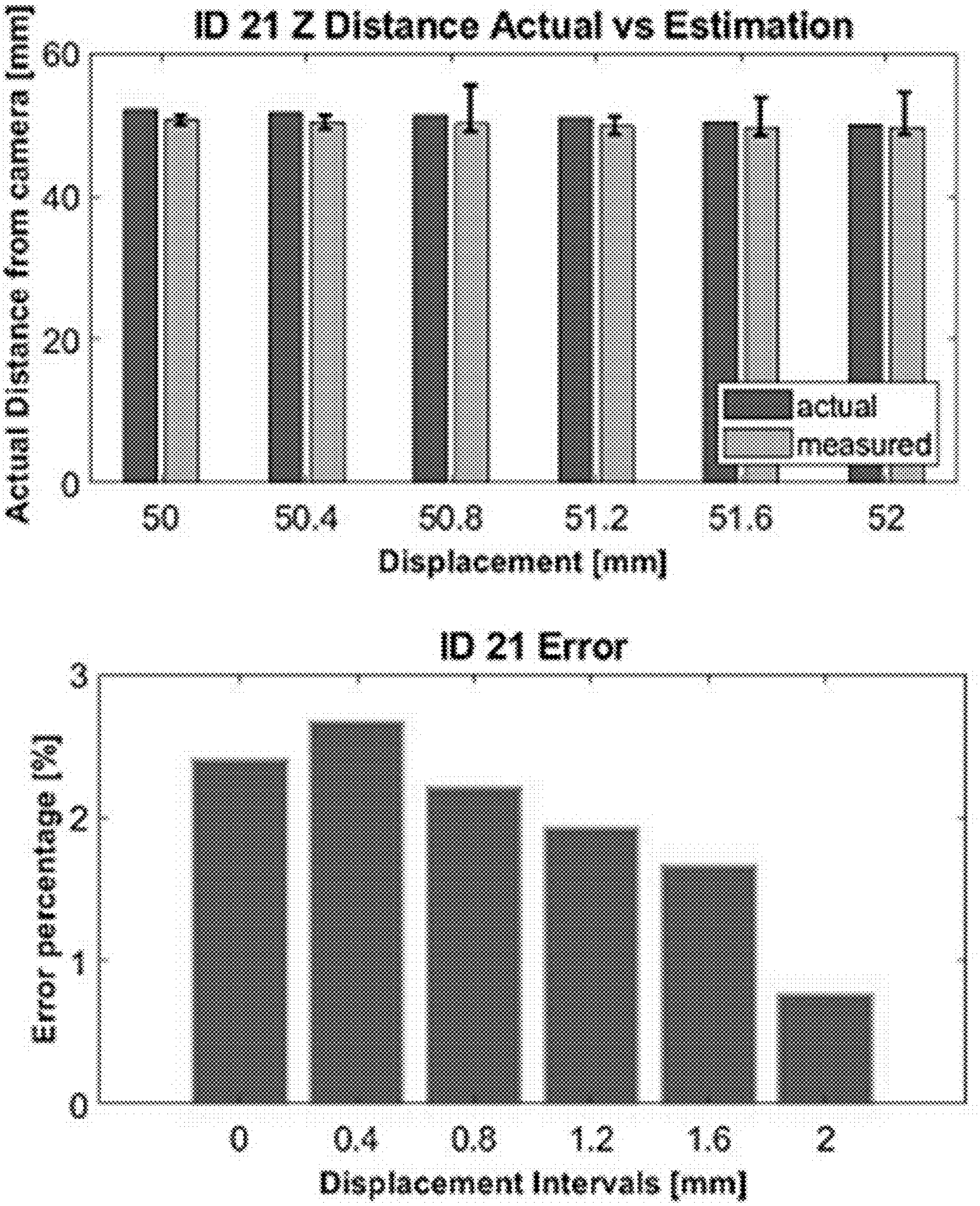
Figure 26C:
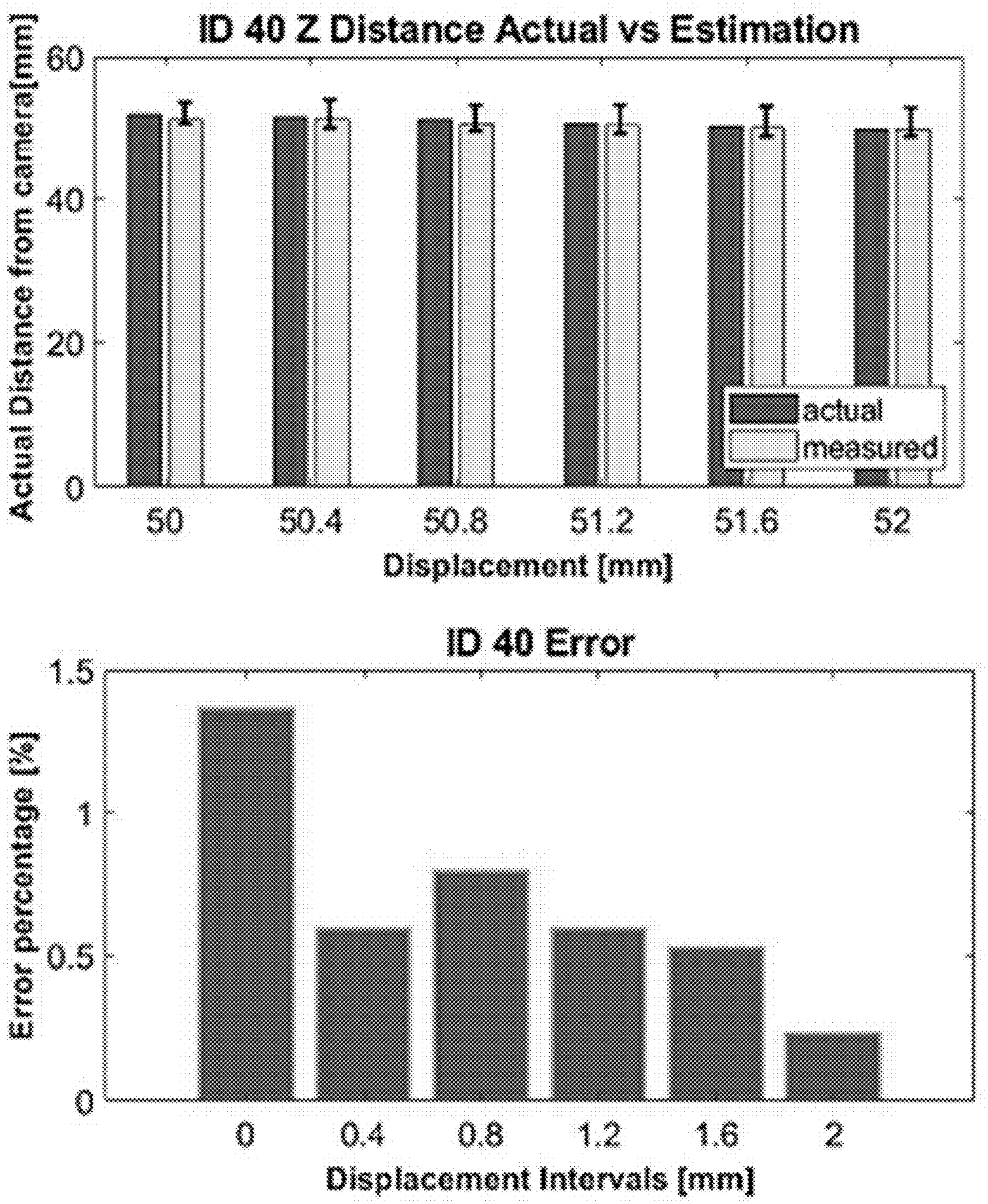
Figure 26D:
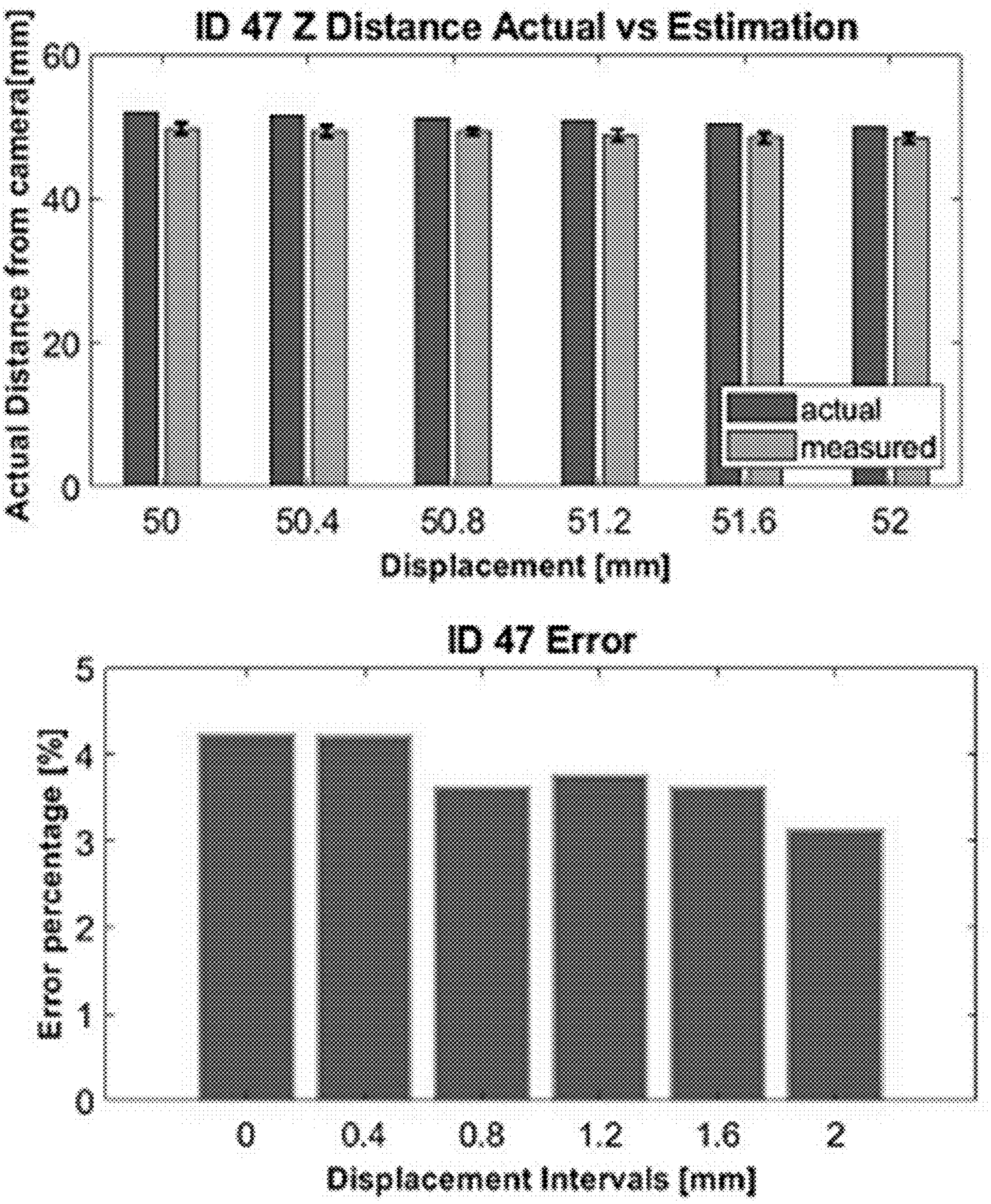

FIG. 25 demonstrates the experimental setup used to conduct characterization tests for Q-VTS and obtain the displacement and orientation of each ArUco marker during the interaction with a flat object normally pressed on the gel layer, where 1 is a MUMR12.40 Precision Linear Stage, 2 is the 25 AruCo Markers pattern, is a Mark-10 Series 5 Digital Force Gauge, 4 is a Q-VTS sensor, 5 is the Q-VTS's deformable gel layer with attached ArUco Markers and where 2 mm nuts were placed to indicate the small-scaled markers (1.5 mm×1.5 mm), 6 is the output of the real-time detection of each marker, is the 3D printed flat object used for characterization experiments, 8 is a Dell Latitude 5400 laptop used for the data processing and real-time marker detection and pose estimation, and 9 is a 10×7 sized checkerboard used for the camera calibration with 1.5 mm×1.5 mm squares.

As shown, the experimental setup included of the Q-VTS, a 3D printed flat square object designed for testing the Q-VTS deformation measurement, a single-row linear stage with 1 μm precision (M-UMR12.40, Newport) for the precise control of the flat square plate displacement, a digital force gauge with 0.02 N resolution (Mark-10 Series 5, Mark10 Corporation) attached to the linear stage to track the interaction force between the flat square plate and Q-VTS, and a Dell Latitude 5400 for streaming and recording the video for data processing. Spyder, the Scientific Python Development Software, was used to complete the camera calibration and process the acquired ArUco Marker data for the pose estimation.

In order to evaluate the performance of the Q-VTS in detecting the ArUco markers attached to the sensor surface and the pose estimation, a camera calibration was performed using OpenCV. Of note, camera calibration was one of the most essential steps to identify markers correctly and determine each marker's accurate orientation and distance vectors relying on 10×7 sized checkerboard that was patterned with 1.5 mm×1.5 mm squares. A set of 36 checkerboard images was used that were captured from different orientations and distances. After processing these checkerboard visuals, a 3×3 camera intrinsic matrix and radial and tangential distortion coefficients were obtained. Notably, a camera intrinsic matrix (CIM) is a unique matrix specific to a camera, including both focal length ($f_x$,$f_y$) and optical centers ($c_x$ and $c_y$) (see M. Beyeler, OpenCV with Python blueprints. Packt Publishing Ltd, 2015). It is expressed as a 3×3 matrix as CIM=[$f_x$ 0 $c_x$; 0 $f_y$ $c_y$; 0 0 1].

After the acquisition of both the CIM and distortion coefficients as an .yaml file, a 3D printed flat square plate was attached to the force gauge using the threaded connection at the base. Then, Q-VTS was fixed to the optical table to prevent any undesired slipping or sliding. Next, the linear stage was precisely moved until the square plate contacted the Q-VTS. Notably, a force gauge was placed on the linear stage to detect the initial touch between the square plate and Q-VTS to ensure that there was no deformation during the initial positioning. After arranging the hardware for measurements, the main detection and pose estimation algorithm was initialized to screen frame numbers, recognized marker IDs in real-time, and record numerical data involving detection rate, pose, and the orientation of each ArUco marker to the excel file. During the characterization experiment, a square flat plate was driven 0.4 mm per 200 frames until 2 mm displacement to record the pose for each displacement.

Figure 27:
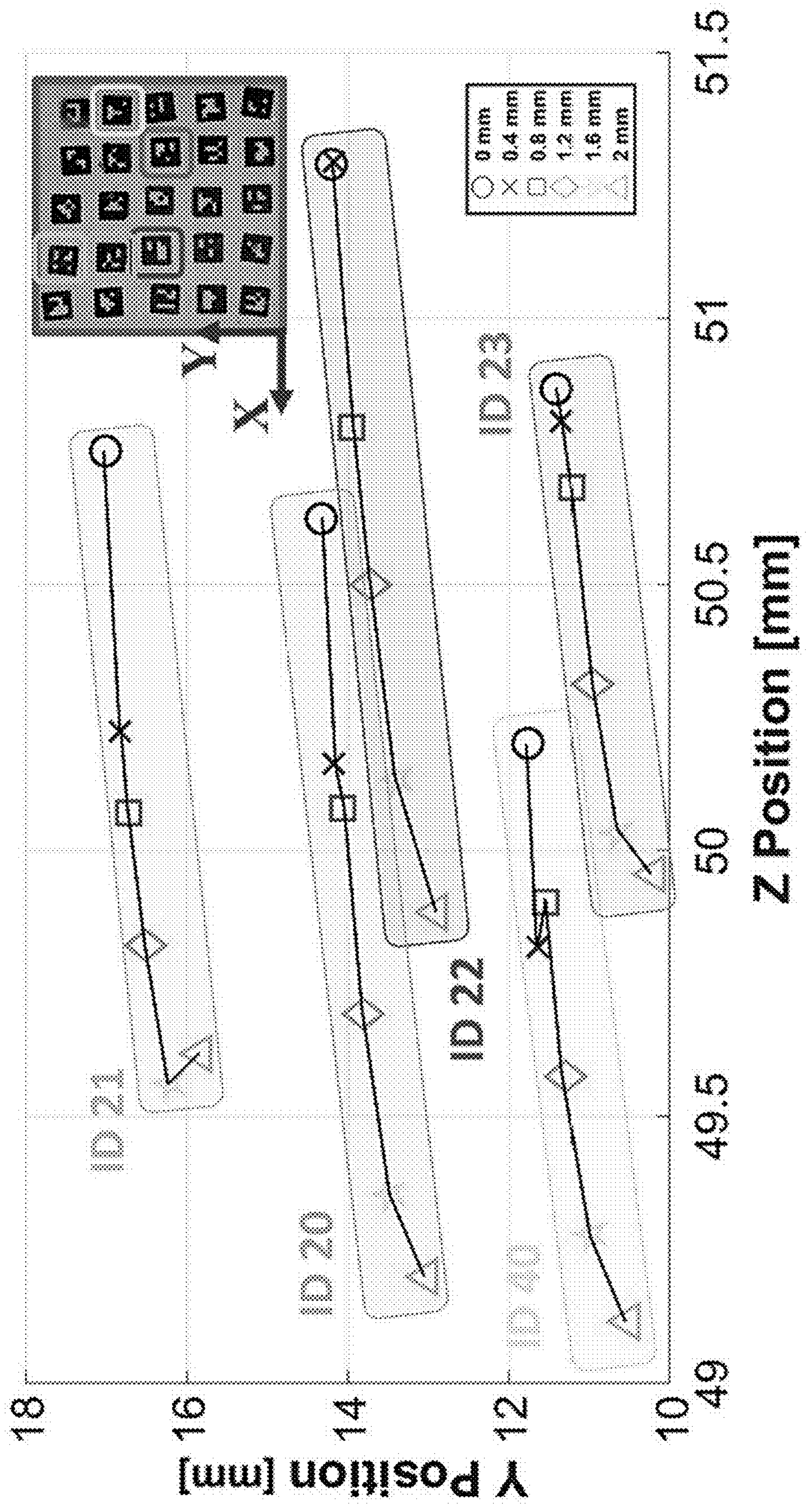
FIG. 27 is a plot showing exemplary experimental results showing trajectories of exemplary ArUco markers (ID 20, ID 21, ID 22, ID 21, and ID 40) are demonstrated when the V-QTS has displaced a total of 0.2 mm with 0.4 mm intervals in accordance with some embodiments. Each marker is color-coded in order to identify their similar behavior easily. Each geometrical marker represents the position of ArUco markers during the deformation procedure.

FIGS. 26A-26D depict the comparison of Z depth estimation of four exemplary AruCo Markers (i.e., ID 20, ID 21, ID 40, and ID 47 as marked in FIG. 24) with their actual Z displacement applied using the linear stage. As shown, a total deformation of 2 mm with 0.4 mm intervals has been considered for analyzing each ID and evaluating the performance of the detection algorithm. These figures also report the percentage of the relative error in estimating the deformation of the gel layer at the location of the considered IDs and during the deformation intervals. It can be easily seen from the error bars that a maximum error of 4.23% between the estimation and actual distance from the camera occurs for the ID 47 marker during all the intervals. On the other hand, the average measurement error for all other exemplary markers is around 2%, which signifies that the V-QTS sensor can reliably quantify the displacement of an object in different interaction locations with the sensor gel layer. Moreover, FIG. 27 shows the trajectory of four exemplary tags (i.e., ID 20, ID 21, ID 22, and ID 23 as marked in FIG. 24) the flat plate was pushed towards the Z direction with 0.4 mm intervals. As shown, the detection algorithm can reliably follow the trajectory of the detected markers during the deformation process. Notably, this critical feature enables shape reconstruction of the deformed gel layer to represent a dynamic deformation over time quantitatively.

Figure 28:
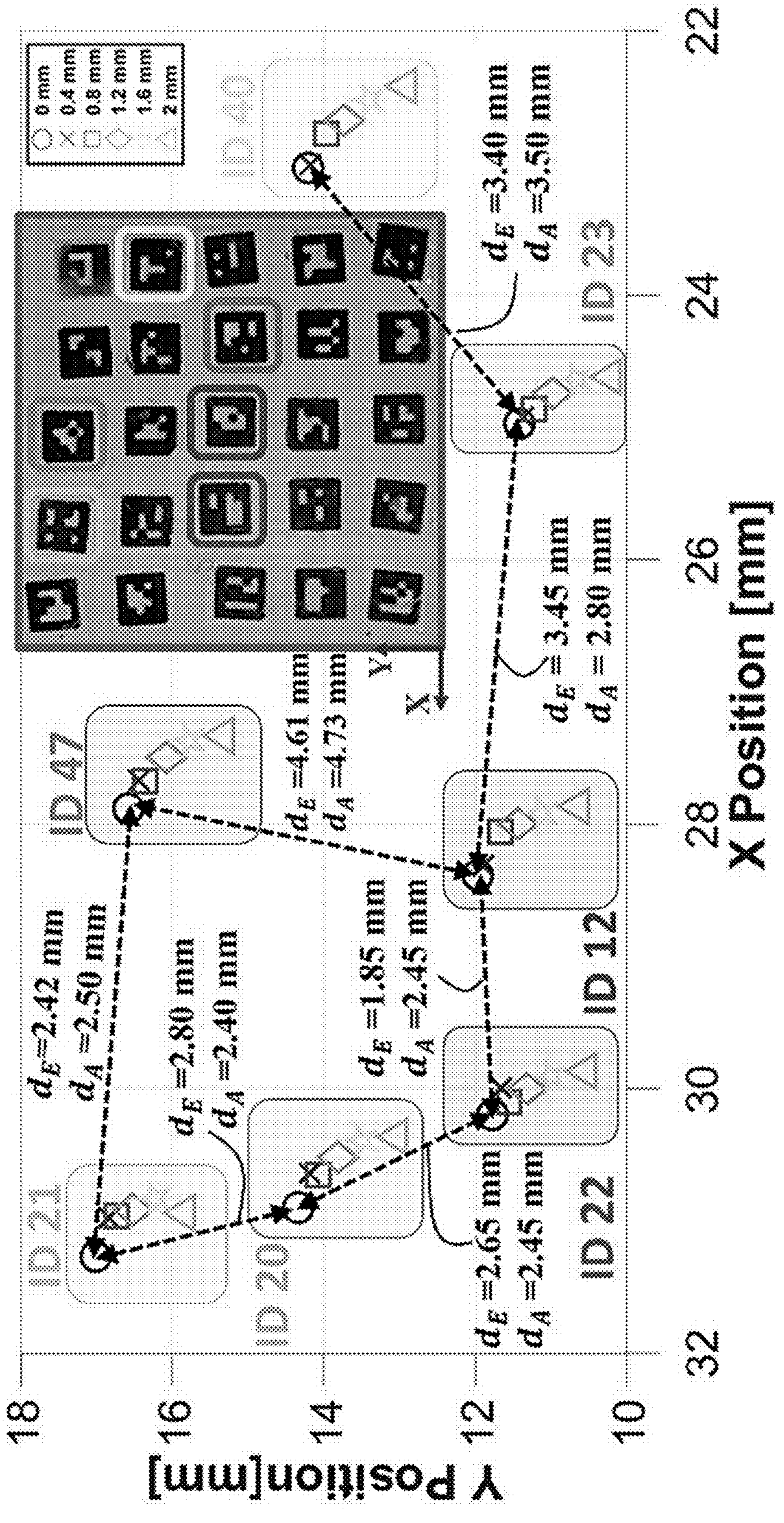
FIG. 28 is a plot showing exemplary experimental results showing position of the exemplary markers (i.e., ID 12, ID 20, ID 21, ID 40, and ID 47 as marked in FIG. 24) color coded with respect to their X and Y position in the image space as the gel layer is sequentially deformed up to 2 mm with 0.4 mm intervals in accordance with some embodiments. The figure also compares the calculated estimated distances (de) between different IDs and their corresponding actual measured values (da).

FIG. 28 also shows the position of the exemplary markers (i.e., ID 12, ID 20, ID 21, ID 40, and ID 47 as marked in FIG. 24) color coded with respect to their X and Y position in the image space as the gel layer is sequentially deformed up to 2 mm with 0.4 mm intervals. As seen in this figure, Q-VTS can identify and detect the markers in correct pattern sequences through the whole deformation procedure. In this figure, the deformation of each marker has been shown with a particular geometrical marker to better show its estimated deformation trajectory. Of note, as shown in FIG. 24 and expected, in the performed experiments, due to the deformation and dome-shape of the gel layer, each marker has experienced a lateral movement in the X and Y direction. Moreover, the calculated estimated distances (de) between different IDs greatly agree with their actual measured values (da), indicating the great performance of the Q-VTS in estimating the X and Y location of markers with respect to the camera location. As indicated, the error of estimated distances between all markers is less than 0.5 mm. Additionally, the deformation progression of each marker is consistent with the performed experiments.

In summary, a vision based tactile sensor (called Q-VTS) was designed and built to address the limitations of conventional VTSs, including the time-consuming and arduous fabrication methods for the marker attachment, inconsistent marking patterns and wrinkling problems that deteriorate the quality of the tactile information extraction, and lack of quantitative deformation evaluation of typical VTSs. Thanks to the use of ArUco markers enables an accurate estimation of the gel layer deformation in X, Y, and Z directions regardless of the placement of ArUco markers. The performance and efficacy of Q-VTS in estimating the deformation of the sensor's gel layer were experimentally evaluated and verified. An accurate estimation of the deformation of the gel layer with a low relative error of <5% in the Z direction and less than 0.5 mm in both the X and Y direction was achieved.

The following references are incorporated herein by reference in their entirety:

Centers for Disease Control and Prevention, "Colorectal Cancer Statistics," Colorectal Cancer. pp. 4-7, 2013, Accessed: May 2, 2021. [Online]. Available: https://www.cdc.gov/cancer/colorectal/statistics/index.htm.

Japanese Gastric Cancer Association, 2017. Japanese gastric cancer treatment guidelines 2014 (ver. 4). Gastric cancer, 20 (1), pp. 1-19.

Jung, K., Park, M. I., Kim, S. E. and Park, S. J., 2016. Borrmann type 4 advanced gastric cancer: focus on the development of scirrhous gastric cancer. Clinical endoscopy, 49 (4), p. 336.

Li, C., Oh, S. J., Kim, S., Hyung, W. J., Yan, M., Zhu, Z. G. and Noh, S. H., 2009. Macroscopic Borrmann type as a simple prognostic indicator in patients with advanced gastric cancer. Oncology, 77 (3-4), pp. 197-204.

An, J. Y., Kang, T. H., Choi, M. G., Noh, J. H., Sohn, T. S. and Kim, S., 2008. Borrmann type IV: an independent prognostic factor for survival in gastric cancer. Journal of Gastrointestinal Surgery, 12 (8), pp. 1364-1369.

Shia, J., Schultz, N., Kuk, D., Vakiani, E., Middha, S., Segal, N. H., Hechtman, J. F., Berger, M. F., Stadler, Z. K., Weiser, M. R. and Wolchok, J. D., 2017. Morphological characterization of colorectal cancers in The Cancer Genome Atlas reveals distinct morphology-molecular associations: clinical and biological implications. Modern pathology, 30 (4), pp. 599-609.

A. Z. Gimeno-García et al., "Displasia de alto grado como factor de riesgo de neoplasia colorrectal avanzada metacrónica, en pacientes con adenomas avanzados," Gastroenterol. Hepatol., vol. 30, no. 4, pp. 207-211, April 2007, doi: 10.1157/13100586.

S. Patino-Barrientos, D. Sierra-Sosa, B. Garcia-Zapirain, C. Castillo-Olea, and A. Elmaghraby, "Kudo's classification for colon polyps assessment using a deep learning approach," Appl. Sci., vol. 10, no. 2, p. 501, January 2020, doi: 10.3390/app10020501.

Ikoma, N., 2020. ASO Author Reflections: Fluorescent-Image Guidance in Surgical Oncology. Annals of surgical oncology, 27 (13), pp. 5323-5324.

H. Awadie and M. J. Bourke, "When colonoscopy fails . . . . Refer, Repeat, and Succeed," GE Portuguese Journal of Gastroenterology, vol. 25, no. 6. pp. 279-281, 2018, doi: 10.1159/000486804.

J. Lee et al., "Risk factors of missed colorectal lesions after colonoscopy," Med. (United States), vol. 96, no. 27, July 2017, doi: 10.1097/MD. 0000000000007468.

"Flat polyps: Why finding them requires skill," UCI Health, 2017. https://www.ucihealth.org/blog/2017/03/flat-polyps-colonoscopy (accessed May 2, 2021).

A. C. Bateman and P. Patel, "Lower gastrointestinal endoscopy: guidance on indications for biopsy," Frontline Gastroenterol., vol. 5, no. 2, pp. 96-102, April 2014, doi: 10.1136/flgastro-2013-100412.

N. Hoerter, S. A. Gross, and P. S. Liang, "Artificial Intelligence and Polyp Detection," Curr. Treat. Options Gastroenterol., vol. 18, no. 1, pp. 120-136, March 2020, doi: 10.1007/s11938-020-00274-2.

S. J. Thakkar and G. S. Kochhar, "Artificial intelligence for real-time detection of early esophageal cancer: another set of eyes to better visualize," Gastrointestinal Endoscopy, vol. 91, no. 1. Mosby Inc., pp. 52-54, Jan. 1, 2020, doi: 10.1016/j.gie. 2019.09.036.

Medtronic, "GI Genius™ Intelligent Endoscopy Module|Medtronic," 2020. https://www.medtronic.com/covidien/en-gb/products/gastrointestinal-artificial-intelligence/gi-genius-intelligent-endoscopy.html (accessed May 2, 2021).

Liu, Y. and Alambeigi, F., 2021. Effect of External and Internal Loads on Tension Loss of Tendon-Driven Continuum Manipulators. IEEE Robotics and Automation Letters, 6 (2), pp. 1606-1613.

A. Bhandari, M. Woodhouse, and S. Gupta, "Colorectal cancer is a leading cause of cancer incidence and mortality among adults younger than 50 years in the USA: a SEER-based analysis with comparison to other young-onset cancers," vol. 65, no. 2, p. 311.

P. Greenwald, "Colon cancer overview," vol. 70, pp. 1206-1215. Publisher: John Wiley & Sons, Ltd.

D. Camboni, L. Massari, M. Chiurazzi, R. Calio, J. O. Alcaide, J. D'Abbraccio, E. Mazomenos, D. Stoyanov, A. Menciassi, M. C. Carrozza, P. Dario, C. M. Oddo, and G. Ciuti, "Endoscopic tactile capsule for non-polypoid colorectal tumour detection," vol. 3, no. 1, pp. 64-73.

S. Kudo, S. Tamura, T. Nakajima, H. Yamano, H. Kusaka, and H. Watanabe, "Diagnosis of colorectal tumorous lesions by magnifying endoscopy," vol. 44, no. 1, pp. 8-14.

Endoscopic Classification Review Group, "Update on the paris classification of superficial neoplastic lesions in the digestive tract," vol. 37, no. 6, pp. 570-578. 570.

V. K. Dik, "Endoscopic innovations to increase the adenoma detection rate during colonoscopy," vol. 20, no. 9, p. 2200. Publisher: Baishideng Publishing Group Inc.

N. Gilani, S. Stipho, J. D. Panetta, S. Petre, M. A. Young, and F. C. Ramirez, "Polyp detection rates using magnification with narrow band imaging and white light," vol. 7, no. 5, p. 555. Publisher: Baishideng Publishing Group Inc.

T. D. Wang and J. Van Dam, "Optical biopsy: a new frontier in endoscopic detection and diagnosis," vol. 2, no. 9, pp. 744-753.

F. Bianchi, E. Trallori, D. Camboni, C. M. Oddo, A. Menciassi, G. Ciuti, and P. Dario, "Endoscopic tactile instrument for remote tissue palpation in colonoscopic procedures," in 2017 IEEE International Conference on Cyborg and Bionic Systems (CBS), pp. 248-252.

U. Ladabaum, A. Fioritto, A. Mitani, M. Desai, J. P. Kim, D. K. Rex, T. Imperiale, and N. Gunaratnam, "Real-time optical biopsy of colon polyps with narrow band imaging in community practice does not yet meet key thresholds for clinical decisions," vol. 144, no. 1, pp. 81-91. Edition: 2012 Oct. 3.

G. Ciuti, R. Calio, D. Camboni, L. Neri, F. Bianchi, A. Arezzo, A. Koulaouzidis, S. Schostek, D. Stoyanov, C. M. Oddo, B. Magnani, A. Menciassi, M. Morino, M. O. Schurr, and P. Dario, "Frontiers of robotic endoscopic capsules: a review," vol. 11, no. 1, pp. 1-18. Publisher: Springer Science and Business Media LLC.

C. Chi, X. Sun, N. Xue, T. Li, and C. Liu, "Recent progress in technologies for tactile sensors," vol. 18, no. 4.

T. Kaltenbach, J. C. Anderson, C. A. Burke, J. A. Dominitz, S. Gupta, D. Lieberman, D. J. Robertson, A. Shaukat, S. Syngal, and D. K. Rex, "Endoscopic removal of colorectal lesions: Recommendations by the US multi-society task force on colorectal cancer," vol. 115, no. 3.

I. Bandyopadhyaya, D. Babu, A. Kumar, and J. Roychowdhury, "Tactile sensing based softness classification using machine learning," IEEE.

W. Yuan, S. Dong, and E. H. Adelson, "GelSight: High-resolution robot tactile sensors for estimating geometry and force," vol. 17, no. 12.

E. A. M. Heijnsdijk, M. van der Voort, H. de Visser, J. Dankelman, and D. J. Gouma, "Inter- and intraindividual variabilities of perforation forces of human and pig bowel tissue," vol. 17, no. 12, pp. 1923-1926.
P. Baki, G. Szekely, and G. K' osa, "Design and characterization of a' novel, robust, tri-axial force sensor," vol. 192, pp. 101-110.
A. Abiri, Y.-Y. Juo, A. Tao, S. J. Askari, J. Pensa, J. W. Bisley, E. P. Dutson, and W. S. Grundfest, "Artificial palpation in robotic surgery using haptic feedback," vol. 33, no. 4, pp. 1252-1259. Publisher: Springer Science and Business Media LLC.
H. Park, K. Park, S. Mo, and J. Kim, "Deep neural network based electrical impedance tomographic sensing methodology for large-area robotic tactile sensing," pp. 1-14.
H. Park, H. Lee, K. Park, S. Mo, and J. Kim, "Deep neural network approach in electrical impedance tomography-based real-time soft tactile sensor," in 2019 IEEE/RSJ International Conference on Intelligent Robots and Systems (IROS), pp. 7447-7452.
B. Winstone, C. Melhuish, T. Pipe, M. Callaway, and S. Dogramadzi, "Toward bio-inspired tactile sensing capsule endoscopy for detection of submucosal tumors," vol. 17, no. 3, pp. 848-857.
B. Ward-Cherrier, N. Pestell, L. Cramphorn, B. Winstone, M. E. Giannaccini, J. Rossiter, and N. F. Lepora, "The TacTip family: Soft optical tactile sensors with 3d-printed biomimetic morphologies," vol. 5, no. 2, pp. 216-227. Publisher: Mary Ann Liebert, Inc., publishers.
S. Dong, W. Yuan, and E. H. Adelson, "Improved GelSight tactile sensor for measuring geometry and slip," in 2017 IEEE/RSJ International Conference on Intelligent Robots and Systems (IROS), pp. 137-144.
Y. Liu, S. H. Ahn, U. Yoo, A. R. Cohen, and F. Alambeigi, "Toward analytical modeling and evaluation of curvature-dependent distributed friction force in tendon-driven continuum manipulators," pp. 8823-8828.
M. A. Turk and A. P. Pentland, "Face recognition using eigenfaces," in Proceedings. 1991 IEEE Computer Society Conference on Computer Vision and Pattern Recognition, pp. 586-591.
W. S. Noble, "What is a support vector machine?," vol. 24, no. 12, pp. 1565-1567.
J. Zhu, A. Cherubini, C. Dune, D. Navarro-Alarcon, F. Alambeigi, D. Berenson, F. Ficuciello, K. Harada, X. Li, J. Pan et al., "Challenges and outlook in robotic manipulation of deformable objects," arXiv preprint arXiv: 2105.01767, 2021.
U. H. Shah, R. Muthusamy, D. Gan, Y. Zweiri, and L. Seneviratne, "On the design and development of vision-based tactile sensors," Journal of Intelligent & Robotic Systems, vol. 102, no. 4, pp. 1-27, 2021.
M. K. Johnson and E. H. Adelson, "Retrographic sensing for the measurement of surface texture and shape," in 2009 IEEE Conference on Computer Vision and Pattern Recognition. IEEE, 2009, pp. 1070-1077.
R. Li and E. H. Adelson, "Sensing and recognizing surface textures using a gelsight sensor," in Proceedings of the IEEE Conference on Computer Vision and Pattern Recognition, 2013, pp. 1241-1247.
W. Yuan, S. Dong, and E. H. Adelson, "Gelsight: High-resolution robot tactile sensors for estimating geometry and force," Sensors, vol. 17, no. 12, p. 2762, 2017.
R. Li, R. Platt, W. Yuan, A. ten Pas, N. Roscup, M. A. Srinivasan, and E. Adelson, "Localization and manipulation of small parts using gelsight tactile sensing," in 2014 IEEE/RSJ International Conference on Intelligent Robots and Systems. IEEE, 2014, pp. 3988-3993.
W. Yuan, C. Zhu, A. Owens, M. A. Srinivasan, and E. H. Adelson, "Shape-independent hardness estimation using deep learning and a gelsight tactile sensor," in 2017 IEEE International Conference on Robotics and Automation (ICRA). IEEE, 2017, pp. 951-958.
A. C. Abad and A. Ranasinghe, "Visuotactile sensors with emphasis on gelsight sensor: A review," IEEE Sensors Journal, vol. 20, no. 14, pp. 7628-7638, 2020.
W. Yuan et al., "Tactile measurement with a gelsight sensor," Ph.D. dissertation, Massachusetts Institute of Technology, 2014.
M. K. Johnson, F. Cole, A. Raj, and E. H. Adelson, "Microgeometry capture using an elastomeric sensor," ACM Transactions on Graphics (TOG), vol. 30, no. 4, pp. 1-8, 2011.
N. R. Sinatra, C. B. Teeple, D. M. Vogt, K. K. Parker, D. F. Gruber, and R. J. Wood, "Ultragentle manipulation of delicate structures using a soft robotic gripper," Science Robotics, vol. 4, no. 33, p. eaax5425, 2019.
Y. Liu, T. G. Mohanraj, M. R. Rajebi, L. Zhou, and F. Alambeigi, "Multiphysical analytical modeling and design of a magnetically steerable robotic catheter for treatment of peripheral artery disease," IEEE/ASME Transactions on Mechatronics, 2022.
N. Venkatayogi, O. C. Kara, J. Bonyun, N. Ikoma, and F. Alambeigi, "Classification of colorectal cancer polyps via transfer learning and vision-based tactile sensing," To be appeared in 2022 IEEE Sensors.
T. Kaltenbach, J. C. Anderson, C. A. Burke, J. A. Dominitz, S. Gupta, D. Lieberman, D. J. Robertson, A. Shaukat, S. Syngal, and D. K. Rex, "Endoscopic removal of colorectal lesions-recommendations by the us multi-society task force on colorectal cancer," Gastroenterology, vol. 158, no. 4, pp. 1095-1129, 2020.
H. Heo, Y. Jin, D. Yang, C. Wier, A. Minard, N. B. Dahotre, and A. Neogi, "Manufacturing and characterization of hybrid bulk voxelated biomaterials printed by digital anatomy 3d printing," Polymers, vol. 13, no. 1, p. 123, 2020.
A. Mittal, A. K. Moorthy, and A. C. Bovik, "No-reference image quality assessment in the spatial domain," IEEE Transactions on image processing, vol. 21, no. 12, pp. 4695-4708, 2012.
R. S. Dahiya, M. Valle, et al., "Tactile sensing for robotic applications," Sensors, Focus on Tactile, Force and Stress Sensors, pp. 298-304, 2008.
A. Yamaguchi and C. G. Atkeson, "Recent progress in tactile sensing and sensors for robotic manipulation: can we turn tactile sensing into vision?" Advanced Robotics, vol. 33, no. 14, pp. 661-673, 2019.
G. Li, S. Liu, L. Wang, and R. Zhu, "Skin-inspired quadruple tactile sensors integrated on a robot hand enable object recognition," Science Robotics, vol. 5, no. 49, p. eabc8134, 2020.
J. M. Gandarias, J. M. Gomez-de Gabriel, and A. J. Garc'ia-Cerezo, "Enhancing perception with tactile object recognition in adaptive grippers for human-robot interaction," Sensors, vol. 18, no. 3, p. 692, 2018.
F. Ju, Y. Wang, Z. Zhang, Y. Wang, Y. Yun, H. Guo, and B. Chen, "A miniature piezoelectric spiral tactile sensor for tissue hardness palpation with catheter robot in minimally invasive surgery," Smart Materials and Structures, vol. 28, no. 2, p. 025033, 2019.
Y. Liu, R. Bao, J. Tao, J. Li, M. Dong, and C. Pan, "Recent progress in tactile sensors and their applications in intelligent systems," Science Bulletin, vol. 65, no. 1, pp. 70-88, 2020.

M. Park, B.-G. Bok, J.-H. Ahn, and M.-S. Kim, "Recent advances in tactile sensing technology," Micromachines, vol. 9, no. 7, p. 321, 2018.

N. Kattavenos, B. Lawrenson, T. Frank, M. Pridham, R. Keatch, and A. Cuschieri, "Force-sensitive tactile sensor for minimal access surgery," Minimally Invasive Therapy & Allied Technologies, vol. 13, no. 1, pp. 42-46, 2004.

J. Dargahi, S. Najarian, and K. Najarian, "Development and threedimensional modelling of a biological-tissue grasper tool equipped with a tactile sensor," Canadian Journal of Electrical and Computer Engineering, vol. 30, no. 4, pp. 225-230, 2005.

M. S. Arian, C. A. Blaine, G. E. Loeb, and J. A. Fishel, "Using the biotac as a tumor localization tool," in 2014 IEEE Haptics Symposium (HAPTICS). IEEE, 2014, pp. 443-448.

P. S. Wellman, E. P. Dalton, D. Krag, K. A. Kern, and R. D. Howe, "Tactile imaging of breast masses: first clinical report," Archives of surgery, vol. 136, no. 2, pp. 204-208, 2001.

N. Wettels, V. J. Santos, R. S. Johansson, and G. E. Loeb, "Biomimetic tactile sensor array," Advanced Robotics, vol. 22, no. 8, pp. 829-849, 2008.

W. Othman and M. A. Qasaimeh, "Tactile sensing for minimally invasive surgery: Conventional methods and potential emerging tactile technologies," Frontiers in Robotics and AI, p. 376, 2021.

C.-H. Won, J.-H. Lee, and F. Saleheen, "Tactile sensing systems for tumor characterization: A review," IEEE Sensors Journal, vol. 21, no. 11, pp. 12578-12588, 2021.

C.-H. Chuang, T.-H. Li, I.-C. Chou, and Y.-J. Teng, "Piezoelectric tactile sensor for submucosal tumor detection in endoscopy," Sensors and Actuators A: Physical, vol. 244, pp. 299-309, 2016.

R. Ahmadi, S. Arbatani, M. Packirisamy, and J. Dargahi, "Microoptical force distribution sensing suitable for lump/artery detection," Biomedical microdevices, vol. 17, no. 1, pp. 1-12, 2015.

A. Yamaguchi and C. G. Atkeson, "Tactile behaviors with the visionbased tactile sensor fingervision," International Journal of Humanoid Robotics, vol. 16, no. 03, p. 1940002, 2019.

K. Shimonomura, "Tactile image sensors employing camera: A review," Sensors, vol. 19, no. 18, p. 3933, 2019.

W. K. Do and M. Kennedy, "Densetact: Optical tactile sensor for dense shape reconstruction," in 2022 International Conference on Robotics and Automation (ICRA). IEEE, 2022, pp. 6188-6194.

W. Kim, W. D. Kim, J.-J. Kim, C.-H. Kim, and J. Kim, "Uvtac: Switchable uv marker-based tactile sensing finger for effective force estimation and object localization," IEEE Robotics and Automation Letters, vol. 7, no. 3, pp. 6036-6043, 2022.

K. Kamiyama, K. Vlack, T. Mizota, H. Kajimoto, K. Kawakami, and S. Tachi, "Vision-based sensor for real-time measuring of surface traction fields," IEEE Computer Graphics and Applications, vol. 25, no. 1, pp. 68-75, 2005.

K. Sato, K. Kamiyama, N. Kawakami, and S. Tachi, "Finger-shaped gelforce: sensor for measuring surface traction fields for robotic hand," IEEE Transactions on Haptics, vol. 3, no. 1, pp. 37-47, 2009.

X. Lin, L. Willemet, A. Bailleul, and M. Wiertlewski, "Curvature sensing with a spherical tactile sensor using the color-interference of a marker array," in 2020 IEEE International Conference on Robotics and Automation (ICRA). IEEE, 2020, pp. 603-609.

X. Lin and M. Wiertlewski, "Sensing the frictional state of a robotic skin via subtractive color mixing," IEEE Robotics and Automation Letters, vol. 4, no. 3, pp. 2386-2392, 2019.

K. Nozu and K. Shimonomura, "Robotic bolt insertion and tightening based on in-hand object localization and force sensing," in 2018 IEEE/ASME International Conference on Advanced Intelligent Mechatronics (AIM). IEEE, 2018, pp. 310-315.

S. Garrido-Jurado, R. Munoz-Salinas, F. J. Madrid-Cuevas, and M. J. Marin-Jimenez, "Automatic generation and detection of highly reliable' fiducial markers under occlusion," Pattern Recognition, vol. 47, no. 6, pp. 2280-2292, 2014.

F. P. Villani, M. D. Cosmo, A. B. Simonetti, E. Frontoni, and'S. Moccia, "Development of an augmented reality system based on marker tracking for robotic assisted minimally invasive spine surgery," in International Conference on Pattern Recognition. Springer, 2021, pp. 461-475.

C. Mela, F. Papay, and Y. Liu, "Novel multimodal, multiscale imaging system with augmented reality," Diagnostics, vol. 11, no. 3, p. 441, 2021.

A. de Oliveira Junior, L. Piardi, E. G. Bertogna, and P. Leitao," "Improving the mobile robots indoor localization system by combining slam with fiducial markers," in 2021 Latin American Robotics Symposium (LARS), 2021 Brazilian Symposium on Robotics (SBR), and 2021 Workshop on Robotics in Education (WRE). IEEE, 2021, pp. 234-239.

M. Kalaitzakis, B. Cain, S. Carroll, A. Ambrosi, C. Whitehead, and N. Vitzilaios, "Fiducial markers for pose estimation," Journal of Intelligent & Robotic Systems, vol. 101, no. 4, pp. 1-26, 2021.

E. Olson, "Apriltag: A robust and flexible visual fiducial system," in 2011 IEEE international conference on robotics and automation. IEEE, 2011, pp. 3400-3407.

M. Fiala, "Artag, a fiducial marker system using digital techniques," in 2005 IEEE Computer Society Conference on Computer Vision and Pattern Recognition (CVPR'05), vol. 2. IEEE, 2005, pp. 590-596.

"Aruco markers generator!" Accessed: 2022 Jul. 23. [Online]. Available: https://chev.me/arucogen/M.

M. Beyeler, OpenCV with Python blueprints. Packt Publishing Ltd, 2015.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention.

What is claimed is:

1. A four-dimensional tactile sensing system, comprising:

a housing having a distal end and a proximal end;

a camera positioned at the distal end of the housing, wherein the camera is oriented to image an area in front of the distal end of the housing; and at least one tactile sensor device positioned on an exterior surface of the housing, comprising:

a support plate having a first surface and a second surface;

an elastomer attached adjacent to the first surface of the support plate;

a second camera positioned at a distance from the second surface of the support plate;

at least one light source positioned proximate to the second surface of the support plate and the camera;

wherein the at least one tactile sensor device is configured to apply a force to a target; and a non-transitory computer-readable medium with instructions stored thereon, that when executed by a processor, perform the steps of:

acquiring a set of input images of a target via the camera of the at least one tactile sensor device while applying a force to the target via the at least one tactile sensor device, each input image having an associated known target type and an applied force value at the time of image acquisition;

performing a principal component analysis on the set of input images to calculate a set of parameters for each image of the set of input images;

providing the sets of parameters to a support vector machine to calculate a set of support vectors to classify the parameters; and selecting a subset of the set of support vectors and an applied force threshold, such that for images having an applied force above the applied force threshold, the set of support vectors is configured to predict a target type from the parameters with a characterization confidence of at least 80%.

2. The system of claim 1, wherein the housing comprises a pneumatically controlled robot or a cable controlled robot, wherein the robot comprises a compliant material.

3. The system of claim 1, wherein the housing comprises a pneumatic actuation system configured to move the at least one tactile sensor device relative to the housing, such that the at least one tactile sensor device applies a force to a target.

4. The system of claim 1, wherein the housing further comprises a skin positioned on an exterior surface of the housing, and wherein the at least one tactile sensor device is embedded in the skin.

5. A four-dimensional tactile sensing system, comprising:

a housing having a distal end and a proximal end;

a camera positioned at the distal end of the housing, wherein the camera is oriented to image an area in front of the distal end of the housing; and at least one tactile sensor device positioned on an exterior surface of the housing, comprising:

a support plate having a first surface and a second surface;

an elastomer attached adjacent to the first surface of the support plate;

a second camera positioned at a distance from the second surface of the support plate;

at least one light source positioned proximate to the second surface of the support plate and the camera;

wherein the at least one tactile sensor device is configured to apply a force to a target; and a non-transitory computer-readable medium with instructions stored thereon, that when executed by a processor, perform the steps of:

obtaining a set of calculated support vectors to form a classification scheme;

obtaining a set of at least one input image of a target via the camera of the at least one tactile sensor device while applying a force to the target via the at least one tactile sensor device, the at least one input image having an associated applied force value at the time of image acquisition;

selecting a subset of the set of at least one input image having an associated applied force value above a threshold;

performing a principal component analysis on the subset of input images to calculate a set of parameters of each image in the subset; and applying the classification scheme to the set of parameters to classify the target.

6. The system of claim 5, wherein the housing comprises a pneumatically controlled robot or a cable controlled robot, wherein the robot comprises a compliant material.

7. The system of claim 5, wherein the housing comprises a pneumatic actuation system configured to move the at least one tactile sensor device relative to the housing, such that the at least one tactile sensor device applies a force to a target.

8. The system of claim 5, wherein the housing further comprises a skin positioned on an exterior surface of the housing, and wherein the at least one tactile sensor device is embedded in the skin.

* * * * *